(12) United States Patent
Shimatani-Shibata et al.

(10) Patent No.: US 8,383,398 B2
(45) Date of Patent: Feb. 26, 2013

(54) EXPRESSION VECTOR

(75) Inventors: Yuko Shimatani-Shibata, Matsumoto (JP); Hiromi Yonekura, Suwa (JP); Hitomi Shimizu, Matsumoto (JP)

(73) Assignee: Anaeropharma Science, Inc., Tokyo (JP)

( * ) Notice: Subject to any disclaimer, the term of this patent is extended or adjusted under 35 U.S.C. 154(b) by 576 days.

(21) Appl. No.: 12/425,001

(22) Filed: Apr. 16, 2009

(65) Prior Publication Data

US 2009/0264513 A1 Oct. 22, 2009

Related U.S. Application Data

(60) Provisional application No. 61/124,528, filed on Apr. 17, 2008.

(51) Int. Cl.
*C12N 15/00* (2006.01)
*C12N 15/74* (2006.01)
*A61K 48/00* (2006.01)
*C12N 1/21* (2006.01)

(52) U.S. Cl. ............... 435/320.1; 435/253.4; 435/252.3; 435/252.7; 536/23.1; 536/24.1; 514/44

(58) Field of Classification Search .................. None
See application file for complete search history.

(56) References Cited

U.S. PATENT DOCUMENTS

| 6,416,754 | B1 | 7/2002 | Brown et al. |
| 6,652,849 | B2 | 11/2003 | Brown et al. |
| 2003/0103952 | A1 | 6/2003 | Brown et al. |
| 2004/0014221 | A1* | 1/2004 | Ji et al. ........................ 435/471 |
| 2005/0227910 | A1* | 10/2005 | Yang et al. ........................ 514/2 |
| 2009/0176747 | A1* | 7/2009 | Pommier et al. ............... 514/154 |
| 2009/0291469 | A1* | 11/2009 | David ........................... 435/69.1 |

FOREIGN PATENT DOCUMENTS

| JP | 2002/97144 A | 4/2002 |
| WO | WO 2006/057289 | 1/2006 |
| WO | WO 2007/136107 | 11/2007 |

OTHER PUBLICATIONS

Waterfield et al, An origin of DNA replication from *Lactococcus lactis* bacteriophage c2, Appl. Environ. Microbiol. 1996, 62(4):1452.*
Posno et al, Incompatibility of *Lactobacillus* Vectors with Replicons Derived from Small Cryptic *Lactobacillus* Plasmids and Segregational Instability of the Introduced Vectors, 1991, Applied and Environmental Microbiology, pp. 1822-1828.*
Corneau et al, Molecular characterization of three plasmids from *Bifidobacterium longum*, Plasmid, 2004, vol. 51, pp. 87-100.*

(Continued)

*Primary Examiner* — Maria Marvich
(74) *Attorney, Agent, or Firm* — Jones Day

(57) ABSTRACT

A conventional shuttle vector constructed by fusing an *E. coli*-derived plasmid and a transformant-derived plasmid functions in both *E. coli* and the transformant bacterium, and there exists no expression vector that functions only in a non-*E. coli* transformant. The present invention provides an plasmid expression vector comprising (1) a plasmid replication unit that functions in an anaerobic microorganism other than *E. coli* and (2) a protein expression unit formed from DNA coding for a protein having target activity and a DNA fragment containing a promoter and a terminator that function in the anaerobic microorganism. The expression vector of the present invention is capable of being replicated only in a transformant, eliminating the risk of the replication of the transformant gene in other pathogenic or aerobic bacterium, providing an extremely safe and reliable vector and gene transporter for therapeutic application.

21 Claims, 5 Drawing Sheets

Constructing process of selective marker plasmid(pSPCM-pUCori)
(step1)

OTHER PUBLICATIONS

Shareck et al, Cloning Vectors Based on Cryptic Plasmids Isolated from Lactic Acid Bacteria: Their Characteristics and Potential Applications in Biotechnology, Critical Reviews in Biotechnology, 24(4):155-208 (2004).*

Shoemaker et al, Conjugal Transfer of a Shuttle Vector from the Human Colonic Anaerobe *Bacteroides uniformis* to the Ruminal Anaerobe *Prevotella (Bacteroides) ruminicola* B14, Applied and Environmental Microbiology 1991, pp. 2114-2120.*

Yazawa et al., "*Bifidobacterium longum* as a delivery system for cancer gene therapy: selective localization and growth in hypoxic tumors," 2000, Cancer Gene Ther. 7:269-274.

Yazawa et al., "*Bifidobacterium longum* as a delivery system for gene therapy of chemically induced rat mammary tumors," 2001, Breast Cancer Res. Treat., 66:165-170.

Nakamura et al., "Cloned cytosine deaminase gene expression of *Bifidobacterium longum* and application to enzyme/pro-drug therapy of hypoxic solid tumors," 2002, Biosci. Biotechnol. Biochem., 66:2362-2366.

Fujimori et al., "The genus *Bifidobacterium* for cancer gene therapy," 2002, Curr. Opin. Drug Discov. Devel., 5:200-203.

Tanaka et al., "Structural and functional analysis of pTB6 from *Bifidobacterium longum*," 2005, Biosci. Biotechnol. Biochem., 69:422-425.

Argnani et al., "A convenient and reproducible method to genetically transform bacteria of the genus *Bifidobacterium*," 1996, Microbiology, 142:109-114.

* cited by examiner

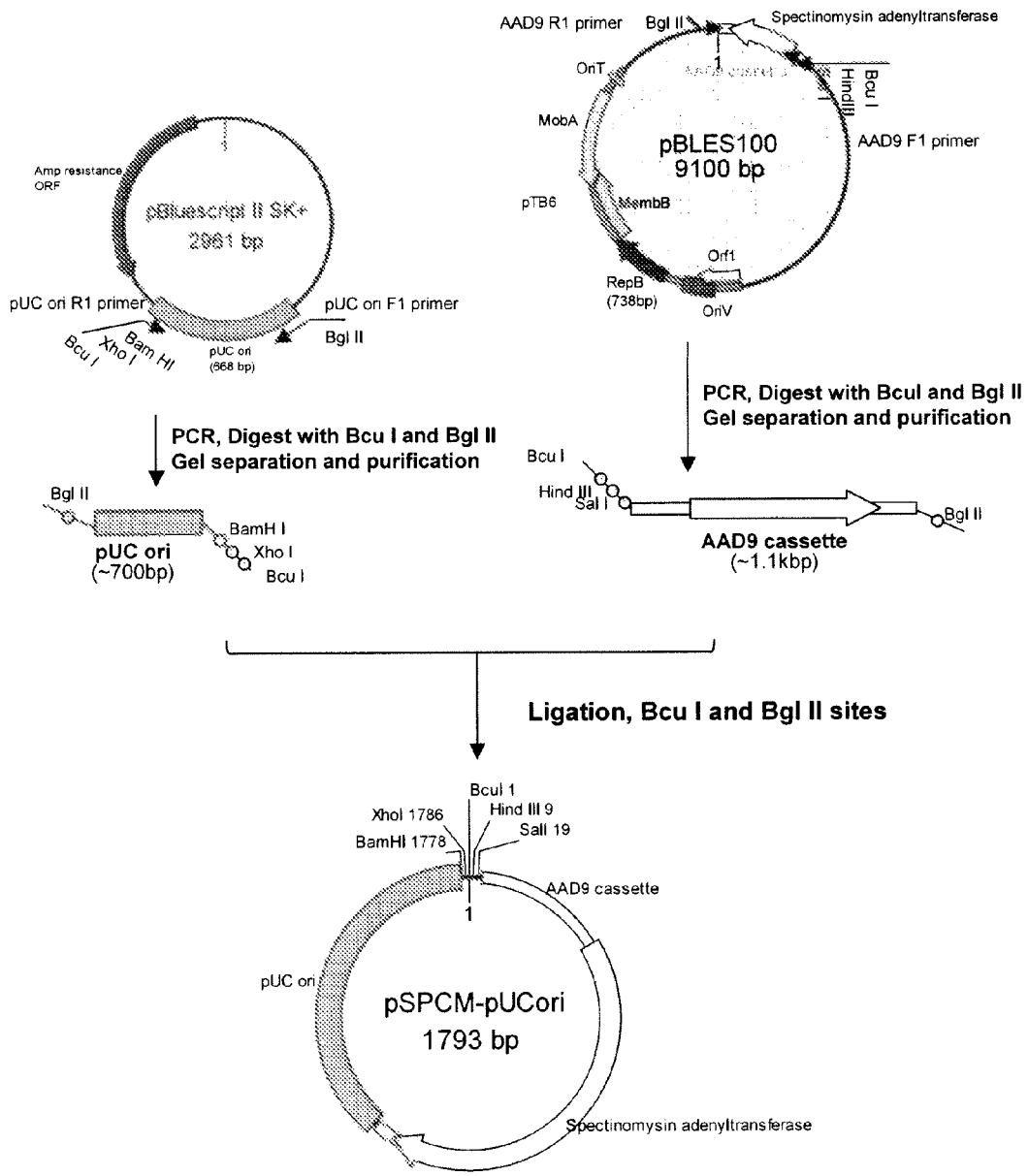
Fig.1 Constructing process of selective marker plasmid(pSPCM-pUCori)
(step1)

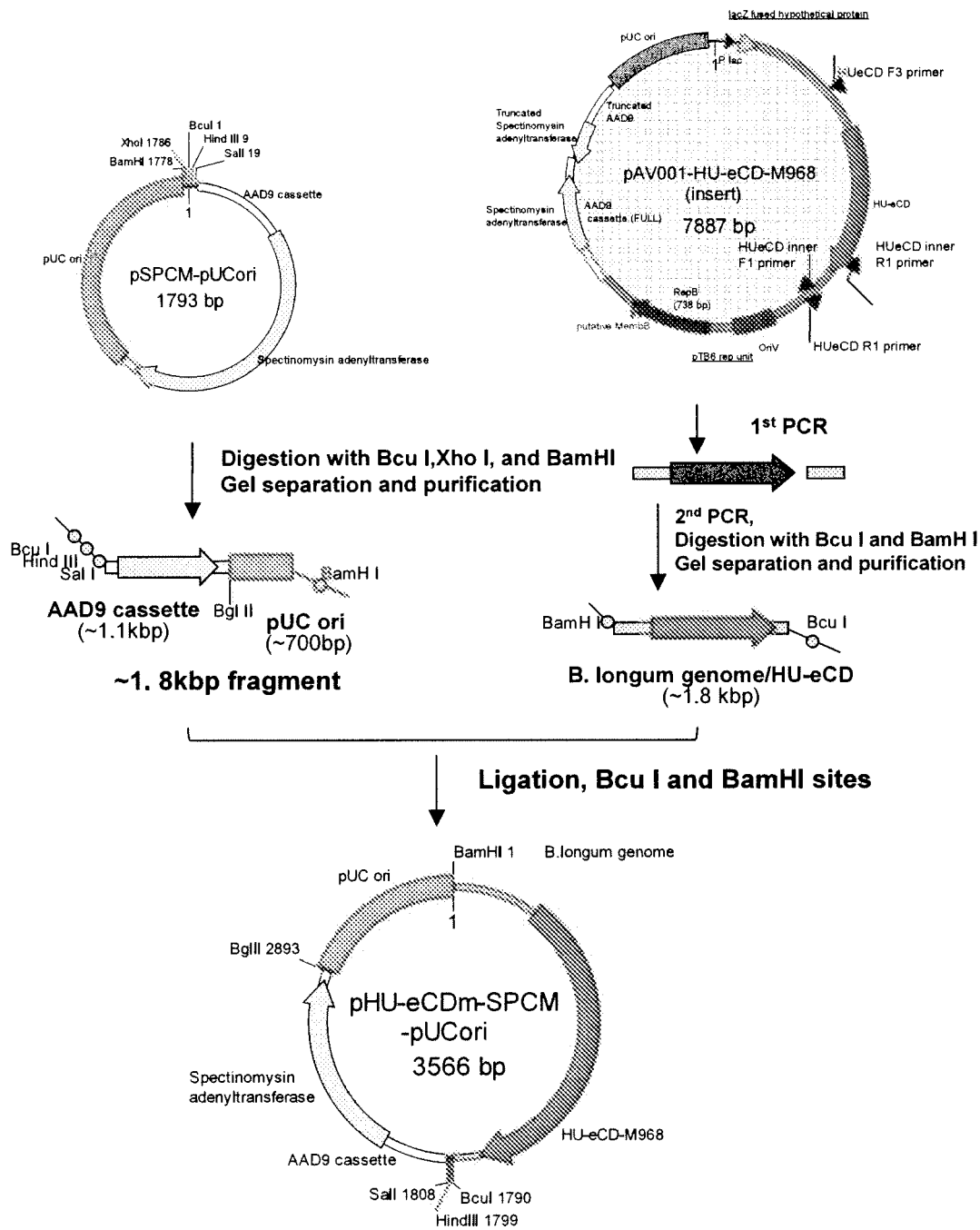
Fig. 2 Construction process of selective marker/active protein plasmid (pHU-eCDm-SPCM-pUCori) (step 2)

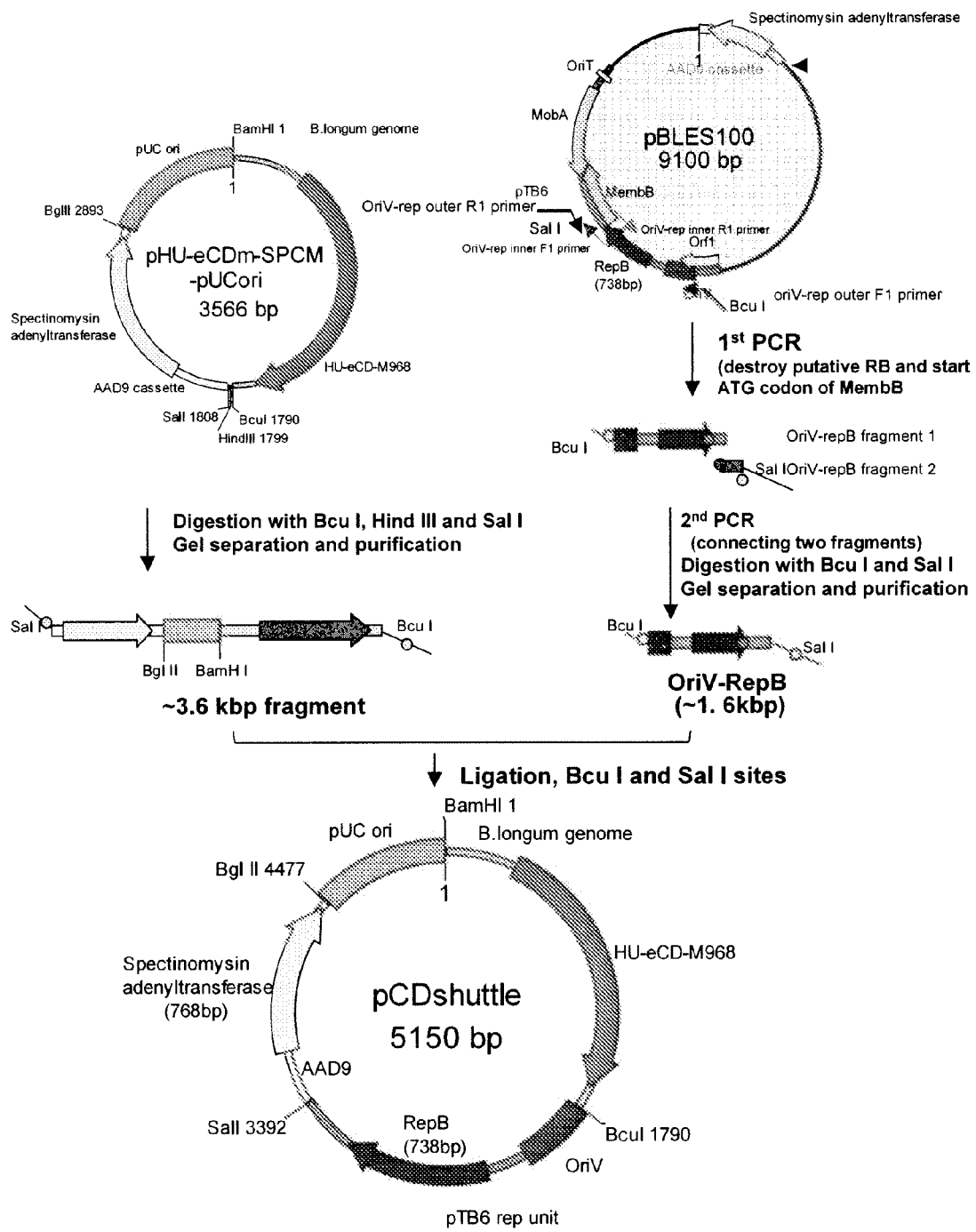
Fig. 3 Construction process of shuttle plasmid (pCDshuttle)(step 3)

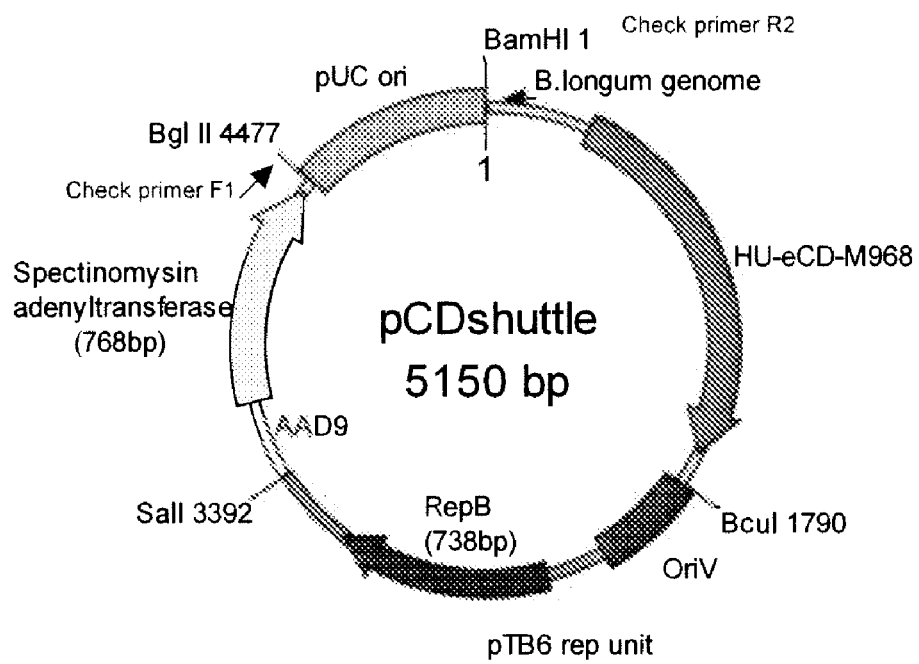
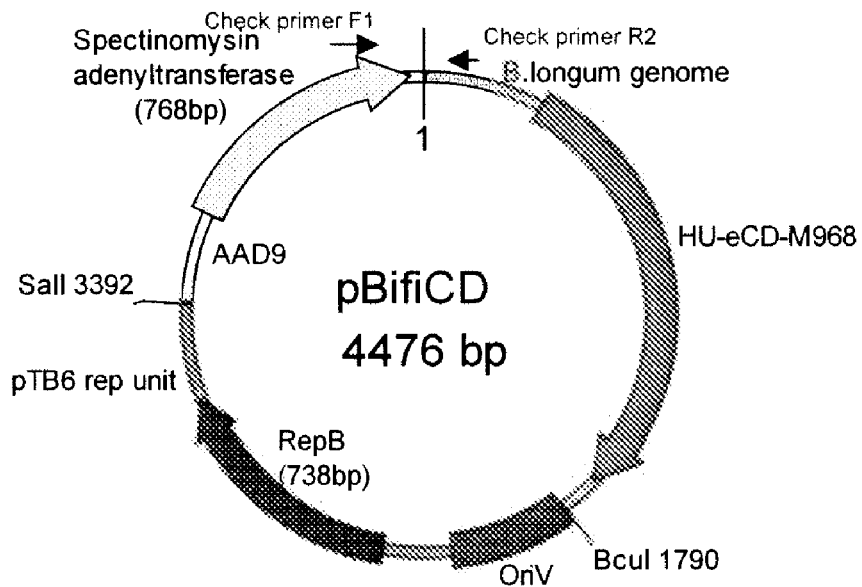
Fig. 4 Construction process of "pBifiCD" (step4)

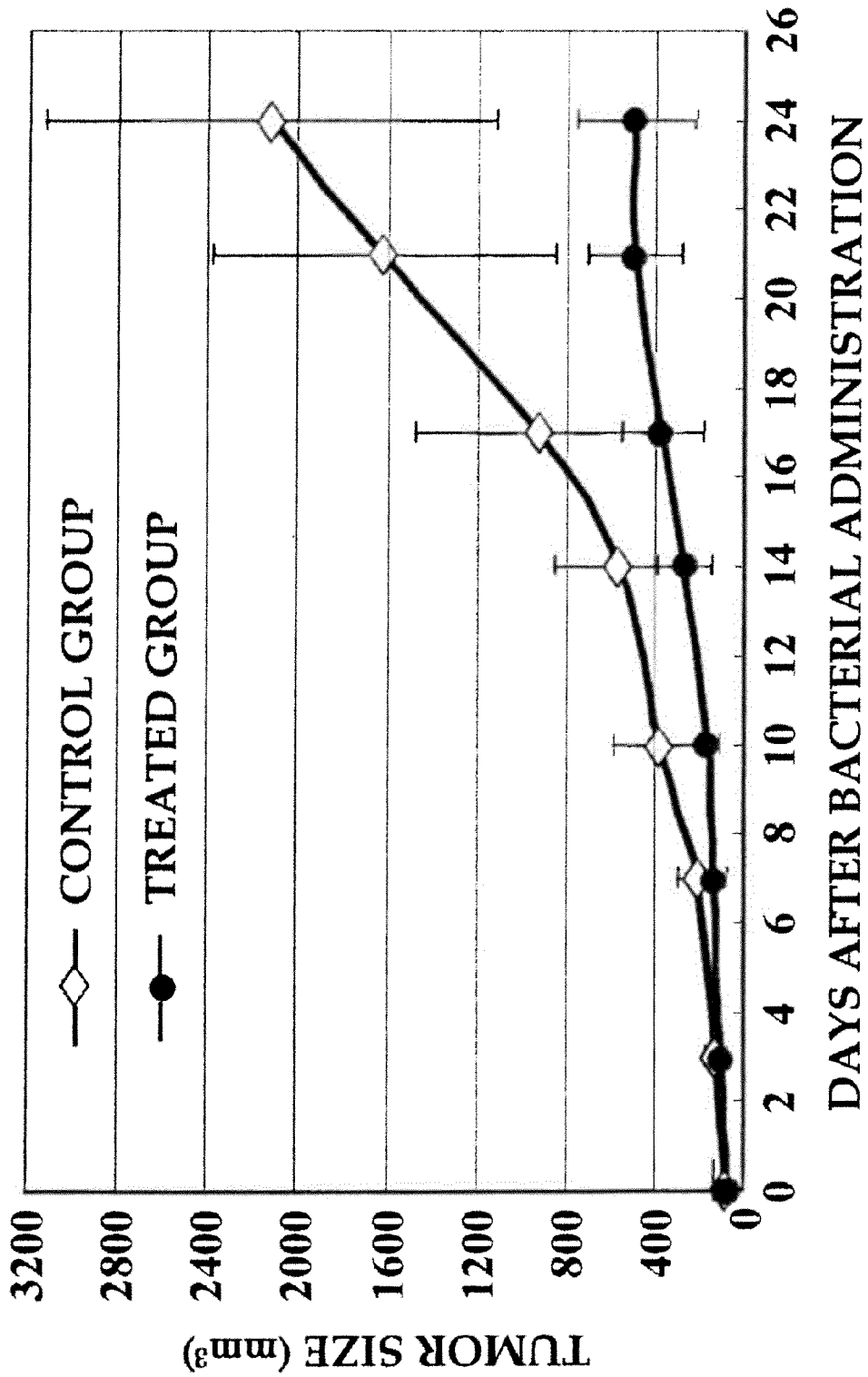
Fig. 5 Anti-tumor effect of B.longum Re-105A/pBifiCD cloning strain

SEQUENCE LISTING

```
<160> NUMBER OF SEQ ID NOS: 43

<210> SEQ ID NO 1
<211> LENGTH: 1793
<212> TYPE: DNA
<213> ORGANISM: Artificial
<220> FEATURE:
<223> OTHER INFORMATION: plasmid pSPCM-pUCori

<400> SEQUENCE: 1
actagtagaa agcttagagt cgactcgatt ttcgttcgtg aatacatgtt ataataacta      60
taactaataa cgtaacgtga ctggcaagag atatttttaa aacaatgaat aggtttacac     120
ttactttagt tttatggaaa tgaaagatca tatcatatat aatctagaat aaaattaact     180
aaaataatta ttatctagat aaaaaattta gaagccaatg aaatctataa ataaactaaa     240
ttaagtttat ttaattaaca actatggata taaaataggt actaatcaaa atagtgagga     300
ggatatattt gaatacatac gaacaaatta ataaagtgaa aaaaatactt cggaaacatt     360
taaaaaataa ccttattggt acttacatgt ttggatcagg agttgagagt ggactaaaac     420
caaatagtga tcttgacttt ttagtcgtcg tatctgaacc attgacagat caaagtaaag     480
aaatacttat acaaaaaatt agacctattt caaaaaaaat aggagataaa agcaacttac     540
gatatattga attaacaatt attattcagc aagaaatggt accgtggaat catcctccca     600
aacaagaatt tatttatgga gaatggttac aagagcttta tgaacaagga tacattcctc     660
agaaggaatt aaattcagat ttaaccataa tgctttacca agcaaaacga aaaaataaaa     720
gaatatacgg aaattatgac ttagaggaat tactacctga tattccattt tctgatgtga     780
gaagagccat tatggattcg tcagaggaat taatagataa ttatcaggat gatgaaacca     840
actctatatt aactttatgc cgtatgattt taactatgga cacgggtaaa atcataccaa     900
aagatattgc gggaaatgca gtggctgaat cttctccatt agaacatagg gagagaattt     960
tgttagcagt tcgtagttat cttggagaga atattgaatg gactaatgaa aatgtaaatt    1020
taactataaa ctatttaaat aacagattaa aaaaattata aaaaaattga aaaatggtg    1080 gaaacacttt tttcaatttt tttagatctt gagcaaaagg ccagcaaaag gccaggaacc    1140
gtaaaaaggc cgcgttgctg gcgtttttcc ataggctccg ccccccctgac gagcatcaca    1200 aaaatcgacg ctcaagtcag aggtggcgaa acccgacagg actataaaga taccaggcgt    1260
ttccccctgg aagctccctc gtgcgctctc ctgttccgac cctgccgctt accggatacc    1320
tgtccgcctt tctcccttcg ggaagcgtgg cgctttctca tagctcacgc tgtaggtatc    1380
tcagttcggt gtaggtcgtt cgctccaagc tgggctgtgt gcacgaaccc cccgttcagc    1440
ccgaccgctg cgccttatcc ggtaactatc gtcttgagtc aacccggta agacacgact    1500 tatcgccact ggcagcagcc actggtaaca ggattagcag agcgaggtat gtaggcggtg    1560
ctacagagtt cttgaagtgg tggcctaact acggctacac tagaagaaca gtatttggta    1620
tctgcgctct gctgaagcca gttaccttcg gaaaaagagt tggtagctct tgatccggca    1680
aacaaaccac cgctggtagc ggtggttttt ttgtttgcaa gcagcagatt acgcgcagaa    1740
aaaaaggatc tcaagaagat cctttgatct tttctacgga tccttctcga gtc           1793
```

<210> SEQ ID NO 2
<211> LENGTH: 3566
<212> TYPE: DNA
<213> ORGANISM: Artificial
<220> FEATURE:
<223> OTHER INFORMATION: plasmid pHU-eCDm-SPCM-pUCori

<400> SEQUENCE: 2

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg      300
ctagtatcat tgatgacaac atggactaag caaaagtgct tgtcccctga cccaagaagg     360
atgctttatg gcatacaaca gtctgacct cgtttcgaat aacgctttac aaacaattat      420
taacgcccgg ttaccaggcg aagagggct gtggcagatt catctgcagg acggaaaaat      480
cagcgccatt gatgcgcaat ccggcgtgat gcccataact gaaaacagcc tggatgccga     540
acaaggttta gttataccgc cgtttgtgga gccacatatt cacctggaca ccacgcaaac     600
cgccggacaa ccgaactgga atcagtccgg cacgctgttt gaaggcattg aacgctgggc     660
cgagcgcaaa gcgttattaa cccatgacga tgtgaaacaa cgcgcatggc aaacgctgaa     720
atggcagatt ccaacggca ttcagcatgt gcgtacccat gtcgatgttt cggatgcaac     780
gctaactgcg ctgaaagcaa tgctggaagt gaagcaggaa gtcgcgccgt ggattgatct     840
gcaaatcgtc gccttccctc aggaagggat tttgtcgtat cccaacggtg aagcgttgct     900
ggaagaggcg ttacgcttag ggcagatgt agtggggcg attccgcatt ttgaatttac      960
ccgtgaatac ggcgtggagt cgctgcataa aaccttcgcc ctggcgcaaa aatacgaccg    1020
tctcatcgac gttcactgtg atgagatcga tgacgagcag tcgcgctttg tcgaaaccgt    1080
tgctgccctg gcgcaccatg aaggcatggg cgcgcgagtc accgccagcc acaccacggc    1140
aatgcactcc tataacgggg cgtataccta cgcctgttc cgcttgctga aaatgtccgg     1200
tattaacttt gtcgccaacc cgctggtcaa tattcatctg caaggacgtt tcgatacgta    1260
tccaaaacgt cgcggcatca cgcgcgttaa agagatgctg gagtccggca ttaacgtctg    1320
ctttggtcac gatgctgtct tcgatccgt ggtatccgct ggaacggcga atatgctgca    1380
agtgctgcat atggggctgc atgtttgcca gttgatgggc tacgggcaga ttaacgatgg    1440
cctgaattta atcacccacc acagcgcaag gacgttgaat ttgcaggatt acggcattgc    1500
cgccggaaac agcgccaacc tgattatcct gccggctgaa aatgggtttg atgcgctgcg    1560
ccgtcaggtt ccggtacgtt attcggtacg tggcggcaag gtgattgcca gcacacaacc    1620
ggcacaaacc accgtatatc tggagcagcc agaagccatc gattacaaac gttgaccttc    1680
tgctcgtagc gattacttcg agcattactg acgacaaaga ccccgaccga gatggtcggg    1740
gtctttttgt tgtggtgctg tgacgtgttg tccaaccgta ttattccgga ctagtagaaa    1800
gcttagagtc gactcgattt tcgttcgtga atacatgtta taataactat aactaataac    1860
gtaacgtgac tggcaagaga tatttttaaa acaatgaata ggtttacact tactttagtt    1920
ttatggaaat gaaagatcat atcatatata atctagaata aaattaacta aataattat    1980
tatctagata aaaatttag aagccaatga atctataaa taaactaaat taagtttatt      2040
taattaacaa ctatggatat aaaataggta ctaatcaaaa tagtgaggag gatatatttg    2100
```

| | |
|---|---|
| aatacatacg aacaaattaa taaagtgaaa aaaatacttc ggaaacattt aaaaaataac | 2160 |
| cttattggta cttacatgtt tggatcagga gttgagagtg gactaaaacc aaatagtgat | 2220 |
| cttgactttt tagtcgtcgt atctgaacca ttgacagatc aaagtaaaga aatacttata | 2280 |
| caaaaaatta gacctatttc aaaaaaaata ggagataaaa gcaacttacg atatattgaa | 2340 |
| ttaacaatta ttattcagca agaaatggta ccgtggaatc atcctcccaa acaagaattt | 2400 |
| atttatggag aatggttaca agagctttat gaacaaggat acattcctca gaaggaatta | 2460 |
| aattcagatt taaccataat gctttaccaa gcaaaacgaa aaaataaaag aatatacgga | 2520 |
| aattatgact tagaggaatt actacctgat attccatttt ctgatgtgag aagagccatt | 2580 |
| atggattcgt cagaggaatt aatagataat tatcaggatg atgaaaccaa ctctatatta | 2640 |
| actttatgcc gtatgatttt aactatggac acgggtaaaa tcataccaaa agatattgcg | 2700 |
| ggaaatgcag tggctgaatc ttctccatta gaacataggg agagaatttt gttagcagtt | 2760 |
| cgtagttatc ttggagagaa tattgaatgg actaatgaaa atgtaaattt aactataaac | 2820 |
| tatttaaata acagattaaa aaaattaaa aaaaattgaa aaaatggtgg aaacacttt | 2880 |
| ttcaattttt ttagatcttg agcaaaaggc cagcaaaagg ccaggaaccg taaaaaggcc | 2940 |
| gcgttgctgg cgtttttcca taggctccgc cccctgacg agcatcacaa aaatcgacgc | 3000 |
| tcaagtcaga ggtggcgaaa cccgacagga ctataaagat accaggcgtt ccccctgga | 3060 |
| agctccctcg tgcgctctcc tgttccgacc ctgccgctta ccggatacct gtccgccttt | 3120 |
| ctcccttcgg gaagcgtggc gctttctcat agctcacgct gtaggtatct cagttcggtg | 3180 |
| taggtcgttc gctccaagct gggctgtgtg cacgaacccc ccgttcagcc cgaccgctgc | 3240 |
| gccttatccg gtaactatcg tcttgagtcc aacccggtaa gacacgactt atcgccactg | 3300 |
| gcagcagcca ctggtaacag gattagcaga gcgaggtatg taggcggtgc tacagagttc | 3360 |
| ttgaagtggt ggcctaacta cggctacact agaagaacag tatttggtat ctgcgctctg | 3420 |
| ctgaagccag ttaccttcgg aaaaagagtt ggtagctctt gatccggcaa acaaaccacc | 3480 |
| gctggtagcg gtggtttttt tgtttgcaag cagcagatta cgcgcagaaa aaaggatct | 3540 |
| caagaagatc ctttgatctt ttctac | 3566 |

<210> SEQ ID NO 3
<211> LENGTH: 5150
<212> TYPE: DNA
<213> ORGANISM: Artificial
<220> FEATURE:
<223> OTHER INFORMATION: shuttle plasmid pCDshuttle

<400> SEQUENCE: 3

| | |
|---|---|
| ggatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| ccctttcgggg aaatagatgt gaaaacccctt ataaacgcg ggttttcgca gaaacatgcg | 300 |
| ctagtatcat tgatgacaac atggactaag caaaagtgct tgtcccctga cccaagaagg | 360 |
| atgctttatg gcatacaaca agtctgacct cgtttcgaat aacgctttac aaacaattat | 420 |
| taacgcccgg ttaccaggcg aagaggggct gtggcagatt catctgcagg acggaaaaat | 480 |
| cagcgccatt gatgcgcaat ccggcgtgat gcccataact gaaaacagcc tggatgccga | 540 |
| acaaggttta gttataccgc cgtttgtgga gccacatatt cacctggaca ccacgcaaac | 600 |

```
cgccggacaa ccgaactgga atcagtccgg cacgctgttt gaaggcattg aacgctgggc    660
cgagcgcaaa gcgttattaa cccatgacga tgtgaaacaa cgcgcatggc aaacgctgaa    720
atggcagatt gccaacggca ttcagcatgt gcgtacccat gtcgatgttt cggatgcaac    780
gctaactgcg ctgaaagcaa tgctggaagt gaagcaggaa gtcgcgccgt ggattgatct    840
gcaaatcgtc gccttccctc aggaagggat tttgtcgtat cccaacggtg aagcgttgct    900
ggaagaggcg ttacgcttag gggcagatgt agtgggggcg attccgcatt ttgaatttac    960
ccgtgaatac ggcgtggagt cgctgcataa aaccttcgcc ctggcgcaaa aatacgaccg   1020
tctcatcgac gttcactgtg atgagatcga tgacgagcag tcgcgctttg tcgaaaccgt   1080
tgctgccctg gcgcaccatg aaggcatggg cgcgcgagtc accgccagcc acaccacggc   1140
aatgcactcc tataacgggg cgtataccte acgcctgttc cgcttgctga aaatgtccgg   1200
tattaacttt gtcgccaacc cgctggtcaa tattcatctg caaggacgtt tcgatacgta   1260
tccaaaacgt cgcggcatca cgcgcgttaa agagatgctg gagtccggca ttaacgtctg   1320 cttttggtcac gatgctgtct tcgatccgtg gtatccgctg gaacggcga atatgctgca   1380 agtgctgcat atgggctgc atgtttgcca gttgatgggc tacgggcaga ttaacgatgg   1440
cctgaattta atcacccacc acagcgcaag gacgttgaat ttgcaggatt acggcattgc   1500
cgccggaaac agcgccaacc tgattatcct gccggctgaa aatgggtttg atgcgctgcg   1560
ccgtcaggtt ccggtacgtt attcggtacg tggcggcaag gtgattgcca gcacacaacc   1620
ggcacaaacc accgtatatc tggagcagcc agaagccatc gattacaaac gttgaccttc   1680
tgctcgtagc gattacttcg agcattactg acgacaaaga ccccgaccga gatggtcggg   1740 gtcttttgt tgtggtgctg tgacgtgttg tccaaccgta ttattccgga ctagtcctcc   1800
aggacctcgt ctacgaggcg ctgagcgagg aatggcgcaa aagggacggc gagatcagcg   1860
acccatgggc caacgacgag gcggacggat accagccgcc ctcatacgag ccggtcaacc   1920
ccgaacgcag gactccccag acgccctccg atggcctgat ctgacgtccg aaaaaaggcg   1980
ctgtgcgccc tttttaaatc tttttataaat cttttttacat tcttttagcc cctccgcagc   2040
cttactctcc caacgggttt cagccgaaac ctacaccaaa aggggagcga acctacacca   2100
aaaggggagc gaacctacac caaaagggga gcgaacctac accaaaaggg gagctatata   2160
caccttttgt tatttaaggt gcaagttgtg ctatgctgag gccatgtcca atgagatcgt   2220
gaagttcagc aaccagttca acaacgtcgc gctgaagaag ttcgacgccg tgcacctgga   2280
cgtgctcatg gcgatcgcct caagggtgag ggagaagggc acggccacgg tggagttctc   2340
gttcgaggag ctgcgcggcc tcatgcgatt gaggaagaac ctgaccaaca agcagctggc   2400
cgacaagatc gtgcagacga acgcgcgcct gctggcgctg aactacatgt cgaggattc   2460 gggcaagatc atccagttcg cgctgttcac gaagttcgtc accgacccgc aggaggcgac   2520
tctcgcggtt ggggtcaacg aggagttcgc gttcctgctc aacgacctga ccagccagtt   2580
cacgcgcttc gagctggccg agttcgccga cctcaagagc aagtacgcca aggagttcta   2640
ccgcagggcc aagcagtacc gcagctccgg aatctggaag atcggccgcg acgagttctg   2700
ccgactgctt ggcgttccac cgtcggcaat aacccagaca cgatatctga atcagaaggt   2760
tcttcagcca attcaggagg agtgtgggcc tctccttggc ctgaagatcg agcgccagta   2820
cgtgaaacgc aggctgtcgg gcttcgtgtt cacattcgcc cgcgagaccc ctccggtgat   2880
cgacgccagg cccgtggagg cgaggaagac ggacggcgac ggcaagggcc attggacgag   2940
cgttgccggg tacggcgagg tgttcacgac cacggcgttg ttcgacgtga cggccgcccg   3000
```

-continued

```
ggctcacttc gacggcaccg ttgaagccgg ggagtgccgt ttctgcgcgt ttgacgcgcg    3060
caaccgcgaa catcatgcgc ggaacgccgg aaggctgttc tagcggccgt gtccgcgcct    3120
ctggggcggt tgcgcctgcc atgggtcgat ctgccgctgt tcggcctcac gctggtctgt    3180
gcgctgcctg atctccctga gcaggtcggc cttggtcctg ggggcgcttc gctcctcgaa    3240
cgggccgctc tcccccaggt cctcgggctc gctcaggtcc aacggctcgt caccggacgg    3300
ctcgggccgg ttctctccct gtgccgggtt ctccgcctgt gcgcgttgtt cggccatgcg    3360
cagtgcgagg gccttcacct gttcggggct tgtcgactcg atttcgttc gtgaatacat    3420 gttataataa ctataactaa taacgtaacg tgactggcaa gagatatttt taaaacaatg    3480
aataggttta cacttacttt agttttatgg aaatgaaaga tcatatcata tataatctag    3540
aataaaatta actaaaataa ttattatcta gataaaaaat ttagaagcca atgaaatcta    3600
taaataaact aaattaagtt tatttaatta acaactatgg atataaaata ggtactaatc    3660
aaaatagtga ggaggatata tttgaataca tacgaacaaa ttaataaagt gaaaaaaata    3720
cttcggaaac atttaaaaaa taaccttatt ggtacttaca tgtttggatc aggagttgag    3780
agtggactaa aaccaaatag tgatcttgac ttttagtcg tcgtatctga accattgaca    3840
gatcaaagta aagaaatact tatacaaaaa attagaccta tttcaaaaaa aataggagat    3900
aaaagcaact tacgatatat tgaattaaca attattattc agcaagaaat ggtaccgtgg    3960
aatcatcctc ccaaacaaga atttatttat ggagaatggt tacaagagct ttatgaacaa    4020
ggatacattc tcagaagga attaaattca gatttaacca taatgcttta ccaagcaaaa    4080
cgaaaaaata aagaatata cggaaattat gacttagagg aattactacc tgatattcca    4140
ttttctgatg tgagaagagc cattatggat tcgtcagagg aattaataga taattatcag    4200
gatgatgaaa ccaactctat attaacttta tgccgtatga ttttaactat ggacacgggt    4260
aaaatcatac caaagatat tgcgggaaat gcagtggctg aatcttctcc attagaacat    4320
agggagagaa ttttgttagc agttcgtagt tatcttggag agaatattga atggactaat    4380
gaaaatgtaa atttaactat aaactattta aataacagat taaaaaaatt ataaaaaaat    4440
tgaaaaaatg gtggaaacac tttttttcaat tttttttagat cttgagcaaa aggccagcaa    4500
aaggccagga accgtaaaaa ggccgcgttg ctggcgtttt tccataggct ccgcccccct    4560
gacgagcatc acaaaaatcg acgctcaagt cagaggtggc gaaacccgac aggactataa    4620
agataccagg cgtttccccc tggaagctcc ctcgtgcgct ctcctgttcc gaccctgccg    4680
cttaccggat acctgtccgc ctttctccct tcgggaagcg tggcgctttc tcatagctca    4740
cgctgtaggt atctcagttc ggtgtaggtc gttcgctcca agctgggctg tgtgcacgaa    4800
ccccccgttc agcccgaccg ctgcgcctta tccggtaact atcgtcttga gtccaacccg    4860
gtaagacacg acttatcgcc actggcagca gccactggta acaggattag cagagcgagg    4920
tatgtaggcg gtgctacaga gttcttgaag tggtggccta actacggcta cactagaaga    4980
acagtatttg gtatctgcgc tctgctgaag ccagttacct tcggaaaaag agttggtagc    5040
tcttgatccg gcaaacaaac caccgctggt agcggtggtt ttttgtttg caagcagcag    5100 attacgcgca gaaaaaaagg atctcaagaa gatcctttga tcttttctac                5150
```

<210> SEQ ID NO 4
<211> LENGTH: 4476
<212> TYPE: DNA
<213> ORGANISM: Artificial
<220> FEATURE:
<223> OTHER INFORMATION: plasmid pBifiCD

```
<400> SEQUENCE: 4
agatccgtct tcctgctggc ctatgcattg ggttccgcag tgcccactcc aggcggtctg    60
ggcggtgtgg aagcggcgct gacattcgcg ttcgtggcgg tcggagtgcc gcagggcgtg   120
gcgctttccg ccactttgct gcaccgcgtg gtgttctact ggctgcgcat tccgctgggc   180
gcggcggcca tgaagtggct tgacaagcat aatcttgtct gattcgtcta ttttcatacc   240
cccttcgggg aaatagatgt gaaaacccct ataaaacgcg ggttttcgca gaaacatgcg   300
ctagtatcat tgatgacaac atggactaag caaaagtgct tgtccccctga cccaagaagg   360 atgctttatg gcatacaaca agtctgacct cgtttcgaat aacgctttac aaacaattat   420
taacgcccgg ttaccaggcg aagagggggct gtggcagatt catctgcagg acggaaaaat   480
cagcgccatt gatgcgcaat ccggcgtgat gcccataact gaaaacagcc tggatgccga   540
acaaggttta gttataccgc cgtttgtgga gccacatatt cacctggaca ccacgcaaac   600
cgccggacaa ccgaactgga atcagtccgg cacgctgttt gaaggcattg aacgctgggc   660
cgagcgcaaa gcgttattaa cccatgacga tgtgaaacaa cgcgcatggc aaacgctgaa   720
atggcagatt gccaacggca ttcagcatgt gcgtacccat gtcgatgttt cggatgcaac   780
gctaactgcg ctgaaagcaa tgctggaagt gaagcaggaa gtcgcgccgt ggattgatct   840
gcaaatcgtc gccttccctc aggaagggat tttgtcgtat cccaacggtg aagcgttgct   900
ggaagaggcg ttacgcttag gggcagatgt agtgggggcg attccgcatt ttgaatttac   960
ccgtgaatac ggcgtggagt cgctgcataa aaccttcgcc ctggcgcaaa aatacgaccg  1020
tctcatcgac gttcactgtg atgagatcga tgacgagcag tcgcgctttg tcgaaaccgt  1080
tgctgccctg gcgcaccatg aaggcatggg cgcgcgagtc accgccagcc acaccacggc  1140
aatgcactcc tataacgggg cgtataccctc acgcctgttc cgcttgctga aaatgtccgg  1200
tattaacttt gtcgccaacc cgctggtcaa tattcatctg caaggacgtt tcgatacgta  1260
tccaaaacgt cgcggcatca cgcgcgttaa agagatgctg gagtccggca ttaacgtctg  1320 cttttggtcac gatgctgtct tcgatccgtg gtatccgctg gaacggcga atatgctgca  1380 agtgctgcat atggggctgc atgtttgcca gttgatgggc tacgggcaga ttaacgatgg  1440
cctgaattta atcacccacc acagcgcaag gacgttgaat ttgcaggatt acggcattgc  1500
cgccggaaac agcgccaacc tgattatcct gccggctgaa aatgggtttg atgcgctgcg  1560
ccgtcaggtt ccggtacgtt attcggtacg tggcggcaag gtgattgcca gcacacaacc  1620
ggcacaaacc accgtatatc tggagcagcc agaagccatc gattacaaac gttgaccttc  1680
tgctcgtagc gattacttcg agcattactg acgacaaaga ccccgaccga gatggtcggg  1740
gtctttttgt tgtggtgctg tgacgtgttg tccaaccgta ttattccgga ctagtcctcc  1800
aggacctcgt ctacgaggcg ctgagcgagg aatggcgcaa aagggacggc gagatcagcg  1860
acccatgggc caacgacgag gcggacggat accagccgcc ctcatacgag ccggtcaacc  1920
ccgaacgcag gactcccag acgccctccg atggcctgat ctgacgtccg aaaaaaggcg  1980
ctgtgcgccc ttttaaatc ttttataaat cttttttacat tcttttagcc cctccgcagc  2040
cttactctcc caacgggttt cagccgaaac ctacaccaaa aggggagcga acctacacca  2100 aaagggagc gaacctacac caaaagggga gcgaacctac accaaaaggg gagctatata  2160 cacctttgt tatttaaggt gcaagttgtg ctatgctgag gccatgtcca atgagatcgt  2220
gaagttcagc aaccagttca acaacgtcgc gctgaagaag ttcgacgccg tgcacctgga  2280
cgtgctcatg gcgatcgcct caagggtgag ggagaagggc acggccacgg tggagttctc  2340
```

```
gttcgaggag ctgcgcggcc tcatgcgatt gaggaagaac ctgaccaaca agcagctggc   2400
cgacaagatc gtgcagacga acgcgcgcct gctggcgctg aactacatgt tcgaggattc   2460
gggcaagatc atccagttcg cgctgttcac gaagttcgtc accgacccgc aggaggcgac   2520
tctcgcggtt ggggtcaacg aggagttcgc gttcctgctc aacgacctga ccagccagtt   2580
cacgcgcttc gagctggccg agttcgccga cctcaagagc aagtacgcca aggagttcta   2640
ccgcagggcc aagcagtacc gcagctccgg aatctggaag atcggccgcg acgagttctg   2700
ccgactgctt ggcgttccac cgtcggcaat aacccagaca cgatatctga atcagaaggt   2760
tcttcagcca attcaggagg agtgtgggcc tctccttggc ctgaagatcg agcgccagta   2820
cgtgaaacgc aggctgtcgg gcttcgtgtt cacattcgcc cgcgagaccc ctccggtgat   2880
cgacgccagg cccgtggagg cgaggaagac ggacggcgac ggcaagggcc attggacgag   2940
cgttgccggg tacggcgagg tgttcacgac cacggcgttg ttcgacgtga cggccgcccg   3000
ggctcacttc gacggcaccg ttgaagccgg ggagtgccgt ttctgcgcgt ttgacgcgcg   3060
caaccgcgaa catcatgcgc ggaacgccgg aaggctgttc tagcggccgt gtccgcgcct   3120
ctggggcggt tgcgcctgcc atgggtcgat ctgccgctgt tcggcctcac gctggtctgt   3180
gcgctgcctg atctccctga gcaggtcggc cttggtcctg ggggcgcttc gctcctcgaa   3240
cgggccgctc tcccccaggt cctcgggctc gctcaggtcc aacggctcgt caccggacgg   3300
ctcgggccgg ttctctccct gtgccgggtt ctccgcctgt gcgcgttgtt cggccatgcg   3360
cagtgcgagg gccttcacct gttcggggct tgtcgactcg attttcgttc gtgaatacat   3420
gttataataa ctataactaa taacgtaacg tgactggcaa gagatatttt taaaacaatg   3480
aataggttta cacttacttt agttttatgg aaatgaaaga tcatatcata tataatctag   3540
aataaaatta actaaaataa ttattatcta gataaaaaat ttagaagcca atgaaatcta   3600
taaataaact aaattaagtt tatttaatta acaactatgg atataaaata ggtactaatc   3660
aaaatagtga ggaggatata tttgaataca tacgaacaaa ttaataaagt gaaaaaaata   3720
cttcggaaac atttaaaaaa taaccttatt ggtacttaca tgtttggatc aggagttgag   3780
agtggactaa aaccaaatag tgatcttgac ttttttagtcg tcgtatctga accattgaca   3840
gatcaaagta aagaaatact tatacaaaaa attagaccta tttcaaaaaa aataggagat   3900
aaaagcaact tacgatatat tgaattaaca attattattc agcaagaaat ggtaccgtgg   3960
aatcatcctc ccaaacaaga atttatttat ggagaatggt tacaagagct ttatgaacaa   4020
ggatacattc ctcagaagga attaaattca gatttaacca taatgcttta ccaagcaaaa   4080
cgaaaaaata aaagaatata cggaaattat gacttagagg aattactacc tgatattcca   4140
ttttctgatg tgagaagagc cattatggat tcgtcagagg aattaataga taattatcag   4200
gatgatgaaa ccaactctat attaacttta tgccgtatga ttttaactat ggacacgggt   4260
aaaatcatac caaaagatat tgcgggaaat gcagtggctg aatcttctcc attagaacat   4320
agggagagaa ttttgttagc agttcgtagt tatcttggag agaatattga atggactaat   4380 gaaatgtaa atttaactat aaactattta aataacagat taaaaaaatt ataaaaaaat   4440
tgaaaaaatg gtggaaacac ttttttcaat ttttt             4476
```

<210> SEQ ID NO 5
<211> LENGTH: 25
<212> TYPE: DNA
<213> ORGANISM: Artificial
<220> FEATURE:
<223> OTHER INFORMATION: forward primer for pUCori

```
<400> SEQUENCE: 5
agagagatct tgagcaaaag gccag                                              25

<210> SEQ ID NO 6
<211> LENGTH: 42
<212> TYPE: DNA
<213> ORGANISM: Artificial
<220> FEATURE:
<223> OTHER INFORMATION: reverse primer for pUCori

<400> SEQUENCE: 6
gagactagtg actcgagaag gatccgtaga aagatcaaa gg                            42

<210> SEQ ID NO 7
<211> LENGTH: 43
<212> TYPE: DNA
<213> ORGANISM: Artificial
<220> FEATURE:
<223> OTHER INFORMATION: forward primer for AAD9

<400> SEQUENCE: 7
agaactagta gaaagcttag agtcgactcg attttcgttc gtg                          43

<210> SEQ ID NO 8
<211> LENGTH: 36
<212> TYPE: DNA
<213> ORGANISM: Artificial
<220> FEATURE:
<223> OTHER INFORMATION: reverse primer for AAD9

<400> SEQUENCE: 8
gagagatcta aaaaattga aaaagtgtt tccacc                                    36

<210> SEQ ID NO 9
<211> LENGTH: 30
<212> TYPE: DNA
<213> ORGANISM: Artificial
<220> FEATURE:
<223> OTHER INFORMATION: forward primer for HUeCD

<400> SEQUENCE: 9
aagaggatcc gtcttcctgc tggcctatgc                                         30

<210> SEQ ID NO 10
<211> LENGTH: 29
<212> TYPE: DNA
<213> ORGANISM: Artificial
<220> FEATURE:
<223> OTHER INFORMATION: reverse primer for HUeCD

<400> SEQUENCE: 10
agaactagtc cggaataata cggttggac                                          29

<210> SEQ ID NO 11
<211> LENGTH: 35
<212> TYPE: DNA
<213> ORGANISM: Artificial
<220> FEATURE:
<223> OTHER INFORMATION: inner reverse primer for HUeCD

<400> SEQUENCE: 11
gctacgagca aaggtcaac gtttgtaatc gatgg                                    35

<210> SEQ ID NO 12
<211> LENGTH: 41
```

```
<212> TYPE: DNA
<213> ORGANISM: Artificial
<220> FEATURE:
<223> OTHER INFORMATION: inner forward primer for HUeCD

<400> SEQUENCE: 12
cgattacaaa cgttgacctt ctgctcgtag cgattacttc g                    41

<210> SEQ ID NO 13
<211> LENGTH: 29
<212> TYPE: DNA
<213> ORGANISM: Artificial
<220> FEATURE:
<223> OTHER INFORMATION: outer forward primer for OriV-Rep

<400> SEQUENCE: 13
agaactagtc ctccaggacc tcgtctacg                                  29

<210> SEQ ID NO 14
<211> LENGTH: 30
<212> TYPE: DNA
<213> ORGANISM: Artificial
<220> FEATURE:
<223> OTHER INFORMATION: outer reverse primer for OriV-Rep

<400> SEQUENCE: 14
agagtcgaca agccccgaac aggtgaaggc                                 30

<210> SEQ ID NO 15
<211> LENGTH: 38
<212> TYPE: DNA
<213> ORGANISM: Artificial
<220> FEATURE:
<223> OTHER INFORMATION: inner forward primer for OriV-Rep

<400> SEQUENCE: 15
ccgttgaagc cggggagtgc cgtttctgcg cgtttgac                        38

<210> SEQ ID NO 16
<211> LENGTH: 39
<212> TYPE: DNA
<213> ORGANISM: Artificial
<220> FEATURE:
<223> OTHER INFORMATION: inner reverse primer for OriV-Rep

<400> SEQUENCE: 16
gaaacggcac tccccggctt caacggtgcc gtcgaagtg                       39

<210> SEQ ID NO 17
<211> LENGTH: 23
<212> TYPE: DNA
<213> ORGANISM: Artificial
<220> FEATURE:
<223> OTHER INFORMATION: check primer forward

<400> SEQUENCE: 17
tgacttagag gaattactac ctg                                        23

<210> SEQ ID NO 18
<211> LENGTH: 20
<212> TYPE: DNA
<213> ORGANISM: Artificial
<220> FEATURE:
<223> OTHER INFORMATION: check primer reverse

<400> SEQUENCE: 18
aaagtggcgg aaagcgccac                                            20
```

```
<210> SEQ ID NO 19
<211> LENGTH: 20
<212> TYPE: DNA
<213> ORGANISM: Artificial
<220> FEATURE:
<223> OTHER INFORMATION: 37_R_5181

<400> SEQUENCE: 19
aaatatctct tgccagtcac                                              20

<210> SEQ ID NO 20
<211> LENGTH: 22
<212> TYPE: DNA
<213> ORGANISM: Artificial
<220> FEATURE:
<223> OTHER INFORMATION: 060723-spmsec(F)

<400> SEQUENCE: 20
catgtttgga tcaggagttg ag                                           22

<210> SEQ ID NO 21
<211> LENGTH: 20
<212> TYPE: DNA
<213> ORGANISM: Artificial
<220> FEATURE:
<223> OTHER INFORMATION: 41_F-seq13

<400> SEQUENCE: 21
agcaagaaat ggtaccgtgg                                              20

<210> SEQ ID NO 22
<211> LENGTH: 22
<212> TYPE: DNA
<213> ORGANISM: Artificial
<220> FEATURE:
<223> OTHER INFORMATION: 060219-pAV001-2

<400> SEQUENCE: 22
tttgcttggt aaagcattat gg                                           22

<210> SEQ ID NO 23
<211> LENGTH: 20
<212> TYPE: DNA
<213> ORGANISM: Artificial
<220> FEATURE:
<223> OTHER INFORMATION: 42_F-seq_28down

<400> SEQUENCE: 23
gacttagagg aattactacc                                              20

<210> SEQ ID NO 24
<211> LENGTH: 20
<212> TYPE: DNA
<213> ORGANISM: Artificial
<220> FEATURE:
<223> OTHER INFORMATION: 38_F_5980

<400> SEQUENCE: 24
ataccaaaag atattgcggg                                              20

<210> SEQ ID NO 25
<211> LENGTH: 22
<212> TYPE: DNA
<213> ORGANISM: Artificial
<220> FEATURE:
<223> OTHER INFORMATION: 060723-spmsec(R)
```

```
<400> SEQUENCE: 25
aatggagaag attcagccac tg                                              22

<210> SEQ ID NO 26
<211> LENGTH: 16
<212> TYPE: DNA
<213> ORGANISM: Artificial
<220> FEATURE:
<223> OTHER INFORMATION: pUC ori-1

<400> SEQUENCE: 26
aaggccagca aaaggc                                                     16

<210> SEQ ID NO 27
<211> LENGTH: 22
<212> TYPE: DNA
<213> ORGANISM: Artificial
<220> FEATURE:
<223> OTHER INFORMATION: 060219-pAV001-3(R)

<400> SEQUENCE: 27
gacgatagtt accggataag gc                                              22

<210> SEQ ID NO 28
<211> LENGTH: 22
<212> TYPE: DNA
<213> ORGANISM: Artificial
<220> FEATURE:
<223> OTHER INFORMATION: 060219-pAV001-3(F)

<400> SEQUENCE: 28
gccttatccg gtaactatcg tc                                              22

<210> SEQ ID NO 29
<211> LENGTH: 20
<212> TYPE: DNA
<213> ORGANISM: Artificial
<220> FEATURE:
<223> OTHER INFORMATION: 40_R-seq_16down

<400> SEQUENCE: 29
attagcagag cgaggtatgt                                                 20

<210> SEQ ID NO 30
<211> LENGTH: 20
<212> TYPE: DNA
<213> ORGANISM: Artificial
<220> FEATURE:
<223> OTHER INFORMATION: 39_R_6495

<400> SEQUENCE: 30
gcaagcagca gattacgcgc                                                 20

<210> SEQ ID NO 31
<211> LENGTH: 15
<212> TYPE: DNA
<213> ORGANISM: Artificial
<220> FEATURE:
<223> OTHER INFORMATION: HU IV (F)

<400> SEQUENCE: 31
agtgccgcag ggcgt                                                      15

<210> SEQ ID NO 32
<211> LENGTH: 15
```

-continued

```
<212> TYPE: DNA
<213> ORGANISM: Artificial
<220> FEATURE:
<223> OTHER INFORMATION: HU IV (R)

<400> SEQUENCE: 32
acgccctgcg gcact                                                          15

<210> SEQ ID NO 33
<211> LENGTH: 24
<212> TYPE: DNA
<213> ORGANISM: Artificial
<220> FEATURE:
<223> OTHER INFORMATION: 060403_HU upstream cloning

<400> SEQUENCE: 33
tttgcttagt ccatgttgtc atca                                                24

<210> SEQ ID NO 34
<211> LENGTH: 24
<212> TYPE: DNA
<213> ORGANISM: Artificial
<220> FEATURE:
<223> OTHER INFORMATION: pAVeCD1482_atg

<400> SEQUENCE: 34
atggcataca acaagtctga cctc                                                24

<210> SEQ ID NO 35
<211> LENGTH: 30
<212> TYPE: DNA
<213> ORGANISM: Artificial
<220> FEATURE:
<223> OTHER INFORMATION: CD seq (F)

<400> SEQUENCE: 35
gcgcatggca aacgctgaaa tggcagattg                                          30

<210> SEQ ID NO 36
<211> LENGTH: 30
<212> TYPE: DNA
<213> ORGANISM: Artificial
<220> FEATURE:
<223> OTHER INFORMATION: CD seq (R)

<400> SEQUENCE: 36
gtgatgccgc gacgttttgg atacgtatcg                                          30

<210> SEQ ID NO 37
<211> LENGTH: 22
<212> TYPE: DNA
<213> ORGANISM: Artificial
<220> FEATURE:
<223> OTHER INFORMATION: CD892_D314A

<400> SEQUENCE: 37
cgcgttaaag agatgctgga gt                                                  22

<210> SEQ ID NO 38
<211> LENGTH: 20
<212> TYPE: DNA
<213> ORGANISM: Artificial
<220> FEATURE:
<223> OTHER INFORMATION: R-pTB6 R7

<400> SEQUENCE: 38
gtctggggag tcctgcgttc                                                     20
```

```
<210> SEQ ID NO 39
<211> LENGTH: 25
<212> TYPE: DNA
<213> ORGANISM: Artificial
<220> FEATURE:
<223> OTHER INFORMATION: pBLES100 F3

<400> SEQUENCE: 39
tatgctgagg ccatgtccaa tgaga                                         25

<210> SEQ ID NO 40
<211> LENGTH: 21
<212> TYPE: DNA
<213> ORGANISM: Artificial
<220> FEATURE:
<223> OTHER INFORMATION: R-pTB6 R6

<400> SEQUENCE: 40
gtcaggtcgt tgagcaggaa c                                             21

<210> SEQ ID NO 41
<211> LENGTH: 24
<212> TYPE: DNA
<213> ORGANISM: Artificial
<220> FEATURE:
<223> OTHER INFORMATION: pTB6 F5 (pBLES100 F5)

<400> SEQUENCE: 41
gaagatcgag cgccagtacg tgaa                                          24

<210> SEQ ID NO 42
<211> LENGTH: 19
<212> TYPE: DNA
<213> ORGANISM: Artificial
<220> FEATURE:
<223> OTHER INFORMATION: 060219-pAV001-1

<400> SEQUENCE: 42
gtgaacacct cgccgtacc                                                19

<210> SEQ ID NO 43
<211> LENGTH: 20
<212> TYPE: DNA
<213> ORGANISM: Artificial
<220> FEATURE:
<223> OTHER INFORMATION: 36_F_4754

<400> SEQUENCE: 43
caaccgcgaa catcatgcgc                                               20
```

EXPRESSION VECTOR

This application claims and is entitled to priority of U.S. Provisional Patent Application No. 61/124,528, filed Apr. 17, 2008, the content of which is incorporated by reference herein in its entirety.

TECHNICAL FIELD

The present invention relates to an expression vector used in the construction of a transformant anaerobic microorganism useful as a gene transporter for anaerobic disease treatment, and a method for constructing the expression vector. Furthermore, the present invention relates to a gene transporter formed from an anaerobic microorganism transformed by the expression vector, a pharmaceutical composition that contains the gene transporter, and an anaerobic disease treatment agent that contains the gene transporter.

BACKGROUND

In the field of genetic engineering, phages, animal or plant viruses, plasmids, etc. are widely used as expression vectors for transforming microorganisms. As transformant microorganisms that are transformed and made to express a target protein of a gene product, E. Coli, yeast, etc. are widely used. These transformed microorganisms are aimed at expressing a target protein, and utilization of the microorganisms themselves is not contemplated.

In recent years, with regard to utilization of a transformed microorganism itself, a method for treating a malignant tumor has been attracting an attention in which a transformed anaerobic bacterium is used as a gene transporter; for example, a method of transporting a gene to a tumor site using transformed Clostridium (see e.g. Patent Publications 1 to 3) has been proposed and, furthermore, application of transformed Bifidobacterium longum to the treatment of solid tumors has been suggested (see e.g. Nonpatent Publications 1 and 2).

Furthermore, with regard to a transformed Bifidobacterium useful as a gene transporter for treatment of a solid tumor, it has been reported that Bifidobacterium longum transformed so as to express cytosine deaminase (hereinafter, called CD) can be expected to have an application in an enzyme-prodrug therapy (see e.g. Patent Publication 4 and Nonpatent Publications 3 and 4). CD is an enzyme that converts 5-fluorocytosine (hereinafter, called 5-FC), which is a prodrug (precursor) of 5-fluorouracil (hereinafter, called 5-FU) that has an antitumor activity, into 5-FU.

Construction of such a transformed bacterium requires an expression vector. However, since an E. coli-derived plasmid vector conventionally used for transforming E. coli in the field of genetic engineering is naturally unable to be replicated in bacteria other than E. coli, it is necessary in the construction of the transformed bacterium to modify a plasmid vector so that it is capable of being replicated in the transformed bacterium.

In the above publications, expression vectors used in the construction of such transformed bacteria for treatment of a malignant tumor have also been reported, and Patent Publications 1 to 3 report the shuttle plasmids pNTR500F, pCD540FT, etc., which are replicated in both E. coli and Clostridium.

Furthermore, Patent Publication 4 reports the shuttle plasmid pBLES 100-S-eCD, and the shuttle plasmid pBLES 100 used for construction of the shuttle plasmid pBLES100-S-eCD, which are replicated in both E. coli and Bifidobacterium.

In addition, the shuttle plasmids pAV001-HU-eCD, which can transform Bifidobacterium longum at a high efficiency of more than 100 times that of the shuttle plasmid pBLES100-S-eCD, have also been reported (see e.g. Patent Publication 5).

Furthermore, the shuttle plasmid pAV001-HU-eCD-M968, which is a plasmid single-nucleotide variant of the shuttle plasmid pAV001-HU-eCD in which the DNA of the target gene inserted into the shuttle plasmid pAV001 has been partially varied, has been reported (see e.g. Patent Publication 6).

Furthermore, for example, the shuttle plasmid pDG7, which is replicated in both E. coli and Bifidobacterium, the shuttle plasmids pEBM3 and pECM2, which are replicated in both E. coli and Clostridium, the shuttle plasmid pLP825, which is replicated in both E. coli and Lactobacillus, etc. have been reported (see e.g. Nonpatent Publication 5).

As hereinbefore described, various plasmid vectors used for constructing a transformant other than E. coli have been reported, they are all shuttle vectors that are replicated in both E. coli and a transformant bacterium other than E. coli, and there is no known plasmid vector that is capable of being replicated only in a non-E. coli transformant bacterium.

[Patent Publication 1] U.S. Pat. No. 6,416,754
[Patent Publication 2] U.S. Pat. No. 6,652,849
[Patent Publication 3] US Pat. Laid-open No. 2003/0103952
[Patent Publication 4] JP, A, 2002-97144
[Patent Publication 5] WO 2006-57289
[Patent Publication 6] WO 2007-136107
[Nonpatent Publication 1] Yazawa et al., Cancer Gene Ther., 7, 269-274 (2000)
[Nonpatent Publication 2] Yazawa et al., Breast Cancer Res. Treat., 66, 165-170 (2001)
[Nonpatent Publication 3] Nakamura et al., Biosci. Biotechnol. Biochem., 66, 2362-2366 (2002)
[Nonpatent Publication 4] Fujimori et al., Curr. Opin. Drug Discov. Devel., 5, 200-203 (2002)
[Nonpatent Publication 5] Alessandra Argnani et al., Microbiology.; 142: 109-114 (1996)

SUMMARY OF INVENTION

Problems to be Solved by the Invention

In a method for treating a disease that is in an anaerobic environment (hereinafter, called an anaerobic disease), such as a solid tumor or an ischemic disease, using a transformant gene transporter, the gene transporter to be used is required to be a nonpathogenic, obligate anaerobe that survives and proliferates only in diseased tissue in an anaerobic state, and does not survive or proliferate in normal tissue that is not in an anaerobic state.

Furthermore, it is extremely important that the transforming gene in the gene transporter is not to be horizontally transferred to a pathogenic bacterium, an aerobic bacterium or facultative anaerobe other than the gene transporter, and that, even if the transforming gene was horizontally transferred, it is not to be replicated in that bacterium. Because of this, an expression vector used for constructing a transformant gene transporter is desirably replicated only in the transformant and not replicated in a bacterium other than the transformant, in particular, not in a pathogenic, or aerobic bacterium or facultative anaerobe.

Most of the expression vectors reported so far have been shuttle vectors that are replicated in both the transformant bacterium and a bacterium other than the transformant bacterium, e.g., *E. coli*, and they are not expression vectors that are replicated only in a non-*E. coli* transformant.

It is an object of the present invention to provide an expression vector that is replicated only in a non-*E. coli* transformant but is not replicated in a bacterium other than the transformant and, in particular, not in a pathogenic, or aerobic bacterium or facultative anaerobe such as *E. coli*.

Furthermore, it is another object of the present invention to provide a gene transporter composed of an anaerobic microorganism transformed by the expression vector, a pharmaceutical composition that contains the gene transporter, and an agent for the treatment of anaerobic disease that contains the transformant bacterium.

Means for Solving the Problems

The present inventors have previously selected a gene that expresses CD, among proteins having the activity of converting an antitumor substance precursor into an antitumor substance, as a target gene; then have constructed the shuttle plasmid pBLES 100-S-eCD as a plasmid vector having the target gene inserted thereinto, in which a plasmid of *E. coli* carrying a CD-expressing gene and a *Bifidobacterium longum*-derived plasmid are fused. The inventors have found and reported that the *Bifidobacterium longum* 105A/pBLES100-S-eCD generated by recombining *Bifidobacterium longum* 105A using the above is promising as a gene transporter useful for the treatment of malignant tumors (Patent Publication 4).

In order to further improve the fused plasmid, the present inventors have reported *Bifidobacterium longum* 105A/pAV001-HU-eCD-M968 and a method for the construction thereof, in which the plasmid pAV001-HU-eCD-M968, which is a plasmid single-nucleotide variant of the plasmid pAV001-HU-eCD, is produced by partially varying the DNA of the inserted target gene, and *Bifidobacterium* longum 105A is recombined using the above (Patent Publication 6).

Since all of these plasmids are shuttle plasmids that are replicated in both *Bifidobacterium* and *E. coli*, when they are horizontally transferred to *E. coli* from any cause, they are replicated in *E. coli*.

The present inventors have carried out an intensive investigation in order to solve the above problems, and have constructed the plasmid pBifiCD by removing, from the above plasmid pAV001-HU-eCD-M968, pUC ori, which is a fragment containing an origin of replication for *E. coli*. It has been confirmed that, an *E. coli* JM109 competent cell (Takara Bio Inc.) was not transformed with the plasmid pBifiCD of the present invention by a heat shock, and that there was no possibility of horizontal transfer.

A bacterium transformed with the plasmid of the present invention, for example, *Bifidobacterium longum* 105-A/pBifiCD (National Institute of Technology and Evaluation Patent Microorganisms Depositary (NPMD) Accession No. NITE BP-491), which is a recombinant *Bifidobacterium longum* 105-A, exhibits a good CD expression activity, and it exhibits a marked tumor growth suppression effect when used in combination with the prodrug 5-FC, which is converted by said CD into the antitumor substance 5-FU, indicating that it is promising as an excellent therapeutic for a solid tumor.

Surprisingly, it has further been found that this recombinant *Bifidobacterium* has a high plasmid retention stability, and, furthermore, since they do not contain an origin of replication for *E. coli*, even if a horizontal transfer to *E. coli* occurs, there is no possibility of their replication in *E. coli*. Therefore, the recombinant bacterium is promising as an extremely safe and high quality gene transporter.

Accordingly, the present invention relates to [1] an expression vector that is a plasmid vector that functions in an anaerobic microorganism, the expression vector not containing a plasmid replication unit that functions in *E. coli*, [2] the expression vector according to [1], wherein the anaerobic microorganism is an enterobacterium other than *E. coli*, [3] the expression vector according to [2], wherein the enterobacterium other than *E. coli* is a enterobacterium selected from the group consisting of *Bifidobacterium, Lactobacillus, Enterococcus, Streptococcus*, and *Clostridium*, [4] the expression vector according to any one of [1] to [3], wherein the expression vector comprises (1) a plasmid replication unit that functions in an anaerobic microorganism other than *E. coli* and (2) a protein expression unit comprising a DNA coding for a protein having target activity and a DNA fragment comprising a promoter and a terminator that function in the anaerobic microorganism, [5] the expression vector according to [4], wherein the plasmid replication unit that functions in an anaerobic microorganism other than *E. coli* is a plasmid replication unit that functions in an anaerobic microorganism selected from the group consisting of *Bifidobacterium, Lactobacillus, Enterococcus, Streptococcus*, and *Clostridium*, [6] the expression vector according to [5], wherein the plasmid replication unit that functions in an anaerobic microorganism other than *E. coli* is a plasmid replication unit that functions in *Bifidobacterium*, [7] the expression vector according to [6], wherein the plasmid replication unit that functions in *Bifidobacterium* is a pTB6 rep unit comprising an OriV region and a RepB gene, [8] the expression vector according to [7], wherein a gene coding for the pTB6 rep unit comprising the OriV region and the RepB gene is a DNA represented by the nucleotide sequence from the 1796th to the 3391st nucleotides of SEQ ID NO:4 or a single-nucleotide polymorphism thereof, [9] the expression vector according to any one of [4] to [8], wherein the promoter and the terminator that function in an anaerobic microorganism are a promoter and a terminator that function in a bacterium selected from the group consisting of *Bifidobacterium, Lactobacillus, Enterococcus, Streptococcus*, and *Clostridium*, [10] the expression vector according to [9], wherein the promoter and the terminator that function in an anaerobic microorganism are a promoter and a terminator that function in *Bifidobacterium*, [11] the expression vector according to [10], wherein the promoter and the terminator that function in *Bifidobacterium* are a promoter and a terminator of a gene coding for a histone-like DNA-binding protein that functions in a *Bifidobacterium*, [12] the expression vector according to [11], wherein the promoter and the terminator of a gene coding for a histone-like DNA-binding protein that functions in *Bifidobacterium* are a promoter and a terminator of a gene coding for a *Bifidobacterium*-derived histone-like DNA-binding protein, [13] the expression vector according to [12], wherein the gene coding for a promoter and a terminator of a gene coding for a histone-like DNA-binding protein is DNA represented by the nucleotide sequence from the 7th to the 367th and from the 1676th to the 1789th nucleotides of SEQ ID NO:4, respectively, or a single-nucleotide polymorphism thereof, [14] the expression vector according to [4] to [13], wherein the protein having target activity is a protein having a therapeutic activity for a disease that is in an anaerobic environment, [15] the expression vector according to [14], wherein the protein having a therapeutic activity for a disease that is in an anaerobic environment is (a) a protein having an antitumor activity or (b) a protein having an activity of converting an antitumor substance precursor into an antitumor substance, [16] the expression vector according to [15], wherein the protein having a therapeutic activity for a disease that is in an anaerobic environment is a protein having an activity of converting an antitumor substance precursor into an antitumor substance, [17] the expression vector according to [16], wherein the protein having an activity of converting an antitumor substance precursor into an antitumor substance is selected from the group consisting of cytosine deaminase, nitroreductase, and β-glucuronidase, [18] the expression vector according to [17], wherein the protein having an activity of converting an antitumor substance precursor into an antitumor substance is cytosine deaminase, [19] the expression vector according to [18], wherein a gene coding for cytosine deaminase is a DNA represented by the nucleotide sequence from the 395th to the 1675th nucleotides of SEQ ID NO:4 or a single-nucleotide polymorphism thereof, [20] the expression vector according to any one of [4] to [19] further comprising (3) a selection marker activity gene unit, wherein the selection marker activity is selected from the group consisting of drug resistance, auxotrophy, and culture medium selectivity, [21] the expression vector according to [20], wherein the selection marker activity is a drug resistance selected from the group consisting of spectinomycin resistance, ampicillin resistance, tetracycline resistance, neomycin resistance, and kanamycin resistance, [22] the expression vector according to [21], wherein the selection marker activity is spectinomycin resistance, [23] the expression vector according to [22], wherein a DNA coding for a protein exhibiting selection marker activity is a DNA coding for spectinomycin adenyltransferase, [24] the expression vector according to [23], wherein a DNA comprising a DNA coding for spectinomycin adenyltransferase and a promoter sequence thereof is a DNA represented by the nucleotide sequence from the 3398th to the 4476th nucleotides of SEQ ID NO:4 or a single-nucleotide polymorphism thereof, and [25] the expression vector according to [24], comprising a DNA sequence represented by the nucleotide sequence of SEQ ID NO:4 (pBifiCD).

Furthermore, the present invention relates to [26] a process for constructing an expression vector, the process comprising producing a shuttle plasmid comprising (1) a plasmid replication unit that functions in an anaerobic microorganism other than *E. coli* and (2) a protein expression unit comprising a DNA coding for a protein having target activity and a DNA fragment comprising a promoter and a terminator that function in the anaerobic microorganism, the shuttle plasmid being replicated in both *E. coli* and a host bacterium other than *E. coli*, and removing from the shuttle plasmid a plasmid replication unit that functions in *E. coli*.

Moreover, the present invention relates to [27] a gene transporter comprising an anaerobic microorganism transformed by the expression vector according to any one of [1] to [25], [28] the gene transporter according to [27], wherein the anaerobic microorganism is an enterobacterium other than *E. coli*, [29] the gene transporter according to [28], wherein the enterobacterium other than *E. coli* is selected from the group consisting of *Bifidobacterium, Lactobacillus, Enterococcus, Streptococcus*, and *Clostridium*, [30] the gene transporter according to [29], wherein the enterobacterium other than *E. coli* is *Bifidobacterium*, [31] the gene transporter according to [30], wherein the *Bifidobacterium* is selected from the group consisting of *Bifidobacterium adolescentis, Bifidobacterium animalis, Bifidobacterium infantis, Bifidobacterium thermophilum, Bifidobacterium pseudolongum, Bifidobacterium bifidum, Bifidobacterium breve*, and *Bifidobacterium longum*, [32] the gene transporter according to [31], wherein the *Bifidobacterium* is *Bifidobacterium longum*, [33] the gene transporter according to any one of [27] to [32], wherein it is capable of growing in a tumor tissue in an anaerobic environment, and is capable of expressing a protein having a therapeutic activity for a disease that is in an anaerobic environment, [34] the gene transporter according to [33], wherein it is capable of growing within a tumor tissue that is in an anaerobic environment, and the protein having a therapeutic activity for a disease that is in an anaerobic environment is (a) a protein having antitumor activity or (b) a protein having an activity of converting an antitumor substance precursor into an antitumor substance, [35] the gene transporter according to [34], wherein it is capable of growing in a tumor tissue that is in an anaerobic environment, and the protein having a therapeutic activity for a disease that is in an anaerobic environment is a protein having an activity of converting an antitumor substance precursor into an antitumor substance, [36] the gene transporter according to [35], wherein the protein having an activity of converting an antitumor substance precursor into an antitumor substance is selected from the group consisting of cytosine deaminase, nitroreductase, and β-glucuronidase, [37] the gene transporter according to [36], wherein the protein having an activity of converting an antitumor substance precursor into an antitumor substance is cytosine deaminase, and [38] the gene transporter according to [37], wherein the gene transporter is *Bifidobacterium longum* 105-A/pBifiCD (National Institute of Technology and Evaluation Patent Microorganisms Depositary (NPMD) Accession No. NITE BP-491).

Furthermore, the present invention relates to [39] a pharmaceutical composition comprising the gene transporter according to any one of [27] to [38], [40] a pharmaceutical composition comprising in combination the gene transporter according to any one of [34] to [38], and an antitumor substance precursor that is converted into an antitumor substance by a protein that the gene transporter is capable of expressing and that has an activity of converting the antitumor substance precursor into the antitumor substance, and [41] the pharmaceutical composition according to [40], wherein the protein having an activity of converting the antitumor substance precursor into the antitumor substance is cytosine deaminase, and the antitumor substance precursor is 5-fluorocytosine.

Moreover, the present invention relates to [42] a therapeutic agent for a solid tumor comprising the gene transporter according to any one of [34] to [38] in an amount sufficient to express an effective therapeutic dose of a protein having antitumor activity, [43] a therapeutic agent for a solid tumor comprising in combination the gene transporter according to any one of [34] to [38] in an amount sufficient to express a protein having an activity of converting an antitumor substance precursor into an effective therapeutic dose of an antitumor substance, and an antitumor substance precursor in an amount that can be converted into an effective therapeutic dose of the antitumor substance, the antitumor substance precursor being converted by the protein that the gene transporter is capable of expressing, and [44] the solid tumor treatment agent according to [43], wherein the protein having an activity of converting an antitumor substance precursor into an antitumor substance is cytosine deaminase, and the antitumor substance precursor is 5-fluorocytosine.

In the present application, a DNA coding for (a) a protein having an antitumor activity or a DNA coding for (b) a protein having an activity of converting an antitumor substance precursor into an antitumor substance may hereinafter be called 'a DNA coding for a target protein'.

Also encompassed herein is an isolated, non-naturally occurring expression vector that functions in an anaerobic microorganism, the expression vector not containing a plasmid replication unit that functions in *E. coli*. In one aspect, the expression vector comprises a protein expression unit comprising a DNA coding for a protein having target activity, wherein the protein having target activity does not naturally occur in the anaerobic microorganism. In a further aspect, the target activity comprises antitumor activity or conversion of an antitumor substance precursor into an antitumor substance.

Also encompassed herein is an isolated expression vector that functions in an anaerobic microorganism and does not contain a plasmid replication unit that functions in *E. coli*, said expression vector comprising (1) a plasmid replication unit that functions in an anaerobic microorganism other than *E. coli*, and (2) a protein expression unit comprising a DNA coding for a protein having target activity and a DNA fragment comprising a promoter and a terminator that function in the anaerobic microorganism, wherein the protein having target activity does not naturally occur in the anaerobic microorganism. In one aspect, the target activity comprises antitumor activity or conversion of an antitumor substance precursor into an antitumor substance.

Also encompassed herein are methods for treating solid tumors comprising administration of pharmaceutical compositions and/or therapeutic agents comprising an expression vector of the invention. In one aspect, the method results in a reduction in the size of the tumor; suppression of the growth of the tumor; inhibition of the proliferation of the tumor cells; reduction in the number of tumor cells; and/or a decrease in the viability of the tumor cells.

EFFECTS OF THE INVENTION

The expression vector of the present invention does not include an origin of replication that functions in a bacterium, in particular in *E. coli*, other than a transformant bacterium, and it is a extremely safe vector that has no possibility of being replicated in a bacterium other than the transformed bacterium and, in particular, not in a pathogenic, or aerobic or facultative anaerobic bacterium, such as *E. coli*.

A gene transporter transformed using the expression vector of the present invention has a high plasmid retention stability; and, as described above, even if the vector was horizontally transferred to a bacterium other than the transformant, in particular, to a pathogenic, or aerobic or facultative anaerobic bacterium, such as *E. coli*, there is no risk of being replicated in such other bacterium. Therefore, the gene transporter of the present invention is promising as a highly safe, high-quality gene transporter.

BRIEF DESCRIPTION OF DRAWINGS

[FIG. 1] A diagram showing a step of constructing a selection marker plasmid (pSPCM-pUCori) (Step 1).

[FIG. 2] A diagram showing a step of constructing a selection marker activity protein plasmid (pHU-eCDm-SPCM-pUCori) (Step 2).

[FIG. 3] A diagram showing a step of constructing a shuttle plasmid (pCDshuttle) (Step 3).

[FIG. 4] A diagram showing a step of constructing the plasmid 'pBifiCD' (Step 4).

[FIG. 5] A diagram showing the antitumor effect of *B. longum* Re-105A/pBifiCD cloning strain.

MODES FOR CARRYING OUT THE INVENTION

The expression vector of the present invention is a plasmid vector that functions in an anaerobic bacterium and, in particular, an enterobacterium other than *E. coli*, such as *Bifidobacterium, Lactobacillus, Enterococcus, Streptococcus*, or *Clostridium*, and is an expression vector not containing a plasmid replication unit that functions in a bacterium, particularly *E. coli*, other than the transformed bacterium.

More specifically, it is, for example, an expression vector comprising (1) a plasmid replication unit that functions in an anaerobic microorganism other than *E. coli*, and (2) a protein expression unit comprising a DNA coding for a protein having target activity and a DNA fragment comprising a promoter and a terminator that function in the anaerobic microorganism, and the expression vector does not contain a plasmid replication unit that functions in a bacterium other than the transformant bacterium, particularly in *E. coli*.

Most of the plasmid vectors that have been reported so far are constructed by fusing an *E. coli*-derived plasmid and a transformant bacterium-derived plasmid, because of the accumulated information on gene transfection techniques and the assurance of transfection. They are shuttle vectors that function in both *E. coli* and a transformant bacterium, and are not expression vectors that function only in a non-*E. coli* transformant bacterium.

The expression vector of the present invention is characterized in that, for example, it consists essentially of (1) a plasmid replication unit that functions in an anaerobic microorganism other than *E. coli* and (2) a protein expression unit consisting essentially of a DNA coding for a protein having target activity and a DNA fragment comprising a promoter and a terminator that function in the anaerobic microorganism, and the expression vector does not contain a plasmid replication unit that functions in a bacterium other than the transformant bacterium, particularly *E. coli*.

The plasmid replication unit of the expression vector of the present invention which functions in an anaerobic microorganism other than *E. coli* may be any plasmid replication unit, as long as it functions in an anaerobic microorganism other than *E. coli*, for example, in an enterobacterium such as *Bifidobacterium, Lactobacillus, Enterococcus, Streptococcus*, or *Clostridium*, and as long as it does not function in an anaerobic microorganism other than the transformant bacterium; examples thereof include a plasmid replication unit that functions in an anaerobic microorganism other than *E. coli*, for example, in *Bifidobacterium*. Specific examples include a pTB6 rep unit consisting essentially of an OriV region and a RepB gene that function in *Bifidobacterium*, or a single-nucleotide polymorphism thereof. More specific examples include a DNA represented by the nucleotide sequence from the 1796th to the 3391st nucleotides of SEQ ID NO:4 or a single-nucleotide polymorphism thereof.

Furthermore, the promoter and the terminator of the protein expression unit of the expression vector of the present invention may be any promoter and terminator, as long as they function in an anaerobic microorganism, for example, in an enterobacterium such as *Bifidobacterium, Lactobacillus, Enterococcus, Streptococcus*, or *Clostridium*; examples thereof include a promoter and a terminator of a gene coding for a histone-like DNA-binding protein that functions in an anaerobic microorganism, for example, promoter and terminator DNA of a gene coding for a Bifidobacterium-derived histone-like DNA-binding protein or a single-nucleotide polymorphism thereof. Specific examples include DNA represented by the nucleotide sequence from the 7th to the 367th and from the 1676th to the 1786th nucleotides of SEQ ID NO:4, respectively, or a single-nucleotide polymorphism thereof.

Moreover, the expression vector of the present invention may further comprise (3) a selection marker activity gene unit. The selection marker activity possessed by the expression vector of the present invention is not particularly limited as long as it is capable of selecting an anaerobic microorganism transformed by the plasmid vector of the present invention; examples thereof include a drug resistance marker such as spectinomycin resistance, ampicillin resistance, tetracycline resistance, neomycin resistance, or kanamycin resistance, and auxotrophy, and spectinomycin resistance is preferable.

Examples of the selection marker activity gene unit include, for example, a DNA containing a DNA coding for a protein exhibiting spectinomycin resistance activity or a single-nucleotide variant thereof and a promoter sequence thereof; for example, a DNA coding for *Enterococcus faecalis*-derived spectinomycin adenyltransferase (hereinafter, called AAD9 cassette) or a single-nucleotide polymorphism thereof. A specific examples include a DNA represented by the nucleotide sequence from the 3398th to the 4476th nucleotides of SEQ ID NO:4 or a single-nucleotide polymorphism thereof.

The 'single-nucleotide variant' referred to in the present invention means a single-nucleotide polymorphism in which a nucleotide of at least one site has been altered (hereinafter, called a SNP), and includes not only a SNP at only one site but also SNPs at a plurality of sites.

A gene which is incorporated into the protein expression unit of the expression vector of the present invention may be, for example, when the therapeutic agent for an anaerobic disease of the present invention is used as a therapeutic agent for a malignant tumor, any gene as long as it expresses a protein having antitumor activity or a protein having an activity of converting an antitumor substance precursor into an antitumor substance, and as long as it is not DNA that inhibits transformation such as a giant DNA (at least about 10 kb) or a DNA that is toxic to recipient cells.

The protein expressed by said gene having antitumor activity includes, for example, a cytokine, and specific examples of the cytokine include interferons (IFN)-α, β, and γ, granulocyte macrophage colony stimulating factor (GM-CSF), interleukins (IL)-1α, 1β, 2, 3, 4, 6, 7, 10, 12, 13, 15, and 18, tumor necrosis factor (TNF)-α, lymphotoxin (LT)-β, granulocyte colony stimulating factor (G-CSF), macrophage colony stimulating factor (M-CSF), macrophage migration inhibition factor (MIF), leukemia inhibitory factor (LIF), T-cell activation costimulatory factors B7 (CD80) and B7-2 (CD86), KIT ligand, and oncostatin M. Furthermore, examples include angiogenesis suppressing substances such as endostatin, angiostatin, and kringles 1, 2, 3, 4, and 5.

The sequences of these proteins are known for various organisms, and a DNA coding for a protein having antitumor activity used in the present invention may be obtained by utilizing a known technique such as a PCR method based on the sequence information.

Furthermore, examples of the protein having an activity of converting an antitumor substance precursor into an antitumor substance include: cytosine deaminase (hereinafter, called CD), which is an enzyme that converts 5-fluorocytosine (hereinafter, called 5-FC) into the antitumor-active substance 5-fluorouracil (hereinafter, called 5-FU); nitroreductase, which is an enzyme that converts 5-aziridino-2,4-dinitrobenzamide (hereinafter, called CB1945) into an antitumor-active alkylating agent; herpes simplex virus 1 type thymidine kinase (hereinafter, called HSV1-TK), which is an enzyme that converts ganciclovir into an antitumor-active metabolite; and β-glucuronidase, which is an enzyme that converts a glucuronidated antitumor-active substance into an antitumor active substance. Preferred examples include CD, which is the enzyme that converts 5-FC into 5-FU.

A DNA coding for CD may be, for example, plasmid pAdex 1 CSCD (Riken Gene Bank RDB No. 1591), which contains DNA coding for *E. coli*-derived CD, or one isolated from plasmid pMK 116, which similarly contains a DNA coding for *E. coli*-derived CD (D. A. Mead et al., Protein Engineering 1: 67-74 (1986)).

Examples of the DNA coding for *E. coli*-derived CD include DNA represented by the nucleotide sequence of the 395th to the 1675th nucleotides of SEQ ID NO:4 or a single-nucleotide polymorphism thereof.

Furthermore, when the therapeutuc agent for an anaerobic disease of the present invention is used as a therapeutic agent for an ischemic disease, a protein having angiogenic promoting activity, which is useful for treatment of an ischemic disease, can be used as a gene incorporated into a protein expression unit of the expression vector of the present invention. Specific examples include fibroblast growth factor 2 (FGF2), endothelial cell growth factor (ECGF), vascular endothelial growth factor (VEGF), and hepatocyte growth factor (HGF).

Similarly, the sequences of these proteins are known for various organisms, and a DNA coding for a protein having angiogenic promoting activity used in the present invention may be obtained by utilizing a known technique such as a PCR method based on the sequence information.

The vector of the present invention includes any vector as long as it is a plasmid comprising, for example, a plasmid replication unit that functions in an anaerobic microorganism other than *E. coli*, a protein expression unit comprising a DNA coding for a protein having target activity and a DNA fragment containing a promoter and a terminator that function in the anaerobic microorganism, and a selection marker activity gene unit, and as long as the plasmid being capable of functioning within an anaerobic microorganism when transformed into the anaerobic microorganism, and as long as the plasmid does not contain a plasmid replication unit that functions in a bacterium other than the transformant bacterium, particularly *E. coli*.

Examples include a plasmid constructed by imcorporating into the shuttle plasmids pBLES100 (Patent Publication 4), pAV100 (Patent Publication 5), pBRASTA101 (Tanaka et al., 2005, Biosci. Biotechnol. Biochem., 69(2): 422-425), pDG7, pEBM3, pECM2, pLP825, etc. (Nonpatent Publication 5), which have been reported in the publications, a protein expression unit comprising a DNA coding for a given protein having target activity and a DNA fragment comprising a promoter and a terminator that function in the anaerobic microorganism, and removing a plasmid replication unit that functions in *E. coli*.

Other examples thereof include those constructed by recombining a protein expression unit which has been imcorporated into the plasmid, e.g., pNTR500F, pCD540FT, etc. (Patent Publications 1 to 3), pBLES100-S-eCD (Patent Publication 4), pAV001-HU-eCD (Patent Publication 5), pAV001-HU-eCD-M968 (Patent Publication 6), etc., with another given protein expression unit, and further removing a plasmid replication unit that functions in *E. coli*.

Specific examples of the expression vector of the present invention include, for example, a vector that has a pTB6 rep unit comprising a RepB gene and an OriV region that function in a *Bifidobacterium* as the plasmid replication unit that functions in an anaerobic microorganism other than *E. coli*, and a promoter and a terminator of a gene coding for a *Bifidobacterium*-derived histone-like DNA-binding protein as the DNA fragment containing the promoter and the terminator that function in the anaerobic microorganism, and a DNA coding for the CD enzyme that converts 5-FC into 5-FU as the DNA coding for the protein having target activity, and a DNA (AAD9 cassette) coding for *Enterococcus faecalis*-derived spectinomycin adenyltransferase as the selection marker activity gene unit.

More specific examples include pBifiCD, which is represented by the nucleotide sequence of SEQ ID NO:4.

The vector of the present invention may be constructed by, for example, the following method.

For example, the vector of the present invention may be constructed by (1) constructing a plasmid comprising a origin of replication of *E. coli*, for example pUC ori, and a selection marker activity gene unit, for example an AAD9 cassette (hereinafter, called a selection marker plasmid) (hereinafter, called Step 1), (2) preparing a linear plasmid of the selection marker plasmid, ligating it with a promoter and a terminator, for example, a promoter and a terminator of a gene coding for a *Bifidobacterium*-derived histone-like DNA-binding protein, and (a) a protein having an antitumor activity or (b) a protein having an activity of converting an antitumor substance precursor into an antitumor substance, for example, a fragment comprising a CD (hereinafter, called protein expression unit), to construct a plasmid having a selection marker activity gene unit and a protein expression unit (hereinafter, called a selection marker activity protein plasmid) (hereinafter, called Step 2), (3) preparing a linear plasmid of this selection marker-active protein plasmid, ligating it with a plasmid replication unit that functions in an anaerobic microorganism other than *E. coli*, for example, a DNA fragment of a pTB6 rep unit comprising a RepB gene and an OriV region that function in a *Bifidobacterium* (hereinafter, called a plasmid replication unit), to construct a plasmid having an *E. coli* origin of replication and a selection marker activity gene unit, a protein expression unit, and a plasmid replication unit (hereinafter, called a shuttle plasmid) (hereinafter, called Step 3), and (4) removing the *E. coli* origin of replication from this shuttle plasmid (hereinafter, called Step 4).

The procedure of each step may be carried out in accordance with a known method described in the literature.

The vector may also be constructed by incorporating, by a standard method, a protein expression unit comprising a DNA coding for a given protein having target activity and a DNA fragment containing a promoter and a terminator that function in the anaerobic microorganism into the above-mentioned various shuttle plasmids such as the shuttle plasmids pBLES100 (Patent Publication 4), pAV001 (Patent Publication 5), pBRASTA101 (Tanaka et al., 2005, Biosci. Biotechnol. Biochem., 69(2): 422-425), pDG7, pEBM3, pECM2, pLP825, etc. (Nonpatent Publication 5) pNTR500F, pCD540FT, etc. (Patent Publications 1 to 3), followed by similarly removing a plasmid replication unit functioning in *E. coli* by a standard method.

Furthermore, in the same manner as for the above plasmid pBifiCD of the present invention in which the pUC ori of the fragment containing the *E. coli* origin of replication is removed from the plasmid pAV001-HU-eCD-M968 (Patent Publication 6), the vector of the present invention may also be constructed by removing a plasmid replication unit functioning in *E. coli* from the plasmids pNTR500F, pCD540FT (Patent Publication 1 to 3), pBLES100-S-eCD (Patent Publication 4), pAV001-HU-eCD (Patent Publication 5), etc.

Moreover, the vector of the present invention may also be constructed by recombining a protein expression unit that has been imcorporated into the plasmids pNTR500F, pCD540FT (Patent Publication 1 to 3), pBLES100-S-eCD (Patent Publication 4), pAV001HU-eCD (Patent Publication 5), pAV001-HU-eCD-M968 (Patent Publication 6), etc. with another given protein expression unit, and then removing therefrom a plasmid replication unit that functions in *E. coli*.

The gene transporter for the treatment of an anaerobic disease of the present invention may be constructed by transforming a given anaerobic microorganism that is transformed in accordance with a known genetic engineering method using the expression vector of the present invention.

Since the anaerobic microorganism transformed by the expression vector of the present invention is used in an agent for treating an anaerobic disease such as a solid tumor, it is essential for this anaerobic microorganism to be obligately anaerobic and nonpathogenic; pathogenic bacteria such as *Clostridium* or *Salmonella* may be used if they are made nonpathogenic, and a facultative anaerobe such as a *Lactobacillus* may be used if it has mutated so as to be obligately anaerobic.

Preferred examples include nonpathogenic anaerobic bacteria; nonpathogenic enterobacteria are more preferable, and among them bifidobacteria are most preferable.

Examples of the bifidobacteria include *Bifidobacterium adolescentis, Bifidobacterium animalis, Bifidobacterium infantis, Bifidobacterium thermophilum, Bifidobacterium pseudolongum, Bifidobacterium bifidum, Bifidobacterium breve*, and *Bifidobacterium longum*, and *Bifidobacterium longum* is the most preferable.

These bacteria are either commercially available or readily available from a depository institution. For example, *Bifidobacterium longum* ATCC-15707, *Bifidobacterium bifidum* ATCC-11863, *Bifidobacterium infantis* ATCC-15697, etc. may be readily obtained from ATCC (The American Type Culture Collection).

The strain of each bacterium is not particularly limited, and examples of the strain of *Bifidobacterium longum* include *Bifidobacterium longum* 105-A strain, *Bifidobacterium longum* aE-194b strain, *Bifidobacterium longum* bs-601 strain, and *Bifidobacterium longum* M101 strain, and among them *Bifidobacterium longum* 105-A strain is preferable.

Examples of the strain of *Bifidobacterium breve* include *Bifidobacterium breve* standard strain (JCM1192). *Bifidobacterium breve* aS-1 strain, and *Bifidobacterium breve* 1-53-8W strain, and among them *Bifidobacterium breve* standard strain and *Bifidobacterium breve* aS-1 strain are preferable.

Examples of the strain of *Bifidobacterium infantis* include *Bifidobacterium infantis* standard strain (JCM1222) and *Bifidobacterium infantis* I-10-5 strain, and among them *Bifidobacterium infantis* standard strain and *Bifidobacterium infantis* I-10-5 strain are preferable.

Furthermore, examples of the strain of *Bifidobacterium lactentis* include *Bifidobacterium lactentis* standard strain (JCM1220).

The gene transporter of the present invention is a gene transporter comprising an anaerobic microorganism transformed by the expression vector of the present invention, and is not particularly limited as long as it is capable of growing in tissue that is in an anaerobic environment and be capable of expressing a protein having target activity, and, moreover, is having little or no possibility of being horizontally transferred to a bacterium other than the transformant, in particular to a pathogenic, or aerobic or facultative anaerobic microorganism.

Preferred examples of the gene transporter of the present invention include a gene transporter that is capable of growing in tumor tissue that is in an anaerobic environment and is capable of expressing a protein having activity of converting an antitumor substance precursor into an antitumor substance. A more preferred examples include a gene transporter comprising *Bifidobacterium* that is capable of growing in tumor tissue that is in an anaerobic environment and is capable of expressing a CD enzyme that converts 5-FC into 5-FU. A particularly preferred examples include *Bifidobacterium longum* 105-A strain transformed by pBifiCD (*Bifidobacterium longum* 105-A/pBifiCD; NPMD Reference No. NITE ABP-491) deposited with Incorporated Administrative Agency National Institute of Technology and Evaluation Patent Microorganisms Depositary (NPMD) (Post code 292-0818, 2-5-8 Kazusakamatari, Kisarazu-shi, Chiba-ken, Japan) as Accession No. NITE BP-491 on Feb. 19, 2008.

Construction of the gene transporter of the present invention may be carried out in accordance with a method described in a commercial experimental textbook such as, for example, Gene Manual (Kodansha), Gene Manipulation Experimental Method, Ed. by Yasuyuki Takagi (Kodansha), Molecular Cloning, Cold Spring Harbor Laboratory (1982), Molecular Cloning 2nd Edition, Cold Spring Harbor Laboratory (1989), or Methods in Enzymol., 194 (1991).

The pharmaceutical composition of the present invention is not particularly limited as long as it contains the gene transporter of the present invention. Furthermore, the therapeutic agent for an anaerobic disease of the present invention is not particularly limited as long as it contains the gene transporter of the present invention.

Moreover, the pharmaceutical composition or the therapeutic agent for an anaerobic disease of the present invention may contain two or more of the gene transporter of the present invention.

Furthermore, the pharmaceutical composition or the therapeutic agent for an anaerobic disease of the present invention may be used in combination with a pharmaceutical composition or a therapeutic agent for an anaerobic disease that contains, other than the gene transporter of the present invention, a compound exhibiting an anaerobic disease treating effect.

Moreover, the pharmaceutical composition or the therapeutic agent for an anaerobic of the present invention may contain additional components other than the gene transporter of the present invention as long as the effect of the present invention is not impaired. Examples of such additional components include a pharmaceutically acceptable support, an excipient, and a diluent.

The dosage form of the pharmaceutical composition or the anaerobic disease treatment agent of the present invention is not particularly limited, and examples thereof include a liquid agent or a solid preparation containing the gene transporter of the present invention. The liquid agent may be produced by purifying a culture fluid of an anaerobic bacterium of the gene transporter of the present invention, adding thereto as required an appropriate physiological saline, fluid replacement, or medicinal additive, and filling an ampoule, vial, etc. therewith. The solid preparation may be produced by adding an appropriate protectant to a liquid agent, filling an ampoule, vial, etc. therewith, and then lyophilizing or L-drying, or by adding an appropriate protectant to a liquid agent, lyophilizing or L-drying this, and then filling an ampoule, vial, etc. therewith. With regard to a method for administering the pharmaceutical composition or the anaerobic disease treatment agent of the present invention, both oral administration and parenteral administration are possible, but parenteral administration is preferable and, for example, intravenous injection, subcutaneous injection, local infusion, or intracerebroventricular administration can be carried out, and intravenous injection is most preferable.

The dose of the gene transporter of the pharmaceutical composition or the anaerobic disease treatment agent of the present invention is not particularly limited as long as it is an amount sufficient for growing at a disease site and expressing an effective therapeutic dose of an active protein. However, from an economic point of view and for the purpose of minimizing side effects, the dose is preferably as small as possible within a range that can give a required therapeutic effect.

The dose of the gene transporter in the pharmaceutical composition or the therapeutic agent for an anaerobic disease of the present invention is appropriately selected according to the severity of a disease, and the weight, age or gender of a patient, and may appropriately be increased or decreased according to the degree of improvement.

For example, when the anaerobic disease treatment agent of the present invention is used as a solid tumor treatment agent, the dose is appropriately determined according to the antitumor activity exhibited by the anaerobic microorganism itself, the type of protein having antitumor activity produced by the anaerobic microorganism used, the effective therapeutic dose of the antitumor substance converted from the antitumor substance precursor, the amount of active protein produced by the anaerobic microorganism used, etc.

Specifically, in the case of intravenous administration, since it is particularly necessary to reduce a risk such as an embolization due to a mass of bacteria, it is preferable to use an injection at a concentration as low as possible, divide the injection into a plurality of injections, or dilute the injection with an appropriate fluid replacement and administered by continuous infusion. For example, in the case of an adult, $10^6$ to $10^{12}$ cfu per kg body weight per day of the cells of the anaerobic microorganism of the present invention are administered divided into 1 to a plurality of times, successively or at intervals as appropriate, for 1 to a plurality of days. More specifically, 1 to 1000 mL per adult of a preparation containing $10^4$ to $10^{10}$ cfu/mL of the cells of the anaerobic microorganism of the present invention is administered, directly or diluted with an appropriate fluid replacement, and divided into 1 to a plurality of times per day for 1 to several successive days.

Furthermore, in the case of local administration involving direct administration to diseased tissue, since it is required that the bacterial cells colonize and proliferate in the entire diseased tissue as much as possible, it is desirable to administer a high concentration injection at a plurality of positions of the diseased tissue. For example, in the case of an adult, $10^6$ to $10^{12}$ cfu per kg weight of the cells of the anaerobic microorganism of the present invention are administered once or a plurality of times per day, and successively or at intervals as appropriate for 1 day to a plurality of days as necessary. More specifically, 1 to 1000 mL per adult of a preparation containing $10^4$ to $10^{10}$ cfu/mL of the cells of the anaerobic microorganism of the present invention is administered directly, preferably once to several times per day, and successively for 1 to several days as necessary.

When it is observed that the bacteria in the diseased tissue have disappeared during the treatment period, the treatment is first suspended, and then bacteria are administered in the similar manner as above.

When the gene transporter or the anaerobic disease treatment agent of the present invention is an anaerobic bacterium into which is inserted a gene that is capable of expressing a protein having an activity of converting an antitumor substance precursor into an antitumor substance, the pharmaceutical composition or the therapeutic agent for a solid tumor of the present invention containing the gene transporter as an active component is used in a combination with an amount of an antitumor substance precursor that can be converted into an effective amount of an antitumor substance by the protein expressed by the gene transporter. This antitumor substance precursor may be contained in the pharmaceutical composition or the therapeutic agent for a solid tumor containing the gene transporter of the present invention as an active component, but it is preferably used as a pharmaceutical composition containing the antitumor substance precursor in combination with a pharmaceutical composition or therapeutic agent for a solid tumor containing the gene transporter of the present invention as an active component.

The antitumor substance precursor used in the present invention is not particularly limited as long as it is an antitumor substance precursor that has few side effects on normal tissue in the precursor (prodrug) state and has a high therapeutic effect on the solid tumors as the target for treatment after being converted into an antitumor substance. The examples include 5-FC, which is a prodrug of 5-FU; CB1945, which is converted into an antitumor-active alkylating agent; ganciclovir, which is converted into an antitumor-active metabolite; and a glucuronidated antitumor-active substance.

In this way, when the pharmaceutical composition or the therapeutic agent for a solid tumor of the present invention is used in combination with an antitumor substance precursor, the method for administering the pharmaceutical composition or the therapeutic agent for a solid tumor of the present invention may be the same as or different from the method for administering the pharmaceutical composition containing the antitumor substance precursor, and these administrations may be carried out at the same time or at separate times; administration of the pharmaceutical composition containing the antitumor substance precursor is preferably carried out after allowing a sufficient time for the gene transporter of the present invention to grow on the tumor cells after the pharmaceutical composition or the solid tumor treatment agent of the present invention is administered.

Furthermore, when the pharmaceutical composition or the therapeutic agent for a solid tumor of the present invention is used in combination with an antitumor substance precursor, since a gene transporter colonizes and proliferates only in tumor cell tissue that is in an anaerobic environment and locally produces an active protein there, compared with a method for treating a solid tumor using a normal antitumor substance precursor, side effects can be greatly suppressed, and the dose of the antitumor substance precursor can be set in a wide range.

The form of the pharmaceutical composition containing an antitumor substance precursor is not particularly limited, and it may be any of a normal oral preparation such as powder, tablet, or capsule or parenteral preparation such as suppository or injection. Such a pharmaceutical composition may be produced by a normal pharmaceutical method.

The dose of the antitumor substance precursor may be selected appropriately according to the growth rate in the tumor tissue of the gene transporter used in combination and the efficiency of conversion of the antitumor substance precursor into the antitumor substance. In the same way as for the dose of the gene transporter, it may be selected as appropriate according to the severity of a disease, and the weight, age or gender of a patient, and may be increased or decreased as appropriate according to the degree of improvement.

For example, in actual treatment, the dose is set appropriately according to the types of antitumor substance precursor used and converted antitumor substance, the effective therapeutic dose of the antitumor substance converted from the antitumor substance precursor, the type of active protein produced by an anaerobic microorganism having the activity of converting the antitumor substance precursor into the antitumor substance, and the amount of active protein produced by the anaerobic microorganism used, etc.

Specifically, for example, when a pharmaceutical composition containing as an active component *Bifidobacterium longum* 105-A/pBifiCD (NITE BP-491) having a CD gene induced thereinto, which is a gene transporter of the present invention, and a pharmaceutical composition containing as an active component the antitumor substance precursor 5-FC are administered in combination, after it is confirmed that the bacteria have colonized and proliferated in tumor tissue and the bacteria have disappeared from blood and normal tissue, 5-FC is administered at 1 to 100 mg/day per kg weight of an adult once or a plurality of times per day successively during a treatment period. The administration method is preferably oral administration, but parenteral administration such as intravenous administration or anal administration may be carried out.

'In a combination of X and Y' referred to in the present invention includes a case in which X and Y are in different configurations and a case in which X and Y are in the same configuration (e.g. a configuration containing X and Y). When X and Y are in different configurations, X and Y may each further contain another component.

The pharmaceutical composition or the therapeutic agent for an anaerobic disease of the present invention may be applied to a disease that is in an anaerobic environment, and preferably to various types of solid cancers. Examples of the solid cancer include large bowel cancer, brain tumor, head and neck cancer, breast cancer, lung cancer, esophageal cancer, stomach cancer, liver cancer, gallbladder cancer, bile duct cancer, pancreatic cancer, islet cell cancer, chorionic cancer, colonic cancer, renal cell cancer, adrenal cortex cancer, bladder cancer, testicular cancer, prostate cancer, testicular tumor, ovarian cancer, uterine cancer, thyroid cancer, malignant carcinoid tumor, skin cancer, malignant melanoma, osteosarcoma, soft tissue sarcoma, neuroblastoma, Wilms' tumor, retinoblastoma, melanoma, and squamous cancer.

Furthermore, examples of other diseases that are in an anaerobic environment include ischemic diseases such as cardiac infarction or arteriosclerosis obliterans, and lower limb ischemic diseases such as Buerger's disease.

EXAMPLES

The present invention is explained more specifically below by reference to Reference Examples and Examples, but the technical scope of the present invention is not limited to these Examples.

Reference Example 1

Preparation of DNA Template
The concentration of plasmid DNA used as a template in each Example was adjusted to 10 pg/μL using 0.1×TE and stored in a freezer at −30° C. until use. Each plasmid DNA used as a template is shown in Table 1 below.

TABLE 1

Plasmid components and these roles in the new plasmid

| Plasmid Name | Component | Role in the new plasmid |
|---|---|---|
| pBLES100 | AAD 9 cassette | SPCM resistance gene (containing Spectinomysin adenyltransferase CDS, its promoter, ribosome binding region, terminator) |
| pBLES100 | pTB6 (OriV and RepB) | Replication unit in *Bifidobacterium longum* |
| pBluescript II SK+ | pUC ori | Replication origin in *Escherichia coli* |
| pAV001-HU-eCD-M968 | From HU promoter to HU terminator | CD gene (containing HU promoter, ribosome binding region, HU-eCD-M968 CDS, terminator) |

Reference Example 2

Preparation of Primer

Each primer used for PCR amplification and for checking was dissolved using 0.1×TE to give a 100 µM stock solution. This was further diluted with 0.1×TE to give a 20 µM primer solution. It was stored in a freezer at −30° C. until use. The primers used are shown in Table 2 below.

TABLE 2

Primers for construction and check of plasmids

| Primer name | Sequence (5'->3') | Purpose |
|---|---|---|
| pUCori_F1 | AGAGAGATCTTGAGCAAAAGGCCAG (SEQ ID NO: 5)<br>      BglII | Amplifying pUC ori |
| pUCori_R1 | GAGACTAGTGACTCGAGAAGGATCCGTAGAAAAGATCAAAGG<br>    Bcu I   Xho I   BamH I<br>(SEQ ID NO: 6) | |
| AAD9_F1 | AGAACTAGTAGAAAGCTTAGAGTCGACTCGATTTTCGTTCGTG<br>    Bcu I   Hind III   Sal I<br>(SEQ ID NO: 7) | Amplifying AAD9 cassette |
| AAD9_R1 | GAGAGATCTAAAAAAATTGAAAAAAGTGTTTCCACC<br>    Bgl II<br>(SEQ ID NO: 8) | |
| HUeCD_F3 | AAGAGGATCCGTCTTCCTGCTGGCCTATGC<br>    BamHI<br>(SEQ ID NO: 9) | Amplifying HU-eCD-M968 |
| HUeCD_R1 | AGAACTAGTCCGGAATAATACGGTTGGAC<br>    Bcu I<br>(SEQ ID NO: 10) | |
| HUeCD_inner_R1 | GCTACGAGCAGAAGGTCAACGTTTGTAATCGATGG<br>(SEQ ID NO: 11) | |
| HUeCD_inner_F1 | CGATTACAAACGTTGACCTTCTGCTCGTAGCGATTACTTCG<br>(SEQ ID NO: 12) | |
| OriV-Rep_outer_F1 | AGAACTAGTCCTCCAGGACCTCGTCTACG<br>    Bcu I<br>(SEQ ID NO: 13) | Amplifying OniV-Rep |
| OriV-Rep_outer_R1 | AGAGTCGACAAGCCCCGAACAGGTGAAGGC<br>    Sal I<br>(SEQ ID NO: 14) | |
| OriV-Rep_inner_F1 | CCGTTGAAGCCGGGGAGTGCCGTTTCTGCGCGTTTGAC<br>(SEQ ID NO: 15) | *1 |

TABLE 2-continued

Primers for construction and check of plasmids

| Primer name | Sequence (5'->3') | Purpose |
|---|---|---|
| OriV-Rep inner_R1 | GAAACGGCACTCCCCGGCTTCA<u>ACGGTGCCGTCGAAGTG</u> (SEQ ID NO: 16) | *1 |
| Check primer F1 | TGACTTAGAGGAATTACTACCTG (SEQ ID NO: 17) | |
| Check primer R2 | AAAGTGGCGGAAAGCGCCAC (SEQ ID NO: 18) | |

*1: Destroying putative ribosome binding site and putative translation start codon of memb B Reference Example 3

Agarose Gel Electrophoresis

Agarose gel electrophoresis in each Example below was carried out as follows.

A sample was diluted by on the order of 10 times using 0.1×TE as necessary and subjected to electrophoresis using 0.8% or 2% agarose gel for analysis and 1×TBE buffer (containing 0.5 µg/mL ethidium bromide). The concentration of the agarose gel was determined according to the size of the DNA sample. By subjecting a DNA molecular weight marker to electrophoresis at the same time in a different lane, the DNA size of the sample was checked.

When it was necessary to quantitatively measure a sample, a quantitative marker such as FastRuler DNA Ladder, Low Range (Fermentas), or FastRuler DNA Ladder, Middle Range (Fermentas) was used. The quantity of each band of the quantitative marker was on the order of 5 ng to 50 ng.

After the electrophoresis, the gel was irradiated with UV, and the DNA concentration of the sample was estimated by comparing the DNA concentration of the quantitative marker and that of the sample.

Example 1

Construction of Selection Marker Plasmid (pSPCM-pUCori) (Step 1)

The plasmid pSPCM-pUCori was constructed in accordance with the procedure below.

(1) Preparation of pUC Ori Fragment (about 700 bp)

Examination of Conditions for PCR Amplification of pUC Ori

Using pBluescript II SK+ as a template, a PCR mixture was prepared on ice by adding, to a sterilized 0.2 mL PCR tube (Bio-BIK), 5 µL of 10 pg/µL pBluescript II SK+, 10 µL of 5× PrimeStar™ buffer, 4 µL of a dNTP mixture (2.5 mM each), 0.5 µL of 20 µM pUCori-F1 primer, 0.5 µL of 20 µM pUCori-R1 primer, 0.5 µL of PrimeSTAR$^{Hs}$ DNA polymerase, and 29.5 µL of sterile purified water.

A thermal cycler was set up under the conditions below, after the block temperature reached 98° C. the tube was placed thereon, and PCR was carried out.

| Denature | 98° C. | 10 sec | |
|---|---|---|---|
| Anneal | 45° C. | 5 sec | ×30 cycles |
| Extension | 72° C. | 40 sec | |
| | 72° C. | 60 sec | |
| | 4° C. | ∞ | |

1 µL and 3 µL of the reaction mixture after the completion of PCR were subjected to the agarose gel electrophoresis presented in Reference Example 3, thus checking the PCR product. As the gel, 2% analytical agarose gel was used.

From the result of agarose gel analysis, it was confirmed that there was amplification of a target single band at about 700 bp, and the yield was about 1 µg.

Additional PCR

Additional PCR was carried out under the conditions set above for 5 tubes, and in total about 10 µg of PCR product was obtained.

Purification (Protein Removal and Concentration)

After all of the PCR reaction mixtures were combined, they were purified using a QIAquick PCR purification kit (Qiagen), and primer and protein were removed by a standard method. For DNA elution, 50 µL of 0.1×TE was used.

The purified PCR product was diluted by 10 times with 0.1×TE, and quantified using agarose gel electrophoresis. As the gel, 2% analytical agarose gel was used.

Treatment of PCR Product with Restriction Enzyme

The purified PCR product was cleaved as follows using restriction enzymes Bcu I and Bgl II.

10 µL of 10× Buffer O (buffer included with enzyme) and 55 units of Bgl II were added to 5 µg of the purified PCR product, and the total amount was made up to 100 µL using 0.1×TE. After incubating at 37° C. for 2 hours, protein was removed in accordance with a method described in Reference Example 4. 30 µL of 10× Buffer Tango (buffer included with enzyme) and 255 units of Bcu I were added thereto, and the total amount was made up to 300 µL using 0.1×TE. After incubating at 37° C. for 2 hours, the mixture was purified using a QiAquick PCR purification kit (Qiagen) and eluted with 50 µL of 0.1×TE.

Fractionation by Agarose Gel and Excision

The PCR product cleaved by the restriction enzyme and ⅒ of the amount thereof of 10× Loading buffer (Takara Bio Inc.) were mixed well to give a sample for electrophoresis. 2% agarose gel for purification was set in an electrophoresis vessel (Mupid, Cosmo Bio Co., Ltd.) charged with 1×TAE buffer (with 0.5 µg/mL of ethidium bromide), the electrophoresis sample was applied thereto, and electrophoresis was carried out at 50 V in a low temperature room (set at 4° C.). A molecular weight marker (FastRuler DNA ladder, Low Range, Fermentas) was run in a separate lane at the same time.

The DNA mobility was ascertained by irradiating the agarose gel with UV at 365 nm using a UV hand monitor (UVP). 130 minutes after starting electrophoresis, when a target band at about 700 bp reached a position about ½ way along the gel, the electrophoresis was ended, and the gel was taken out of the electrophoresis vessel.

While irradiating the gel with UV at 365 nm, the target DNA band was excised using a sterilized knife blade (Sterile Surgical Blades, Rüttgers HmbH & Co. KG). The excised gel was finely sliced and placed in a sterilized 2 mL microtube, whose weight was measured in advance.

DNA Elution from Agarose Gel

The weight of the 2 mL microtube with the excised gel was measured, and the gel weight was calculated by subtracting the pre-measured weight of the empty tube therefrom. DNA was extracted from the gel using a QIAquick Gel Extraction Kit in accordance with the product instructions. Elution of DNA in the final step employed 50 µL of 0.1×TE.

Part of the purified PCR product was diluted by 10 times with 0.1×TE, and the purified PCR product was quantitatively analyzed using a spectrophotometer. Agarose gel electrophoresis was carried out using 2% analytical agarose gel.

With regard to the DNA fragment subjected to the PCR product restriction enzyme treatment, the DNA fragment excision from the agarose gel, and purification, it was confirmed that it gave a single band in agarose gel analysis. Moreover, from the result of measuring concentration by DNA measurement using an absorptiometer, the concentration was 66 ng/µL. Moreover, the A260/280 ratio, which indicates the purity, was 1.911.

(2) Preparation of AAD 9 Fragment (about 1.1 kbp)

Examination of conditions for PCR amplification of AAD 9 gene Using pBLES100 as a template, a PCR mixture was prepared on ice by adding, to a sterilized 0.2 mL PCR tube (Bio-BIK), 5 µL of 10 pg/µL pBLES100, 10 µL of 5× PrimeStar™ buffer, 4 µL of a dNTP mixture (2.5 mM each), 0.5 µL of 20 µM AAD9-F1 primer, 0.5 µL of 20 µM AAD9-R1 primer, 0.5 µL of PrimeSTAR$^{Hs}$ DNA polymerase, and 29.5 µL of 0.1×TE.

A thermal cycler was set up under the conditions below, after the block temperature reached 98° C. the tube was placed thereon, and PCR was carried out.

| Denature | 98° C. | 10 sec | |
|---|---|---|---|
| Anneal | 45° C. | 5 sec | ×30 cycles |
| Extension | 72° C. | 60 sec | |
| | 72° C. | 60 sec | |
| | 4° C. | ∞ | |

1 µL and 3 µL of the reaction mixture after the completion of PCR were subjected to agarose gel electrophoresis, thus checking the PCR product. As the gel, 2% analytical agarose gel was used.

From the result of the agarose gel analysis, it was confirmed that there was amplification of a target single band at about 1.1 kbp. The yield was about 1 µg.

Additional PCR

In the same manner as above, additional PCR was carried out for 5 tubes, and in total about 10 µg of PCR product was obtained.

Purification (Protein Removal and Concentration)

After all of the PCR reaction mixtures were combined, they were purified using a QIAquick PCR purification kit, and primer and protein were removed by a standard method. For DNA elution, 50 µL of 0.1×TE was used.

The purified PCR product was diluted by 10 times with 0.1×TE, and quantified using agarose gel electrophoresis. As the gel, 2% analytical agarose gel was used.

Treatment of PCR Product with Restriction Enzyme

The purified PCR product was cleaved as follows using restriction enzymes Bcu I and Bgl II.

10 µL of 10× Buffer O (buffer included with enzyme) and 36 units of Bgl II were added to 5 µg of the purified PCR product, and the total amount was made up to 100 µL using 0.1×TE. After incubating at 37° C. for 2 hours, protein was removed. 30 µL of 10× Buffer Tango (buffer included with enzyme) and 165 units of Bcu I were added thereto, and the total amount was made up to 300 µL using 0.1×TE. After incubating at 37° C. for 2 hours, the mixture was purified using a QIAquick PCR purification kit and eluted with 50 µL of 0.1×TE.

Fractionation by Agarose Gel and Excision

The PCR product cleaved by the restriction enzyme was fractionated by subjecting it to electrophoresis for 130 minutes by the same method as in the above-mentioned 'Fractionation by agarose gel and excision', and a target band at about 1.1 kbp was excised. As the gel, 0.8% agarose gel for purification was used.

DNA Elution from Agarose Gel

The weight of the 2 mL microtube with the excised gel was measured, and the gel weight was calculated by subtracting the pre-measured weight of the empty tube therefrom. DNA was extracted from the gel using a QIAquick Gel Extraction Kit in accordance with the product instructions. Elution of DNA in the final step employed 50 µL of 0.1×TE.

Part of the purified PCR product was diluted by 10 times with 0.1×TE, and the purified PCR product was quantitatively analyzed using a spectrophotometer. Electrophoresis was carried out using 2% analytical agarose gel.

With regard to the DNA fragment subjected to the PCR product restriction enzyme treatment, DNA fragment excision from the agarose gel, and purification, it was confirmed that it gave a single band in agarose gel analysis. Moreover, from the result of measuring concentration by DNA measurement using an absorptiometer, the concentration was 40 ng/µL. Moreover, the A260/280 ratio, which indicates the purity, was 1.927.

(3) Ligation of pUC Ori Fragment and AAD 9 Fragment

A ligation reaction mixture (reaction mixture 1) was prepared by mixing on ice, in a sterilized 0.2 mL PCR tube (Bio-BIK), 4 µL of 5× Rapid Ligation Buffer, 0.75 µL (50 ng) of pUC ori fragment (66 ng/µL), 6.25 µL (250 ng) of AAD 9 fragment (40 ng/µL), 1 µL of 5 u/µL T4 DNA Ligase, and 8 µL of 0.1×TE so that the molar ratio of the purified pUC ori fragment (about 700 bp) to the purified AAD9 fragment (about 1.1 kbp) was 1:3 and the ratio by weight thereof was 1:5.

As a control, a reaction mixture (reaction mixture 2) was prepared with only the purified AAD9 fragment. That is, 4 µL of 5× Rapid Ligation Buffer, 6.25 µL (250 ng) of AAD 9 fragment (40 ng/µL), 1 µL of 5 u/µL T4 DNA Ligase, and 8.75 µL of 0.1×TE were mixed on ice, thus giving a ligation reaction mixture (reaction mixture 2).

Since the AAD 9 fragment uses plasmid pBLES100 (Patent Publication 4: JP, A, 2002-97144) as a template, even when a small amount thereof is added, it forms a colony as a background after the subsequent step of transforming E. coli. Reaction mixture 2 was used as a control for checking this background.

A thermal cycler was set up under the conditions below, after the block temperature reached 22° C. the tube was placed thereon, and ligation was carried out.

| 22° C. | 5 min (ligation reaction) |
|---|---|
| 65° C. | 5 min (reaction stopped) |
| 4° C. | ∞ |

(4) Transformation of E. coli

Transformation of E. coli JM109 was carried out by heat shock using 1 μL of a solution after the ligation reaction. The operating procedure for the transformation was carried out in accordance with a method described in the product instructions of Takara E. coli JM109 Competent Cells (Takara Bio Inc.). With regard to an SOC suspension after transformation, 100 μL of the original liquid and 100 μL of a 10 times dilution by SOC were plated onto two LB agar media (containing 75 μg/mL SPCM). Plates inoculated with E. coli transformed using ligation reaction mixtures 1 and 2 were defined as plates 1 and 2 respectively. These plates were placed in an incubator set at 37° C. and cultured overnight. The numbers of colonies formed on the plates were counted.

When transformation was carried out using the ligation product of the purified pUC ori fragment and the purified AAD9 fragment (ligation reaction mixture 1), 28 and 37 colonies were formed on the selective media per 100 μL of the 10 times dilution bacterial liquid, but when transformation was carried out using reaction mixture 2 of the control, no colonies were formed. The background was very low, suggesting that ligation and transformation were carried out well.

(5) Checking Plasmid

Culturing of Recombinant E. coli 6 colonies on plate 1 above were selected randomly, and culturing was carried out using them. A sterilized 100 mL glass Erlenmeyer flask was charged with 20 mL of 2×LB, and 20 μL of 75 mg/mL spectinomycin was added thereto and mixed well. Each colony was fished using a platinum loop and suspended in the above-mentioned media. They were set in a shaking incubator set at 37° C. and cultured while shaking at 37° C. for 19.5 hours.

Extraction of Plasmid DNA 1.5 mL of each culture fluid was placed in two sterilized 2 mL microtubes. The remaining culture fluids were left in ice until extraction of plasmid was completed. Plasmid DNA was extracted from the dispensed culture fluid using a GeneElute™ Plasmid Miniprep Kit in accordance with the product instructions for the kit. For elution of plasmid DNA in the final step, 50 μL of 0.1×TE was used.

Measurement of Concentration of Plasmid DNA

The plasmid extracted above was diluted by 20 times with 0.1×TE, the DNA concentration was measured by a spectrophotometer, and the quality was checked by the A260/280 ratio.

From the results of carrying out extraction of plasmid DNA from recombinant E. coli twice, the A260/280 ratio, which indicates the purity of DNA, was 1.944 to 1.972, and the purity of the plasmid DNA was good. The yield was at least 5 μg when combining the two extracts.

Cleavage by Restriction Enzyme

Cleavage by Bcu I on its own, cleavage by Bgl II on its own, and cleavage by both Bcu I and Bgl II were carried out using 100 ng of plasmid DNA. The reaction conditions were in accordance with the product instructions for the enzymes. The reaction volume was 20 μL.

For all 6 colony strains, two bands at about 700 bp and about 1.1 kbp were detected when cleavage was carried out by the two types of enzymes Bcu I and Bgl II.

Furthermore, one band at about 1.8 kbp was detected when cleavage was carried out by a single enzyme of Bcu I or Bgl II. This suggests that for all strains the plasmid size and constitution were as designed.

Checking Plasmid DNA Sequence

20 μL of the plasmid DNA solution cleaved by the restriction enzyme above was mixed well with 2 μL of 10× Loading buffer, and this mixture was subjected to electrophoresis by a standard method.

A sequence reaction was carried out using a BigDye Terminator v3.1 Cycle Sequencing Kit using the plasmid extracted by the above electrophoresis. As a sequence primer, primer sets 1 and 2 shown in Table 3 below were used.

Alignment of the sequence was carried out using GENETY® ATSQ analysis software (Genetyx Corporation). The plasmid nucleotide sequence after alignment was compared with the designed sequence (SEQ ID NO: 1).

Among the 6 strains, the plasmid sequence of 4 strains matched that of the designed SEQ ID NO: 1, but the remaining 2 plasmid strains had nucleotide substitution and deletion respectively.

One strain was selected from the 4 strains that matched SEQ ID NO: 1, and a plasmid extracted from this strain was defined as 'pSPCM-pUCori'.

TABLE 3

Primers for sequencing

| Primer name | Sequence (5'->3') | Set |
|---|---|---|
| 37_R_5181 | AAA TAT CTC TTG CCA GTC AC (SEQ ID NO: 19) | Set 1 |
| 060723-spmsec | CAT GTT TGG ATC AGG AGT TGA G (SEQ ID NO: 20) | Set 1 |
| 41_F-seq13 | AGC AAG AAA TGG TAC CGT GG (SEQ ID NO: 21) | Set 1 |
| 060219-pAV001-2 | TTT GCT TGG TAA AGC ATT ATG G (SEQ ID NO: 22) | Set 1 |
| 42_F-seq_28down | GAC TTA GAG GAA TTA CTA CC (SEQ ID NO: 23) | Set 1 |
| 38_F_5980 | ATA CCA AAA GAT ATT GCG GG (SEQ ID NO: 24) | Set 1 |
| 060723-spmsec | AAT GGA GAA GAT TCA GCC ACT G (SEQ ID NO: 25) | Set 1 |
| pUC ori-1 | AAG GCC AGC AAA AGG C (SEQ ID NO: 26) | Set 2 |

TABLE 3-continued

Primers for sequencing

| Primer name | Sequence (5'->3') | Set |
|---|---|---|
| 060219-pAV001-3 | GAC GAT AGT TAC CGG ATA AGG C (SEQ ID NO: 27) | Set 2 |
| 060219-pAV001-3 | GCC TTA TCC GGT AAC TAT CGT C (SEQ ID NO: 28) | Set 2 |
| 40_R-seq_16down | ATT AGC AGA GCG AGG TAT GT (SEQ ID NO: 29) | Set 2 |
| 39_R_6495 | GCA AGC AGC AGA TTA CGC GC (SEQ ID NO: 30) | Set 2 |
| HUIV (F) | AGT GCC GCA GGG CGT (SEQ ID NO: 31) | Set 3 |
| HUIV (R) | ACG CCC TGC GGC ACT (SEQ ID NO: 32) | Set 3 |
| 060403_HU upstream cloning | TTT GCT TAG TCC ATG TTG TCA TCA (SEQ ID NO: 33) | Set 3 |
| pAVeCD1482_atg | ATG GCA TAC AAC AAG TCT GAC CTC (SEQ ID NO: 34) | Set 3 |
| CD seq (F) | GCG CAT GGC AAA CGC TGA AAT GGC AGA TTG (SEQ ID NO: 35) | Set 3 |
| CD seq (R) | GTG ATG CCG CGA CGT TTT GGA TAC GTA TCG (SEQ ID NO: 36) | Set 3 |
| CD892_D314A | CGC GTT AAA GAG ATG CTG GAG T (SEQ ID NO: 37) | Set 3 |
| R-pTB6 R7 | GTC TGG GGA GTC CTG CGT TC (SEQ ID NO: 38) | Set 4 |
| pBLES100 F3 | TAT GCT GAG GCC ATG TCC AAT GAG A (SEQ ID NO: 39) | Set 4 |
| R-pTB6 R6 | GTC AGG TCG TTG AGC AGG AAC (SEQ ID NO: 40) | Set 4 |
| pTB6 F5 (pBLES100 F5) | GAA GAT CGA GCG CCA GTA CGT GAA (SEQ ID NO: 41) | Set 4 |
| 060219-pAV001-1 | GTG AAC ACC TCG CCG TAC C (SEQ ID NO: 42) | Set 4 |
| 36_F_4754 | CAA CCG CGA ACA TCA TGC GC (SEQ ID NO: 43) | Set 4 |

Example 2

Construction of Selection Marker Activity Protein Plasmid (pHU-eCDm-SPCM-pUCori) (Step 2)

(1) Preparation of Linear Plasmid pSPCM-pUCori

Cleavage of Plasmid pSPCM-pUCori was cleaved as described below using the restriction enzymes Bcu I, Xho I, and Bam HI. Cleavage by Xho I was carried out in order to suppress the background during transformation by uncleaved plasmid.

25 μL of 10× Buffer Tango (buffer included with enzyme) and 100 units of Bcu I were added to 5 μg of pSPCM-pUCori, and the total amount was made up to 250 μL using 0.1×TE. After incubating at 37° C. for 2 hours, 100 ng thereof was taken out, and it was confirmed using 0.8% analytical agarose gel that decomposition was completed.

The tube containing the enzyme reaction mixture was stored on ice while waiting for confirmation. After cleavage was confirmed, protein was removed from the enzyme reaction mixture.

20 μL of 10× Buffer Bam HI (buffer included with enzyme) and 80 units of Bam HI were added thereto, and the total amount was made up to 200 μL using 0.1×TE. After incubating at 37° C. for 2 hours, 100 ng thereof was taken out, and it was confirmed using 0.8% analytical agarose gel that DNA had not undergone internal decomposition.

The tube containing the enzyme reaction mixture was stored on ice while waiting for confirmation. After cleavage was confirmed, protein was removed from the enzyme reaction mixture.

50 μL of 10× Buffer R (buffer included with enzyme) and 400 units of Xho I were added thereto, and the total amount was made up to 500 μL using 0.1×TE. After incubating at 37° C. for 2 hours, protein was removed from the enzyme reaction mixture.

Fractionation by Agarose Gel and Excision

The vector cleaved by the restriction enzyme was fractionated by subjecting it to electrophoresis for 75 minutes by the same method as in 'Fractionation by agarose gel and excision' described in Example 1, and a target band at about 1.8 kbp was excised. As a gel, 0.8% agarose gel for purification was used. As a molecular weight marker, FastRuler DNA ladder, Middle Range (Fermentas) was used.

DNA Elution from Agarose Gel

DNA was eluted from the gel excised above by the same method as in 'DNA elution from agarose gel' described in Example 1.

Part of the vector subjected to the agarose gel purification was diluted by 3 times using 0.1×TE, and quantitatively analyzed by a spectrophotometer. It was checked using 0.8% analytical agarose gel as to whether or not the vector prepared was a single band at about 1.8 kbp.

With regard to the DNA fragment subjected to the plasmid pSPCM-pUCori restriction enzyme treatment, DNA fragment excision from the agarose gel, and purification, it was confirmed that it gave a single band in agarose gel analysis. In DNA measurement using an absorptiometer, the concentration was 21 ng/μL. Moreover, the A260/280 ratio, which indicates the purity, was 2.049.

(2) Preparation Of Insert (HU-eCD Fragment)

Using plasmid pAV001-HU-eCD-M968 (Patent Publication 5: WO 2007/136107), a DNA fragment containing HU-eCD-M968 (a protein in which the N-terminal 9 amino acids of an HU protein of *Bifidobacterium* and *E. coli*-derived CD were fused, and into which a variation was introduced for enhancing the affinity for substrate 5-FC), an HU promoter, and an HU terminator was amplified by PCR.

Two stage PCR (1st PCR and 2nd PCR) was carried out as follows, and an HU-eCD fragment was prepared.

1st PCR

Examination of Conditions for PCR Amplification

PCR amplification conditions were examined for two types of fragments (HU-eCD fragment 1 and HU-eCD fragment 2).

Using pAV001-HU-eCD-M968 as a template, a PCR mixture (HU-eCD fragment 1) was prepared on ice by adding to a sterilized 0.2 mL PCR tube (Bio-BIK) 5 μL of 10 pg/mL pAV001-HU-eCD-M968, 10 μL of 5× PrimeStar™ buffer, 4 μL of a dNTP mixture (2.5 mM each), 0.5 μL of 20 μM HUeCD F3 primer, 0.5 μL of 20 μM HUeCD inner R1 primer, 0.5 μL of PrimeSTAR$^{Hs}$ DNA polymerase, and 29.5 μL of 0.1×TE. 3 tubes of this mixture were prepared in the same manner.

A thermal cycler was set up under the conditions below, after the block temperature reached 98° C. the tubes were placed thereon, and PCR was carried out.

| Denature | 98° C. | 10 sec | |
|---|---|---|---|
| Anneal | 55° C. | 5 sec | ] ×30 cycles |
| Extension | 72° C. | 100 sec | |
| | 72° C. | 60 sec | |
| | 4° C. | ∞ | |

In the same manner, using pAV001-HU-eCD-M968 as a template, a PCR mixture (HU-eCD fragment 2) was prepared on ice by adding to a sterilized 0.2 mL PCR tube (Bio-BIK) 5 μL of 10 pg/mL pAV001-HU-eCD-M968, 10 μL of 5× PrimeStar™ buffer, 4 μL of a dNTP mixture (2.5 mM each), 0.5 μL of 20 μM HUeCD inner F1 primer, 0.5 μL of 20 μM HUeCD R1 primer, 0.5 μL of PrimeSTAR$^{Hs}$ DNA polymerase, and 29.5 μL of 0.1×TE. 8 tubes of this mixture were prepared in the same manner.

In the same manner, a thermal cycler was set up under the conditions below, after the block temperature reached 98° C. the tubes were placed thereon, and PCR was carried out.

| Denature | 98° C. | 10 sec | |
|---|---|---|---|
| Anneal | 55° C. | 5 sec | ] ×30 cycles |
| Extension | 72° C. | 6 sec | |
| | 72° C. | 60 sec | |
| | 4° C. | ∞ | |

After completion of PCR, the reaction mixtures were combined in one tube.

The PCR product was checked using 1 μL and 3 μL of the reaction mixture after completion of PCR. For checking HU-eCD fragments 1 and 2, 0.8% analytical agarose gel and 2% analytical agarose gel were used respectively.

From the result of agarose gel analysis of the PCR product of HUeCD fragment 1, it was confirmed that there was amplification of a target single band at about 1.7 kbp. The yield was at least 4.5 μg.

Furthermore, in agarose gel analysis of the PCR product of HUeCD fragment 2, it was confirmed that there was amplification of a target single band at about 150 bp. The yield was about 8 μg.

Purification by PCR Purification Kit

The PCR product was subjected to purification in accordance with the procedural manual for the QIAquick PCR purification kit, thus removing the primer. Elution of DNA in the final step of the purification employed 50 μL of 0.1×TE.

Fractionation by Agarose Gel and Excision of PCR Product

The purified PCR product was fractionated by the same method as in the above-mentioned 'Fractionation by agarose gel and excision'. HU-eCD fragment 1 was subjected to electrophoresis for 65 minutes using 0.8% agarose gel for purification, and a target band at about 1.7 kbp was excised. HU-eCD fragment 2 was subjected to electrophoresis for 65 minutes using 2% agarose gel for purification, and a target band at about 150 bp was excised.

DNA Elution from Agarose Gel

DNA was eluted from the gel excised above by the same method as in the 'DNA elution from agarose gel' above.

Quantitative Analysis of Purified PCR Product

Part of the purified PCR product was diluted by 3 times using 0.1×TE, and quantitatively analyzed by a spectrophotometer. The concentration of HU-eCD fragment 1 and the concentration of HU-eCD fragment 2 were both 47 ng/μL, and the yield was about 2.3 μg.

2nd PCR

Examination of Conditions for PCR Amplification

The purified HU-eCD fragment 1 and purified HU-eCD fragment 2 were used as a template, and PCR conditions for connecting them were examined.

Preparation of Template 517 ng of purified HU-eCD fragment 1 (about 1.7 kbp) and 47 ng of purified HU-eCD fragment 2 (about 150 bp) were mixed, and the concentration was adjusted to 1 ng/μL using 0.1×TE. The molar ratio of the two fragments was 1:1.

Preparation of Primer Mixture

10 μL of 20 μM HUeCD F3 primer and 10 μL of 20 μM HUeCD R1 primer were mixed in equal amounts.

Preparation of PCR Mixture

1 μL of the 1 ng/μL Hu-eCD fragment 1 and 2 mix, 10 μL of 5× PrimeStar™ buffer, 4 μL of a dNTP mixture (2.5 mM each), 0.5 μL of PrimeSTAR$^{Hs}$ DNA polymerase, and 32.5 μL of 0.1× TE were added to a sterilized 0.2 mL PCR tube (Bio-BIK), and mixing was carried out on ice, thus giving a PCR reaction mixture. Three tubes with this reaction mixture were prepared in the same manner.

A thermal cycler was set up under the conditions below, after the block temperature reached 98° C. the tubes were placed thereon, a cycle of 98° C. for 10 sec and 72° C. for 100 sec was carried out for five cycles, 2 μL of the primer mixture prepared above was then added and mixed therewith at 72° C., and the reaction below was carried out in the thermal cycler. After the reaction was completed, the reaction mixtures in the three PCR tubes were combined into one tube.

| Denature | 98° C. | 10 sec | |
|---|---|---|---|
| Anneal | 60° C. | 5 sec | ×30 cycles |
| Extension | 72° C. | 100 sec | |
| | 72° C. | 60 sec | |
| | 4° C. | ∞ | |

1 μL and 3 μL of the reaction mixture after the PCR was completed were subjected to electrophoresis using 0.8% analytical agarose gel and 1×TBE buffer (0.5 μg/mL ethidium bromide).

It was confirmed by agarose gel analysis of the 2nd PCR fragment that there was amplification of a target single band at about 1.8 kbp. The yield was about 13 μg.

Purification by PCR Purification Kit

The PCR product was subjected to purification in accordance with the procedural manual for the QIAquick PCR purification kit, thus removing the primer. Elution of DNA in the final step of the purification employed 50 μL of 0.1×TE.

Part of the PCR product from which the primer was removed was diluted by 50 times with 0.1×TE, and quantitatively analyzed by a spectrophotometer.

Treatment of PCR Product with Restriction Enzyme

The purified PCR product was cleaved using the restriction enzymes Bcu I and Bam HI.

25 μL of 10× Buffer Tango (buffer included with enzyme) and 100 units of Bcu I were added to 5 μg of purified PCR product, and the total amount was made up to 250 μL using 0.1×TE. After incubating at 37° C. for 2 hours, 100 ng thereof was taken out, and it was confirmed using 0.8% analytical agarose gel that DNA had not undergone internal decomposition.

The tube containing the enzyme reaction mixture was stored on ice while waiting for confirmation. After carrying out confirmation by electrophoresis, protein was removed from the enzyme reaction mixture.

20 μL of 10× Buffer Bam HI (buffer included with enzyme) and 80 units of Bam HI were added thereto, and the total amount was made up to 200 μL using 0.1×TE. After incubating at 37° C. for 2 hours, 100 ng thereof was taken out, and it was confirmed using 0.8% analytical agarose gel that DNA had not undergone internal decomposition.

The tube containing the enzyme reaction mixture was stored on ice while waiting for confirmation. After carrying out confirmation by electrophoresis, this enzyme reaction mixture was purified using a QIAquick PCR Purification Kit.

Fractionation by Agarose Gel and Excision

The PCR product cleaved by the restriction enzyme was fractionated by the same method as in the above-mentioned 'Fractionation by agarose gel and excision', and a target band at about 1.8 kbp was excised. As the gel, 0.8% agarose gel for purification was used, and 75 minutes after starting electrophoresis, when a target band at about 1.8 kbp reached a position about ⅓ of the way along the gel, the electrophoresis was ended. As a DNA molecular weight marker, FastRuler DNA ladder, Middle Range (Fermentas) was used.

DNA Elution from Agarose Gel

DNA was eluted from the gel excised above by the same method as in the 'DNA elution from agarose gel' above.

Part of the PCR product subjected to the agarose gel purification was diluted by 3 times using 0.1×TE, and quantitatively analyzed by a spectrophotometer. Confirmation by electrophoresis was carried out using 0.8% analytical agarose gel.

After the PCR product was subjected to the restriction enzyme treatment and the agarose gel purification, the DNA concentration was measured by an absorptiometer and was found to be 41 ng/μL. Moreover, the A260/280 ratio, which indicates the purity, was 1.932. Furthermore, in electrophoresis analysis using agarose gel, there was a single band at about 1.8 kbp.

(3) Ligation of Linear pSPCM-pUCori and HU-eCD Fragment

A ligation reaction mixture (reaction mixture 1) and control reaction mixtures (reaction mixture 2 and reaction mixture 3) were prepared as follows.

Reaction Mixture 1

4 μL of 5× Rapid Ligation Buffer, 2.4 μL (50 ng) of pSPCM-pUCori (21 ng/μL), 3.7 μL (150 ng) of HU-eCD fragment (41 ng/μL), 1 μL of 5 u/μL T4 DNA Ligase, and 8.9 μL of 0.1×TE were added to a 0.2 mL PCR tube (Bio-BIK) so that the molar ratio of the linear pSPCM-pUCori (about 1.8 kbp) to the HU-eCD fragment (about 1.8 kbp) was 1:3 (also 1:3 as a ratio by weight), and mixing was carried out on ice, thus giving a ligation reaction mixture (reaction mixture 1).

Reaction Mixture 2

Similarly, 4 μL of 5× Rapid Ligation Buffer, 2.4 μL (50 ng) of pSPCM-pUCori (21 ng/μL), 1 μL of 5u/μL T4 DNA Ligase, and 12.6 μL of 0.1×TE were added to a 0.2 mL PCR tube (Bio-BIK), and mixing was carried out on ice, thus giving a reaction mixture with only pSPCM-pUCori (reaction mixture 2).

Reaction Mixture 3

Similarly, 4 μL of 5× Rapid Ligation Buffer, 3.7 μL (150 ng) of HU-eCD fragment (41 ng/μL), 1 μL of 5u/μL T4 DNA Ligase, and 11.3 μL of 0.1×TE were added to a 0.2 mL PCR tube (Bio-BIK), and mixing was carried out on ice, thus giving a reaction mixture with only HU-eCD fragment (reaction mixture 3).

A thermal cycler was set up under the conditions below, after the block temperature reached 22° C. the tubes were placed thereon, and ligation was carried out.

| 22° C. | 5 min (ligation reaction) |
|---|---|
| 65° C. | 5 min (reaction stopped) |
| 4° C. | ∞ |

The proportion of the background due to plasmid remaining after cleavage was estimated using reaction mixture 2 and reaction mixture 3.

(4) Transformation of E. coli

Transformation of E. coli JM109 was carried out using 1 μL of the solution after the ligation reaction by the same method as in 'Transformation of E. coli' described in Example 1.

In transformation using the ligation product of the vector and the insert (ligation reaction mixture 1), 34 to 38 colonies were formed on a selective medium per 100 μL of 10 times dilution bacterial liquid, whereas in transformation using control reaction mixture 2 in which only the vector was ligated and control reaction mixture 3 in which only the insert was ligated there was 0 to 1 colony. The background was very low, suggesting that ligation and transformation were carried out well.

(5) Checking of Plasmid

Culturing of Recombinant *E coli*

Carried out in accordance with the method described in the section 'Culturing of recombinant *E. coli*' described in Example 1. Culturing was carried out for 20.5 hours.

Extraction of Plasmid DNA

Carried out in accordance with the method described in the section 'Extraction of plasmid DNA' described in Example 1.

Measurement of Concentration of Plasmid DNA

Carried out in accordance with the method described in the section 'Measurement of concentration of plasmid DNA' described in Example 1.

When the concentrations of DNA extracted from the recombinant *E. coli* of all six cloning strains were measured, the A260/280 ratio, which indicates the purity of the DNA, was from 1.904 to 1.916, and the purity of the plasmid DNA was good. The yield was at least 5 µg.

Cleavage by Restriction Enzyme

Cleavage by Bcu I on its own, cleavage by Bam HI on its own, and cleavage by both Bcu I and Bam HI were carried out using 100 ng of plasmid DNA. The reaction conditions were in accordance with the product instructions for the enzymes. The reaction volume was 20 µL.

Agarose Gel Electrophoresis

Agarose gel electrophoresis was carried out using 0.8% analytical agarose gel.

With regard to all six of the cloning strains, one band at about 1.8 kbp was detected from cleavage with the two types of enzymes Bcu I and Bam HI. Furthermore, one band at about 3.6 kbp was detected from cleavage with enzyme Bcu I on its own or Bam HI on its own. This suggests that for all the cloning strains the plasmid size and constitution were as designed.

Checking Plasmid DNA Sequence

Sequencing was carried out using the plasmid extracted above by the same method as in the section 'Checking plasmid DNA sequence' described in Example 1. As a primer, primer sets 1, 2, and 3 in Table 3 described in Example 1 were used. The plasmid nucleotide sequence after alignment was compared with the designed sequence (SEQ ID NO:2).

The plasmid sequences of all six cloning strains matched SEQ ID NO:2, and it was confirmed that the target strains were obtained in all cases. One strain was selected from all the cloning strains, and a plasmid extracted from this strain was defined as 'pHU-eCDm-SPCM-pUCori'.

Example 3

Construction of Shuttle Plasmid (pCDshuttle) (Step 3)

(1) Preparation of Linear Plasmid pHU-eCDm-SPCM-pUCori

Cleavage of Plasmid pHU-eCDm-SPCM-pUCori was cleaved as follows using restriction enzymes Bcu I, Hind III, and Sal I. Cleavage by Hind III was carried out in order to suppress the background when transforming in a subsequent step.

10 µL of 10× Buffer O (buffer included with enzyme) and 34 units of Sal I were added to 5 µg of pHU-eCDm-SPCM-pUCori, and the total amount was made up to 100 µL using 0.1×TE. After incubating at 37° C. for 6 hours, 50 ng thereof was taken out, and it was confirmed using 0.8% analytical agarose gel that decomposition was complete.

The tube containing the enzyme reaction mixture was stored on ice while waiting for confirmation. After cleavage by Sal I was confirmed, this enzyme reaction mixture was purified using a QIAquick PCR Purification Kit.

20 µL of 10× Buffer Tango (buffer included with enzyme) and 50 units of Bcu I were added thereto, and the total amount was made up to 200 µL using 0.1×TE. After incubating at 37° C. for 2 hours, protein was removed.

10 µL of 10× Buffer R (buffer included with enzyme) and 29 units of Hind III were added thereto, and the total amount was made up to 100 µL using 0.1×TE. After incubating at 37° C. for 2 hours, the DNA solution was purified and concentrated using a QIAquick PCR purification Kit.

Fractionation by Agarose Gel and Excision

The vector cleaved by the restriction enzyme was fractionated by the same method as in 'Fractionation by agarose gel and excision' described in Example 1, and a target band at about 3.6 kbp was excised. Electrophoresis was carried out at 50 V for 90 minutes using 0.8% agarose gel for purification. As a molecular weight marker, Quick-Load 1 kbp DNA ladder (NEB) was used.

DNA Elution from Agarose Gel

DNA was eluted from the gel excised above by the same method as in 'DNA elution from agarose gel' described in Example 1.

Part of the vector subjected to the agarose gel purification was diluted by 3 times with 0.1×TE and quantitatively analyzed by a spectrophotometer.

When the absorbance of the DNA fragment after the treatment of plasmid pHU-eCDm-SPCM-pUCori with the restriction enzyme and the purification by agarose gel was measured, the concentration was 13 ng/µL. Furthermore, the A260/280 ratio, which indicates the purity, was 1.961.

(2) Preparation of OriV-RepB Gene (Insert)

In pBLES100 used as a PCR template, the C-terminal region of the ORF of RepB gene and the N-terminal region of the ORF of the assumed membB gene were duplicated. In order to prevent the ORF of membB from being translated, the assumed ribosome binding site and translation initiation codon ATG of membB were changed to other nucleotides. In this case, the design was such that the amino acids of RepB were unchanged. Two-stage PCR (1st PCR and 2nd PCR) was carried out as follows, thus giving an OriV-RepB gene.

1st PCR

Examination of Conditions for PCR Amplification

PCR amplification conditions were examined for two types of fragments (OriV-RepB gene 1 and OriV-RepB gene 2).

OriV-RepB Gene 1

Using pBLES100 as a template, a PCR mixture was prepared on ice by adding 5 µL of 10 pg/mL pBLES100, 10 µL of 5× PrimeStar™ buffer, 4 µL of a dNTP mixture (2.5 mM each), 0.5 µL of 20 µM OriV-rep outer F1 primer, 0.5 µL of 20 µM OriV-rep inner R1 primer, 0.5 µL of PrimeSTAR$^{HS}$ DNA polymerase, and 29.5 µL of 0.1×TE to a sterilized 0.2 mL PCR tube (Bio-BIK). Three tubes of this mixture were prepared in the same manner.

A thermal cycler was set up under the conditions below, after the block temperature reached 98° C. the tubes were placed thereon, and PCR was carried out.

| Denature | 98° C. | 10 sec | ] x30 cycles |
|---|---|---|---|
| Anneal | 55° C. | 5 sec | |

-continued

| Extension | 72° C. | 60 sec |
|---|---|---|
| | 72° C. | 60 sec |
| | 4° C. | ∞ |

OriV-RepB Gene 2

In the same manner, using pBLES100 as a template, a PCR mixture was prepared on ice by adding 5 µL of 10 pg/mL pBLES100, 10 µL of 5× PrimeStar™ buffer, 4 µL of a dNTP mixture (2.5 mM each), 0.5 µL of 20 µM OriV-rep inner F1 primer, 0.5 µL of 20 µM OriV-rep outer R1 primer, 0.5 µL of PrimeSTAR$^{HS}$ DNA polymerase, and 29.5 µL of 0.1×TE to a sterilized 0.2 mL PCR tube (Bio-BIK). Three tubes of this mixture were prepared in the same manner.

A thermal cycler was set up under the conditions below, after the block temperature reached 98° C. the tubes were placed thereon, and PCR was carried out.

| Denature | 98° C. | 10 sec | |
|---|---|---|---|
| Anneal | 60° C. | 5 sec | ×30 cycles |
| Extension | 72° C. | 25 sec | |
| | 72° C. | 60 sec | |
| | 4° C. | ∞ | |

The PCR products were checked and the yields thereof were estimated using 1 µL of each of the reaction mixtures after PCR was completed. As a gel, 2% analytical agarose gel was used.

From the result of agarose gel analysis of the PCR product of OriV-RepB gene 1, it was confirmed that there was amplification of a target single band at about 1.3 kbp. The yield was about 4.5 µg.

Furthermore, in agarose gel analysis of the PCR product of OriV-RepB gene 2 it was confirmed that there was amplification of a target single band at about 400 bp, and the yield was about 4.5 µg.

Purification by PCR Purification Kit

The PCR products were purified and concentrated in accordance with a standard method (the operational procedure of a QIAquick PCR purification kit).

Fractionation by Agarose Gel and Excision of PCR Product

The PCR product purified and concentrated above was fractionated by the same method as in 'Fractionation by agarose gel and excision' described in Example 1. With respect to OriV-RepB gene 1, electrophoresis was carried out for 80 minutes using 0.8% agarose gel for purification. When a target band at about 1.3 kbp reached a position about ½ way along the gel, electrophoresis was ended. As a molecular weight marker, FastRuler DNA ladder, Middle Range was used. On the other hand, with respect to OriV-RepB gene 2, electrophoresis was carried out for 80 minutes using 2% agarose gel for purification. When a target band at about 400 bp reached a position about ½ way along the gel, electrophoresis was ended. As a molecular weight marker, FastRuler DNA ladder, Low Range was used.

DNA Elution from Agarose Gel

DNA was eluted from the gel excised above by the same method as in 'DNA elution from agarose gel' described in Example 1.

Quantitative Analysis of Purified PCR Product

Part of the purified PCR product was diluted by 4 times with 0.1×TE, and quantitatively analyzed using a spectrophotometer.

When the PCR product after the agarose gel purification was subjected to measurement using an absorptiometer, the concentrations of OriV-RepB gene 1 and OriV-RepB gene 2 were 37 ng/µL and 67 ng/µL respectively.

2nd PCR

Examination of Conditions for PCR Amplification

The purified OriV-RepB fragment 1 and purified OriV-RepB fragment 2 were used as a template, and PCR conditions for connecting them were examined.

Preparation of Template 325 ng of purified OriV-RepB fragment 1 (about 1.3 kbp) and 100 ng of purified OriV-RepB fragment 2 (about 400 bp) were mixed, and the concentration was adjusted to 1 ng/µL using 0.1×TE. The mixing ratio of purified OriV-RepB fragment 1 to purified OriV-RepB fragment 2 was 1:1 as a molar ratio.

Preparation of Primer Mixture

20 µM OriV-rep outer F1 primer and 20 µM OriV-rep outer R1 primer were mixed in equal amounts.

Preparation of PCR Mixture

A reaction mixture was prepared by adding 1 µL of the 1 ng/µL OriV-RepB 1 and 2 mix, 10 µL of 5× PrimeStar™ buffer, 4 µL of a dNTP mixture (2.5 mM each), 0.5 µL of PrimeSTAR$^{HS}$ DNA polymerase, and 32.5 µL of 0.1×TE to a sterilized 0.2 mL PCR tube (Bio-BIK), and mixing on ice. Three tubes of this mixture were prepared in the same manner.

A thermal cycler was set up under the conditions below, and after the block temperature reached 98° C. the tubes were placed thereon.

A cycle of 98° C. for 10 sec and 72° C. for 70 sec was carried out for five cycles, 2 µL of the primer mixture prepared above was then added and mixed therewith at 72° C., and the reaction below was carried out in the thermal cycler.

| Denature | 98° C. | 10 sec | |
|---|---|---|---|
| Anneal | 60° C. | 5 sec | ×30 cycles |
| Extension | 72° C. | 90 sec | |
| | 72° C. | 60 sec | |
| | 4° C. | ∞ | |

0.5 µL and 1 µL of the reaction mixture after the PCR was completed were subjected to electrophoresis using 0.8% analytical agarose gel and 1×TBE buffer (0.5 µg/mL ethidium bromide).

In agarose gel analysis of the 2nd PCR fragment, it was confirmed that there was amplification of a target single band at about 1.6 kbp. The yield was at least 6 µg.

Purification by PCR Purification Kit

The PCR product was subjected to purification in accordance with the procedural manual for the QIAquick PCR purification kit, thus removing the primer. Elution of DNA in the final step of the purification employed 50 µL of 0.1×TE.

Part of the PCR product from which the primer was removed was diluted by 20 times with 0.1×TE, and quantitatively analyzed by a spectrophotometer.

Treatment of PCR Product with Restriction Enzyme

The purified PCR product was cleaved using the restriction enzymes Bcu I and Sal I.

10 µL of 10× Buffer O (buffer included with enzyme) and 25 units of Sal I were added to 5 µg of the purified PCR product, and the total amount was made up to 100 µL using 0.1×TE. After incubating at 37° C. for 6 hours, 50 ng thereof was taken out, and it was confirmed using 0.8% analytical agarose gel that DNA had not undergone internal decomposition.

The tube containing the enzyme reaction mixture was stored on ice while waiting for confirmation. After confirmation by electrophoresis was carried out, DNA was purified using a QIAquick PCR purification kit.

20 μL of 10× Buffer Tango (buffer included with enzyme) and 110 units of Bcu I were added thereto, and the total amount was made up to 200 μL using 0.1×TE. After incubating at 37° C. for 2 hours, protein was removed.

Fractionation by Agarose Gel and Excision of PCR Product

The PCR product cleaved by the restriction enzyme was fractionated by the same method as in 'Fractionation by agarose gel and excision' described in Example 1, and a target band at about 1.6 kbp was excised. As the gel, 0.8% agarose gel for purification was used, and 90 minutes after starting electrophoresis, when a target band at about 1.6 kbp reached a position about ⅓ of the way along the gel, electrophoresis was ended. As a molecular weight marker, Quick-Load 1 kb DNA Ladder (NEB) was used.

DNA Elution from Agarose Gel

DNA was eluted from the gel excised above by the same method as in 'DNA elution from agarose gel' described in Example 1.

Part of the purified PCR product was diluted by 3 times using 0.1×TE, and quantitatively analyzed using a spectrophotometer.

When the PCR product after the restriction enzyme treatment and the agarose gel purification was subjected to measurement using an absorptiometer, the concentration of DNA was 16 ng/μL. Furthermore, the A260/280 ratio, which indicates the purity, was 2.041.

(3) Ligation of Linear pHU-eCDm-SPCM-pUCori and OriV-RepB Gene

A ligation reaction mixture (reaction mixture 1) and control reaction mixtures (reaction mixture 2 and reaction mixture 3) were prepared as follows.

Reaction Mixture 1

4 μL of 5× Rapid Ligation Buffer, 3.8 μL (50 ng) of pHU-eCDm-SPCM-pUCori (13 ng/μL), 3.9 μL (65 ng) of OriV-RepB fragment (16.5 ng/μL), 1 μL of 5u/μL T4 DNA Ligase, and 7.3 μL of 0.1×TE were added to a sterilized 0.2 mL PCR tube (Bio-BIK) on ice and mixed so that the molar ratio of linear pHU-eCDm-SPCM-pUCori (about 3.6 kbp) to OriV-RepB gene (about 1.6 kbp) was 1:3 (1:1.3 as a ratio by weight), thus giving a ligation reaction mixture (reaction mixture 1).

Reaction Mixture 2

In the same manner, 4 μL of 5× Rapid Ligation Buffer, 3.8 μL (50 ng) of pHU-eCDm-SPCM-pUCori (13 ng/μL), 1 μL of 5 u/μL T4 DNA Ligase, and 11.2 μL of 0.1×TE were added to a sterilized 0.2 mL PCR tube (Bio-BIK) on ice and mixed, thus giving a reaction mixture with only pHU-eCDm-SPCM-pUCori (reaction mixture 2).

Reaction Mixture 3

In the same manner, 4 μL of 5× Rapid Ligation Buffer, 3.9 μL (65 ng) of OriV-RepB fragment (16.5 ng/μL), 1 μL of 5u/μL T4 DNA Ligase, and 11.1 μL of 0.1×TE were added to a sterilized 0.2 mL PCR tube (Bio-BIK) on ice and mixed, thus giving a reaction mixture with only OriV-RepB gene (reaction mixture 3).

A thermal cycler was set up under the conditions below, after the block temperature reached 22° C. the tubes were placed thereon, and ligation was carried out.

| 22° C. | 5 min (ligation reaction) |
| 65° C. | 5 min (reaction stopped) |
| 4° C. | ∞ |

The proportion of the background due to uncleaved plasmid was estimated from reaction mixture 2, and the proportion of the background due to the presence of the plasmid DNA used as a template was estimated from reaction mixture 3.

(4) Transformation of *E. coli*

Transformation of *E. coli* JM109 was carried out using 1 μL of the solution after the ligation reaction by the same method as in 'Transformation of *E. coli*' described in Example 1.

In transformation using the ligation product of the vector and the insert (ligation reaction mixture 1), 238 and 216 colonies were formed on a selective medium per 100 μL of the original bacterial suspension after the transformation, whereas for control reaction mixture 2 in which only the vector was ligated no colonies were detected, and in transformation using control reaction mixture 3 in which only the insert was ligated there were 8 and 6 colonies. The background was very low, suggesting that ligation and transformation were carried out well.

(5) Checking of Plasmid

Culturing of Recombinant *E. coli*

Carried out in accordance with the method described in the section 'Culturing of recombinant *E. coli*' described in Example 1. Culturing was carried out for 22.5 hours.

Extraction of Plasmid DNA

Carried out by the method described in the section 'Extraction of plasmid DNA' described in Example 1.

Measurement of Concentration of Plasmid DNA

Carried out by the method described in the section 'Measurement of concentration of plasmid DNA' described in Example 1.

The A260/280 ratio, which indicates the purity of DNA, was from 1.951 to 1.958, and the purity of the plasmid DNA was good. The yield was at least 10 μg.

Cleavage by Restriction Enzyme

Cleavage by Bcu I on its own, cleavage by Sal I on its own, and cleavage by both Bcu I and Sal I were carried out using 100 ng of plasmid DNA. The reaction conditions were in accordance with the product instructions for the enzyme. The reaction volume was 20 μL.

Agarose Gel Electrophoresis

Carried out by the method described in the section 'Agarose gel electrophoresis' described in Example 1. 0.8% analytical agarose gel was used.

With regard to all six of the candidate strains, two bands at about 3.6 kbp and 1.6 kbp were detected for cleavage with the two types of enzymes Bcu I and Sal I. Furthermore, one band at about 5.2 kbp was detected from cleavage with the enzyme Bcu I on its own or Sal I on its own. This suggests that for all the candidate strains the plasmid size and constitution were as designed.

Checking Plasmid DNA Sequence

Sequencing was carried out using the plasmid extracted above by the same method as in the section 'Checking plasmid DNA sequence' described in Example 1. As a primer, primer sets 1, 2, 3, and 4 in Table 3 described in Example 1 were used. The plasmid nucleotide sequence after alignment was compared with the designed sequence (SEQ ID NO:3).

The plasmid sequences of four strains among the six cloning strains matched SEQ ID NO:3, and it was confirmed that the target strains were obtained. For the remaining two strains, there was a single-nucleotide deletion within the pTB 6 rep unit. One strain was selected from the four strains matching SEQ ID NO:3, and a plasmid extracted from this strain was defined as 'pCDshuttle'.

(6) Transformation of Bifidobacterium

Preparation of Competent Cells

A *Bifidobacterium longum* Re-105A glycerol stock was thawed at room temperature and agitated well. A sterilized glass test tube was charged with 10 mL of IMR conditioned medium, and 100 µL of the thawed bacterial liquid was added thereto and mixed well. This was placed in a sealed container together with a deoxygenating/carbon dioxide generating agent, and culturing was carried out by allowing it to stand at 37° C. for 24 hours (1st culture fluid).

After the 1st culture fluid was agitated well, 100 µL thereof was measured and used to inoculate a test tube charged with 10 mL of IMR conditioned medium, this was placed in a sealed container together with a deoxygenating/carbon dioxide generating agent, and culturing was carried out by allowing it to stand at 37° C. for 18 hours (2nd culture fluid).

30 mL of the IMR conditioned medium was dispensed into each of four 50 mL volume sterilized plastic tubes (BD Falcon™ tubes, Becton, Dickinson and Company, Japan). These tubes were pre-warmed in an incubator at 37° C., and 1.5 mL of the 2nd culture fluid was added to each and agitated well. The caps were lightly closed, the tubes were placed in a sealed container together with a deoxygenating/carbon dioxide generating agent, and culturing was carried out at 37° C. Culturing was ended when the turbidity (wavelength 600 nm) became 0.213 after 1 hour and 35 minutes had elapsed, and the tubes containing the culture fluid were transferred onto ice. They were centrifuged at 8000 rpm for 5 minutes at 4° C. The supernatant was discarded in a clean bench, 5 mL of a PBS buffer pre-cooled in ice was added to each tube containing the bacterial cells, and the bacterial cells were gently suspended. The four tubes containing the bacterial suspension were combined into one tube, and this was centrifuged at 8000 rpm for 5 minutes at 4° C. The supernatant was discarded in a clean bench, and 360 µL of KMR buffer pre-cooled in ice was added to the bacterial cells so as to resuspend them. The bacterial suspension was about 720 µL. This was allowed to stand on ice overnight, thus giving competent cells. A bacterial suspension was prepared by diluting part thereof by 2 times with an equal amount of KMR buffer, and this was defined as doubly diluted competent cells.

Transformation

80 µL of the competent cells was placed in a 1.5 mL volume sterilized microtube ice-cooled in advance. 578 ng (1 µL) of pCDshuttle was added thereto, gently mixed by a pipette, and then allowed to stand on ice for 5 minutes. As a positive control, 498 ng (2 µL) of pAV001-HU-eCD-M968, which had been proved to replicate in a bifidobacteria *B. longum* Re-105A, was mixed with the competent cells by the same procedure as above. In the same manner, the doubly diluted competent cells and 578 ng (1 µL) of pCDshuttle were mixed. Each of the above mixtures were transferred to a cuvette (BM cuvettes, BM Equipment Co., Ltd.) ice-cooled in advance. In this process, competent cells with no DNA added thereto were also added to another cuvette (negative control).

Transformation (electroporation) was carried out using an electroporation system (Gene Pulser II, Bio-Rad Laboratories, Inc.). The electroporator was set to a voltage of 2.0 kV, a capacitor of 25 µF, and a resistor of 200Ω, and operated in accordance with the instruction manual for the system.

After the electric shock, a mixture of 800 µL of IMR liquid medium and 50 µL of a liquid with vitamin C added was immediately added to the cuvette, and this was recovered in a sterilized 2 mL microtube. Each tube was subjected to the same operations, and these 2 mL tubes were decapped and placed in a desiccator. The air within the desiccator was removed using a vacuum pump, and it was filled with carbon dioxide. This operation was repeated three times so as to replace the air within the desiccator with carbon dioxide, and the desiccator was then placed in an incubator set at 37° C. and incubated for 3 hours.

After incubating, each bacterial suspension was agitated well, 100 µL thereof was measured, and plated onto two sheets of IMR agar medium (containing 75 µg/mL SPCM). These plates were placed in a sealed container together with a deoxygenating/carbon dioxide generating agent (Anaero-Pack™-Anaero, Mitsubishi Gas Chemical Company), and culturing was carried out in an incubator set at 37° C. for 3 days.

Culturing of Colony 6 colonies transformed by the pCDshuttle were randomly selected, and used to inoculate test tubes charged with 10 mL of APS-2S-2.5R conditioned medium. As a control, an APS001C master cell bank glycerol stock (manufactured on 2007.3.22, Serial No: 004-0127) was thawed at room temperature, and 100 µL thereof was used to inoculate a test tube charged with 10 mL of the APS-2S-2.5R conditioned medium. These inoculated test tubes were placed in a sealed container together with a deoxygenating/carbon dioxide generating agent, and culturing was carried out by allowing them to stand at 37° C. for 24 hours (1st culture fluid).

After the 1st culture fluids were agitated well, 100 µL thereof was measured and used to inoculate test tubes charged with 10 mL of the APS-2S-2.5R conditioned medium. They were placed in a sealed container together with a deoxygenating/carbon dioxide generating agent, and culturing was carried out by allowing them to stand at 37° C. for 24 hours (2nd culture fluid).

Extraction of Plasmid

Plasmid extraction and purification were carried out using 2 mL of the 1st culture fluids apart from the APS001C by means of a QIAprep Spin Miniprep Kit. Details were in accordance with the product instructions for the kit.

Checking of Plasmid (PCR)

PCR was carried out using the plasmid DNA thus extracted as a template, and the presence/absence of plasmid was checked. A PCR mixture was prepared on ice by adding 5 µL of Plasmid DNA, 10 µL of 5× PrimeStar™ buffer, 4 µL of a dNTP mixture (2.5 mM each), 0.5 µL of 20 µM Check F1 primer, 0.5 µL of 20 µM Check R2 primer, 0.5 µL of Prime-STAR$^{HS}$ DNA polymerase, and 29.5 µL of 0.1×TE to a sterilized 0.2 mL PCR tube (Bio-BIK).

In the same manner, a PCR mixture was prepared as a positive control using as a template a solution prepared by adjusting the concentration of the plasmid pCDshuttle extracted from *E. coli* to 10 pg/mL.

A thermal cycler was set up under the conditions below, and after the block temperature reached 98° C. the tubes were placed thereon.

| Denature | 98° C. | 10 sec | |
|---|---|---|---|
| Anneal | 58° C. | 5 sec | ×30 cycles |
| Extension | 72° C. | 60 sec | |
| | 72° C. | 60 sec | |
| | 4° C. | ∞ | |

Checking of the PCR product was carried out using 1 µL of the reaction mixture after the PCR was completed. As a gel, 0.8% analytical agarose gel was used.

Example 4

Construction of Plasmid 'pBifiCD' (Step 4)
(1) Preparation of pUC Ori-Free Fragment
Cleavage of Plasmid by Restriction Enzyme
pCDshuttle was cleaved by the restriction enzymes Bgl II and Bam HI as follows.

20 µL of 10× Buffer Bam HI (buffer included with enzyme) and 69 units of Bam HI were added to 10 pg of pCDshuttle, the total amount was made up to 200 µL using 0.1×TE, and mixing was carried out well. After incubating at 37° C. for 3 hours and 10 minutes, 50 ng thereof was taken out, and it was confirmed using 0.8% analytical agarose gel that decomposition was complete.

The tube containing the enzyme reaction mixture was stored on ice while waiting for confirmation. After cleavage by Bam HI was confirmed, protein was removed from the enzyme reaction solution.

10 µL of 10× Buffer O (buffer included with enzyme) and 45 units of Bgl II were added thereto, the total amount was made up to 100 µL using 0.1×TE, and mixing was carried out well. After incubating at 37° C. for 2 hours, 100 ng thereof was taken out, and it was confirmed using 0.8% analytical agarose gel that decomposition was complete.

The tube containing the enzyme reaction mixture was stored on ice while waiting for confirmation.

0.1×TE was added to 100 ng of the plasmid DNA solution cleaved by the restriction enzyme so as to make the total amount 10 µL, 1 µL of 10× Loading buffer was added thereto, and mixing was carried out well. This was used as an electrophoresis sample. As a gel, 0.8% analytical agarose gel was used.

Fractionation by Agarose Gel and Excision
The vector cleaved by the restriction enzyme was subjected to electrophoresis for 120 minutes by the same method as in 'Fractionation by agarose gel and excision' described in Example 1, and a DNA band at about 4.5 kbp was excised while confirming that the target band at about 4.5 kbp had separated sufficiently from an unwanted band at about 650 bp. As a molecular weight marker, Quick-Load 1 kbp DNA ladder was used.

DNA Elution from Agarose Gel
DNA was eluted from the gel excised above by the same method as in 'DNA elution from agarose gel' described in Example 1.

Part of the vector purified by agarose gel was diluted by 15 times using 0.1×TE, and quantitatively analyzed using a spectrophotometer.

When the pCDshuttle cleaved by the restriction enzyme and purified by agarose gel was subjected to measurement using an absorptiometer, the concentration of DNA was 47 ng/µL, and the A260/280 ratio, which indicates the purity, was 1.937.

(2) Self-Ligation of Purified pUC Ori-Free Fragment
Ligation Reaction
The purified pUC ori-free fragment (about 4.5 kbp) was subjected to self-ligation. 4 µL of 5× Rapid Ligation Buffer, 1 µL (47 ng) of pUC ori-free fragment (47 ng/µL), 1 µL of 5 u/µL T4 DNA Ligase, and 14 µL of 0.1×TE were added to a sterilized 0.2 mL PCR tube (Bio-BIK) and mixed on ice, thus giving a ligation reaction mixture. 20 tubes of the reaction mixture were prepared.

A thermal cycler was set up under the conditions below, and after the block temperature reached 22° C. the tubes were placed thereon.

| | |
|---|---|
| 22° C. | 5 min (ligation reaction) |
| 65° C. | 5 min (reaction stopped) |
| 4° C. | ∞ |

Purification (Protein Removal and Concentration)
The 20 tubes of the ligation reaction mixture were combined into one sterilized microtube, and protein was then removed. Dissolution of DNA was carried out using 10 µL of 0.1×TE.

(3) Transformation of *Bifidobacterium*
Transformation
Transformation (electroporation) of *Bifidobacterium longum* Re-105A competent cells was carried out using 500 ng (5 µL) of the purified ligation reaction product. As a background control, 500 ng (10 µL) of pUC ori-free fragment that had not been subjected to a ligation reaction was mixed with competent cells in the same manner in a separate tube. The electroporation operation was carried out by the same method as in 'Transformation' described in Example 3.

Culturing of Colony
8 colonies transformed by the purified ligation reaction product were randomly selected, and cultured by the same method as in 'Culturing of colony' described in Example 3.

Extraction of Plasmid
Plasmid extraction and purification were carried out by the same method as in 'Extraction of plasmid DNA' described in Example 1 using 1.5 mL of the 1st culture fluid.

Checking of Plasmid (PCR)
PCR was carried out by the same method as in 'Checking of plasmid' described in Example 3 using the plasmid DNA extracted above as a template.

The PCR product was checked using 1 µL of the reaction mixture after the PCR was completed. As gel, two types, that is, 0.8% and 2% analytical agarose gels were used.

(4) Confirmation of Plasmid Sequence
Culturing
*B. longum* Re-105A/pBifiCD cloning strain glycerol stock was thawed and agitated well, and 100 µL thereof was used to inoculate a test tube charged with 10 mL of APS-2S-2.5R conditioned medium. This test tube was placed in a sealed container together with a deoxygenating/carbon dioxide generating agent, and culturing was carried out by allowing it to stand at 37° C. for 24 hours (1st culture fluid). After the 1st culture fluid was agitated well, 100 µL thereof was measured and used to inoculate each of two test tubes charged with 10 mL of APS-2S-2.5R conditioned medium. These test tubes were placed in a sealed container together with a deoxygenating/carbon dioxide generating agent, and culturing was carried out by allowing them to stand at 37° C. for 24 hours (2nd culture fluid).

Extraction of Plasmid
Plasmid extraction and purification were carried out as follows using an appropriate amount of the 2nd culture fluid by means of a QIAprep Spin Miniprep Kit.

Four 15 mL volume sterilized plastic tubes (BD Falcon™, Becton, Dickinson and Company, Japan) were each charged with 2.5 mL of the 2nd culture fluid, and 7.5 mL of 30 mM GTA buffer was added to each tube. This was agitated and then centrifuged at 12000 rpm for 15 minutes at 25° C., and the supernatant was discarded by pipette. After 10 mL of a 30 mM GTA buffer was added to bacterial cells in the tubes, they were centrifuged at 12000 rpm for 15 minutes at 25° C., and the supernatant was discarded by pipette. After combining two tubes containing the bacterial cells into one, 1 mL of an N-acetylmuramidase solution (prepared at 3000 units/mL by adding 30 mM GTA buffer to a lyophilized N-acetylmuramidase product manufactured by Seikagaku Corporation) was added to each and mixed well. After incubating these tubes in a water bath set at 50° C. for 3 hours, 250 µL of 20 mg/mL Proteinase K (QIAGEN) was added thereto, mixed well, and incubation was carried out in a water bath set at 60° C. for 30 minutes. The two tubes were combined into one.

An equal amount of Buffer P1 (included with kit) was added thereto and mixed (A). This mixture was divided into four 15 mL volume plastic tubes, an equal amount to that of A of a Lysis solution (0.2 M NaOH/2% SDS) was added thereto and tumble mixed, a volume of 1.4 times that of A of Buffer N3 (included with kit) was then added thereto and tumble mixed, and the bacterial cells were subjected to bacteriolysis and neutralization. After centrifuging at 12000 rpm for 15 minutes at 25° C., the supernatant was collected in a 15 mL volume plastic tube. The liquid thus collected was purified using eight columns of QIAquick Spin Column (included with kit). The purification method was in accordance with the procedural manual for the kit. The DNA elution of the final step was carried out using 50 µL of 0.1×TE, thus giving about 400 µL of a plasmid solution.

Checking Plasmid DNA Sequence

Sequencing was carried out using the plasmid extracted above by the same method as in the section 'Checking plasmid DNA sequence' described in Example 1. As primers, primer sets 1, 3, and 4 in Table 3 described in Example 1 were used. The plasmid nucleotide sequence after alignment was compared with the designed sequence (SEQ ID NO:4).

The result of determining the whole sequence of the plasmid extracted from the cloning strain was that the *B. longum* Re-105A/pBifiCD plasmid sequence matched SEQ ID NO:4. Plasmid extracted from this cloning strain was defined as 'pBifiCD'.

Test Example 1

Checking Transformation and Basic Properties of *Bifidobacterium*

(1) Checking Transformation of *B. Longum* Re-105A

A self-ligation product formed by removing the pUC ori site from pCDshuttle and ring-closing and the result of transformation of *B. longum* Re-105A using pCDshuttle were checked.

The same competent cells were used for plates 1 to 5. For a negative control (plate No. 1) to which no plasmid was added, the number of colonies was 1 and 0.

However, even for a positive control (plate 5) transformed using shuttle plasmid pAV001-HU-eCD-M968 (Patent Publication 5; WO 2007-136107) that had already been proved to replicate in *Bifidobacterium*, the number of colonies was 5 and 2, and the difference in number from that of the negative control was small. This suggests that the efficiency of transforming the competent cells used in plates 1 to 5 was low.

On the other hand, for plate 6, the concentration of the competent cells used was diluted by 2 times, and when transformation was carried out using pCDshuttle, at least 500 colonies were formed per plate. A negative control for plate 6 was not carried out, but it is surmised that the colonies on plate 6 were highly likely to have been transformed by plasmid pCDshuttle. Furthermore, it was found that the concentration of the competent cells contributed greatly to the transformation efficiency.

Moreover, comparing a case in which ligation of the fragment in which pUC ori had been removed from pCDshuttle was carried out and a case in which it was not carried out, as a result of transformation thereby (plates 3 and 4 respectively), the number of colonies was 3 and 8 for plate 3 and 1 and 2 for plate 4, and the number of colonies was small in both cases.

The results are given in Table 4.

TABLE 4

Transformation of *B. longum* Re-105A

| Plate No. | Competent cell | DNA | (cfu/plate) Plating (100 µL) |
|---|---|---|---|
| 1 | *B. longum* Re-105A (×1) | — | 1 0 |
| 2 | *B. longum* Re-105A (×1) | pCDshuttle | 2 6 |
| 3 | *B. longum* Re-105A (×1) | pCDshuttle without pUC ori ligation+ | 3 8 |
| 4 | *B. longum* Re-105A (×1) | pCDshuttle without pUC ori ligation− | 1 2 |
| 5 | *B. longum* Re-105A (×1) | pAV001-HU-eCD-M968 | 5 2 |
| 6 | *B. longum* Re-105A (×2 dilution) | pCDshuttle | >500 >500 |

(2) Checking Plasmid of Transformed *B. Longum* Re-105A

When PCR was carried out with Check primer using as a template a plasmid extracted from eight *B. longum* Re-105A/pBifiCD cloning strains and six *B. longum* Re-105A/pCDshuttle cloning strains, an amplification product of about 500 bp was detected for the *B. longum* Re-105A/pBifiCD cloning strains. For the *B. longum* Re-105A/pCDshuttle cloning strains, an amplification product at 1.1 kbp was detected. It was confirmed thereby that all of the cloning strains had a plasmid. It was also shown that pBifiCD did not contain a pUC ori fragment.

Test Example 2

Checking Cytosine Deaminase Activity

Cytosine deaminase (CD) activity was checked using eight *B. longum* Re-105A/pBifiCD cloning strains and six *B. longum* Re-105A/pCDshuttle cloning strains.

1 mL of each 2nd culture fluid in APS-2S-2.5R conditioned medium was washed with Tris buffer (pH 8.4) three times and then ultrasonically ground, thus extracting total protein. The total protein amount was quantitatively measured by a modified Lowry method, and an enzyme reaction employing 5-fluorocytosine (5-FC) as a substrate was carried out using 5 pg of total protein. 5-Fluorouracil (5-FU) formed by the enzyme reaction and the amount of 5-FC remaining were quantitatively measured by liquid chromatography, and CD enzyme activity was calculated.

From the result of measuring the CD activity of the *B. longum* Re-105A/pBifiCD cloning strains and the *B. longum* Re-105A/pCDshuttle cloning strains, the CD activity of the eight *B. longum* Re-105A/pBifiCD cloning strains was 8.07-10.29 (average: 8.74) units/µg of total protein, and there was hardly any difference between bacterial strains.

Furthermore, the CD activity of the six *B. longum* Re-105A/pCDshuttle cloning strains was 8.13-9.66 (average: 8.69) units/µg of total protein, and there was similarly hardly any difference between bacterial strains.

The CD activities of the two cloning strains were almost the same, but for the average values the CD activity of the *B. longum* Re-105A/pBifiCD cloning strains was slightly stronger; there was no reduction in the CD activity due to the pUC ori fragment being removed, but rather it is suggested that it acted well.

It was proved by this test that pCDshuttle and pBifiCD replicated in *Bifidobacterium* and had adequate CD activity. The measurement results are shown in Table 5.

TABLE 5

CD activities using total proteins

| Strains | | Peak area 5-FU | Peak area 5-FC | Conversion rate (%) | Protein conc. (mg/mL) | CD activity (uints/mg total protein) |
|---|---|---|---|---|---|---|
| *B. longum* Re-105A/ pCDshuttle | #1 | 83317 | 874312 | 9.40 | 0.2556 | 9.4 |
| | #2 | 85159 | 867227 | 9.66 | 0.2985 | 9.66 |
| | #3 | 71781 | 843867 | 8.47 | 0.3572 | 8.47 |
| | #4 | 68331 | 840645 | 8.13 | 0.3662 | 8.13 |
| | #5 | 69681 | 837294 | 8.31 | 0.3798 | 8.31 |
| | #6 | 68460 | 841469 | 8.14 | 0.3775 | 8.14 |
| *B. longum* Re-105A/ pBifiCD | #1 | 75600 | 829106 | 9.03 | 0.2805 | 9.03 |
| | #2 | 72268 | 838034 | 8.58 | 0.303 | 8.58 |
| | #3 | 67964 | 843275 | 8.07 | 0.3188 | 8.07 |
| | #4 | 68377 | 837315 | 8.16 | 0.3324 | 8.16 |
| | #5 | 71344 | 835183 | 8.51 | 0.3753 | 8.51 |
| | #6 | 77285 | 870090 | 8.82 | 0.2805 | 8.82 |
| | #7 | 85810 | 814454 | 10.29 | 0.3053 | 10.29 |
| | #8 | 70636 | 832980 | 8.45 | 0.373 | 8.45 |

Test Example 3

Checking Plasmid Retention Stability

The plasmid retention stability when a culture fluid sufficiently activated by culturing in a medium containing spectinomycin was cultured in a medium with no spectinomycin added thereto was checked as follows.

Selective Culturing in Medium with SPCM Added

After glycerol stocks of two *B. longum* Re-105A/pBifiCD cloning strains and a glycerol stock of one *B. longum* Re-105A/pCDshuttle cloning strain were thawed and agitated well, 100 µL thereof was measured and used to inoculate test tubes charged with 10 mL of APS-2S-2.5R conditioned medium. Inoculation with APS001C MCB (Serial No. 004-0116) was also carried out by the same procedure. These test tubes were placed in a sealed container together with a deoxygenating/carbon dioxide generating agent, and culturing was carried out by allowing them to stand at 37° C. for 24 hours (1st culture fluid). After the 1st culture fluid was agitated well, 100 µL thereof was measured and used to inoculate two test tubes charged with 10 mL of APS-2S-2.5R conditioned medium. These test tubes were placed in a sealed container together with a deoxygenating/carbon dioxide generating agent, and culturing was carried out by allowing them to stand at 37° C. for 24 hours (2nd culture fluid).

Nonselective Culturing in Medium with No SPCM Added Thereto 10 mL test tubes charged with nonselective APS-2S-2.5R conditioned medium were warmed in advance in a water bath set at 37°, and this medium was inoculated with 10 µL of each of the 2nd culture fluids in the SPCM added medium within a clean bench (0.1% bacterial inoculation). After the inoculation, each test tube was placed in a sealed container together with a deoxygenating/carbon dioxide generating agent, and placed in an incubator set at 37° C. A series of these operations were carried out quickly so that change in temperature of the medium was minimized. After these test tubes were cultured for 24 hours, using each culture fluid as an inoculum, subculturing onto the nonselective APS-2S-2.5R conditioned medium was repeated by the same method.

After the third passage the culture fluid in the nonselective APS-2S-2.5R conditioned medium was agitated by shaking well, 100 µL thereof was measured and added to 9.9 mL of an anaerobic diluent ($10^2$ times dilution liquid) and mixed well. The $10^2$ times dilution liquid was diluted by the same method to give a $10^4$ times dilution liquid, then to give a $10^6$ times dilution liquid. 100 µL of the $10^6$ times dilution liquid was plated onto each of five sheets of BL agar medium. These plates were placed in a sealed container together with a deoxygenating/carbon dioxide generating agent, and anaerobic culturing was carried out in an incubator set at 37° C. for 2 days.

Replication to BL-bS Agar Medium 300 well separated colonies were randomly selected from the BL agar medium and used. The colonies were fished using a sterilized tooth pick and used to inoculate BL-bS agar medium and BL agar medium in sequence. Inoculation was carried out on a total of 6 sheets of agar media at 50 per sheet. The agar media after inoculation were placed in a sealed container together with a deoxygenating/carbon dioxide generating agent according to the volume of the container so as to maintain an anaerobic state, and culturing was carried out at 37° C. for 1 day.

Counting after completion of culturing was carried out by marking puncture traces from the tooth pick where there was no apparent proliferation of bacterium, and counting puncture traces other than these where bacteria could be seen to be proliferating. Since bacteria retaining plasmid were SPCM-resistant, the percentage of plasmid-retaining bacteria was given as the percentage of SPCM-resistant bacteria. The percentage of plasmid-retaining bacteria was determined from the equation below.

$$\text{Percentage of plasmid-retaining bacteria} = \frac{\text{Number of bacterial proliferation puncture marks on } BL\text{-}bS \text{ agar medium}}{\text{Number of bacterial proliferation puncture marks on } BL \text{ agar medium}} \times 100 \quad [\text{Equation 1}]$$

From the result of measuring plasmid retention stability, the percentage of spectinomycin-resistant bacteria in *B. longum* Re-105A/pBifiCD cloning strains #1 and #5, that is, the percentage of plasmid-retaining bacteria, was the very high value of 87.7% for both strains.

Furthermore, the percentage of plasmid-retaining bacteria in *B. longum* Re-105A/pCDshuttle was 80.3%.

On the other hand, the percentage of plasmid-retaining bacteria in *B. longum* Re-105A/pAV001-HU-eCD-M968 transformed by shuttle plasmid pAV001-HU-eCD-M968 (APS001C: Patent Publication 6; WO 2007-136107) was 71.7%, which was much lower than the percentage of the plasmid-retaining bacteria in *B. longum* Re-105A/pBifiCD of the present invention.

It was confirmed that the plasmid pBifiCD of the present invention was retained stably within the bifidobacteria *B. longum* Re-105A, and *B. longum* Re-105A/pBifiCD transformed by the plasmid pBifiCD of the present invention showed very high plasmid retention stability.

Furthermore, compared with B. longum Re-105A/pAV001-HU-eCD-M968, the two cloning strains showed a very good percentage of plasmid-retaining bacteria and, moreover, the B. longum Re-105A/pBifiCD cloning strain gave a higher percentage of plasmid-retaining bacteria than that of the B. longum Re-105A/pCDshuttle cloning strain, thus confirming that removal of the pUC ori fragment improved the percentage of plasmid-retaining bacteria.

The measurement results are shown in Table 6.

TABLE 6

Stability of plasmid segregation

| Strains | Growth on BL-bS | Growth on BL | SPCM resistant (%) |
|---|---|---|---|
| B. longum Re-105A/pBifi CD #1 | 263 | 300 | 87.7 |
| B. longum Re-105A/pBifi CD #5 | 263 | 300 | 87.7 |
| B. longum Re-105A/pCDshuttle #1 | 240 | 299 | 80.3 |
| APS001C MCB | 215 | 300 | 71.7 |

Test Example 4

Checking Ability of Plasmid 'pBifiCD' to Transform E. coli

Checking that E. coli was not transformed by plasmid 'pBifiCD' of the present invention, using the shuttle plasmid 'pCDshuttle' as a control, was carried out as follows.

(1) Preparation of Plasmid

The plasmid 'pBifiCD' of the present invention and the control plasmid 'pCDshuttle' were prepared as follows.

Culturing

APS-2S-2.5R conditioned medium was inoculated at 1% with the bifidobacteria transformed by the plasmid 'pBifiCD' (B. longum Re-105A/pBifiCD) prepared in Example 4, placed in a sealed container with a deoxygenating/carbon dioxide generating agent, and cultured at 37° for 24 hours. After stirring well, APS-2S-2.5R conditioned medium was inoculated with 1% thereof and culturing was carried out for 24 hours in the same manner.

Similarly, APS-2S-2.5R conditioned medium was inoculated at 1% with the bifidobacteria transformed with the shuttle plasmid 'pCDshuttle' (B. longum Re-105A/pCDshuttle) prepared in Example 3, placed in a sealed container with a deoxygenating/carbon dioxide generating agent, and cultured at 37° for 24 hours. After stirring well, APS-2S-2.5R conditioned medium was inoculated with 1% thereof and culturing was carried out for 24 hours in the same manner.

Extraction of Plasmid 2 mL of each of the above culture fluids was washed twice with 30 mM GTA buffer (pH 5.5), and subjected to N-acetylmuramidase treatment, then to Proteinase K treatment. Purification was carried out by means of a QIAprep Spin Mini-Prep Kit to thus extract plasmid DNA, and about 9 μg of plasmid DNA was obtained in each case.

(2) Transformation of E. coli

Transformation of E. coli JM109 competent cells (Takara Bio Inc.) (100 μL) was carried out by heat shock using 50 ng (1 μL) each of the plasmids 'pCDshuttle' and 'pBifiCD' prepared above. The transformation method was in accordance with the product instructions supplied with the competent cells.

100 μL of each of the bacterial suspensions after heat shock and incubation with added SOC medium were plated onto two LB agar media (containing 75 μg/mL spectinomycin), and cultured at 37° C. overnight.

From the result of checking for the presence or absence of colonies on each of the plates after culturing, colonies were detected only in E. coli transformed using the control plasmid 'pCDshuttle'.

On the other hand, colonies were not detected after transformation by a negative control in which 0.1×TE was added instead of plasmid, or by the plasmid 'pBifiCD' of the present invention.

It was confirmed that even when the plasmid 'pBifiCD' of the present invention was forcibly introduced into E. coli, it could not be replicated within E. coli.

The results are given in Table 7.

TABLE 7

Transformation of E. coli JM109 with either pCDshuttle or pBifiCD

| Sample name | Number of colonies per plate |
|---|---|
| pCDshuttle | 35, 53 |
| pBifiCD | 0, 0 |
| 0.1xTE (Negative control) | 0, 0 |

Test Example 5

Checking of Antitumor Effect of B. Longum Re-105A/pBifiCD Cloning Strain (1) Preparation of Cultured Viable Cells of B. Longum Re-105A/pBifiCD Cloning Strain (Test Drug)

Activated culturing was carried out by thawing a glycerol stock of B. longum Re-105A/pBifiCD cloning strain at normal temperature, inoculating with an appropriate amount thereof a test tube charged with a liquid medium with added calcium carbonate, placing it in a sealed container together with a deoxygenating/carbon dioxide generating agent, and anaerobically culturing in an incubator at 37° C. for 24 hours. Subsequently, a test tube charged with a liquid medium without added calcium carbonate was inoculated with an appropriate amount of this liquid culture, and cultured under the same anaerobic conditions for 18 hours (main culture).

The liquid culture was transferred to a 50 mL volume polypropylene conical tube (Becton, Dickinson and Company, Japan), and 5 mL of this mixed liquid culture was mixed well with a 4-fold amount (20 mL) of cooled (5° C.) physiological saline, three tubes being thus prepared. Washing was carried out by subjecting each tube to centrifugation at 8,000 rpm for 10 minutes while cooling (4° C.) and, after the supernatant was discarded, further adding 20 mL of cooled physiological saline thereto to thus suspend the bacteria (washing operation 1). This washing operation was carried out twice more, and after the bacterial liquids that had been washed a total of three times were combined in one tube, the volume of the bacterial suspension was adjusted to 6.5 mL. The bacterial suspension thus washed was filtered using an 8 μm membrane filter (polycarbonate, Toyo Roshi Kaisha, Ltd., K800A025A), and the viable bacteria in a filtrate thus collected (cultured viable bacteria liquid) were used as a test drug.

(2) Culturing of Transplanted Tumor Cells

Human breast cancer cell line KPL-1 cells were cultured at 37° C. under conditions of 5% $CO_2$ in DMEM medium with added 1 v/v % penicillin (50000 U/mL)/streptomycin (50 mg/mL) and FBS (10 v/v %) immobilized at 56° C. for 30 minutes.

When confluent, after washing with 1×PBS(−), 1× trypsin-EDTA was added so as to strip the cells, and the cells collected by centrifugation (1000 rpm/5 minutes) were diluted as appropriate with DMEM medium and subcultured.

In a transplantation experiment, fifth passage cells were used. The number of viable cells that had not been stained by Trypan blue was counted by a Thoma hemocytometer (Thoma 0.1 mm deep ERMA, Tokyo), and the number of cells was adjusted to $2.5 \times 10^6$ cell/mL by suspending them in Hanks' solution.

(3) Preparation of Tumor-Bearing Nude Mouse and Measurement of Volume of Tumor 0.2 mL of the KPL-1 cell suspension prepared above was transplanted under the skin of the back side of the right forelimb of a nude mouse ($5 \times 10^5$ cells/mouse).

The volume of a tumor after transplantation was determined from the equation below by measuring the dimensions of the tumor (major diameter, minor diameter, thickness) using calipers.

Tumor volume (mm³)=major diameter (mm)×minor diameter (mm)×thickness (mm)/2

(4) Grouping and Administration of Cultured Viable Bacteria (Test Drug), Sugar Source (Lactulose), And Prodrug (5-FC)

Grouping and Administration of Cultured Viable Bacteria (Test Drug)

16 KPL-1 tumor-bearing nude mice having a tumor volume of on the order of 60 to 95 mm³ were selected and evenly divided into two groups (8 mice per group), one group was used as a control group (non-treated group) and the other group was used as a treated group.

0.3 mL per mouse of cultured viable bacteria (test drug) was intravenously administered to the treated group three times (AM/PM) per day for 2 days (day 1 and day 2).

The total volume of cultured viable bacteria administered was 1.8 mL, and the total number of cells administered was $5.9 \times 10^9$ cfu/mouse.

The number of viable bacteria administered was measured as follows.

Measurement of Number of Viable Bacteria

A cultured bacterial liquid was diluted $10^6$ times with an anaerobic diluent, and 100 μL thereof was plated onto three BLFS plates and anaerobically cultured in a sealed container (AneroPack rectangular jar, Mitsubishi Gas Chemical Co., Ltd.) together with a deoxygenating/carbon dioxide generating agent in an incubator at 37° C. for 3 days. The number of bacteria administered was calculated from the equation below from a plate where the number of colonies detected was on the order of 30 to 300.

Number of bacteria administered (cfu)=Number of colonies (a)×dilution ratio at plating (b)×conversion factor (c) per 1 mL of preparation×dose (mL)

(a): (P1+P2+P3)/3 [average number of colonies of 3 plates (P1, P2, P3)]

(b): × $10^6$ [$10^6$ times dilution]

(c): × 10 [100 μL each was plated per plate]

Administration of Lactulose

A lactulose solution was further administered as follows to the treated group as a sugar source for the bacteria.

1 mL of a lactulose solution that had been dissolved in purified water at 20% (w/v) and autoclaved at 121° C. for 20 minutes was administered into the abdominal cavity of a mouse once per day.

The administration period was 21 days (Day 3 to Day 23) from the day after administration of cultured viable bacteria was completed.

Administration of Flucytosine (5-FC)

0.4 mL of 5-FC solution was orally administered to a mouse three times per day (at around 9:00, 14:00, and 18:00) (total administration amount 1.2 mL).

The administration period was 21 days (Day 3 to Day 23) from the day after administration of APS001F cultured viable bacteria was completed.

(5) Checking of Tumor Growth Suppression Effect

Tumor diameter was measured for all of the mice before starting the treatment (at the time of grouping) and 24 days after the treatment had been started at a frequency of once in 3 to 4 days, and the effect on tumor growth was checked.

An average value±SD of mouse tumor volume of each group was calculated, and the antitumor effect was judged using as an index the relative tumor volume ratio [T/C(%)] with respect to the control group.

Tumor volumes (average value±SD) of the control group and the treated group are shown in Table 8. Furthermore, change in tumor volume over days is shown in FIG. 5.

The relative tumor volume ratio [T/C(%)] of the treated group on the test end day (day 24) was 23.0%, and a prominent tumor growth suppression activity was observed.

TABLE 8

Anti-tumor effect of *B. longum* Re-105A/pBifiCD cloning strain

| Treatment | No of mice | Timor size (mm³) Mean ± SD | | | | | | | T/C(%) at day 24 | Two tailed t-test (p-value) |
|---|---|---|---|---|---|---|---|---|---|---|
| | | day 0 | 3 | 7 | 10 | 14 | 17 | 21 | 24 | | |
| A) Non treated control | 8 | 74.5 | 122.3 | 205.3 | 370.1 | 560.8 | 912.0 | 1612.1 | 2115.7 | — | — |
| | | 12.5 | 44.2 | 78.7 | 212.5 | 285.4 | 564.8 | 765.4 | 1009.9 | | |
| B) APS001F (intact) + 5-FC + Lactulose | 8 | 74.7 | 92.4 | 132.3 | 154.5 | 270.1 | 365.6 | 484.4 | 486.5 | 23.0 | 0.002 |
| | | 10.7 | 15.4 | 54.7 | 41.8 | 120.0 | 180.4 | 211.8 | 265.0 | | |

Industrial Applicability

The object of the present invention is to provide an expression vector that is replicated only in a transformant bacterium and is not replicated in a bacterium other than the transformant bacterium, and in particular not in a pathogenic, or aerobic or facultative anaerobic bacterium, such as *E. coli*, and a process for constructing same. Furthermore, the object of the present invention is to provide a gene transporter formed from an anaerobic microorganism transformed by the expression vector, a pharmaceutical composition that contains the gene transporter, and a solid tumor treatment agent that contains the bacterium.

The vector of the present invention is a very safe vector that does not contain an origin of replication that functions in a bacterium, particularly *E. coli*, other than the transformant bacterium, and has no possibility of being replicated in a bacterium other than the transformant bacterium, and particularly not in a pathogenic, or aerobic or facultative anaerobic bacterium, such as E. coli. A gene transporter transformed using the vector of the present invention has high plasmid retention stability, and there is no possibility, even if it is horizontally transferred to a bacterium other than the transformant bacterium, and particularly to a pathogenic, or aerobic or facultative anaerobic bacterium, such as E. coli, of it being replicated in the bacterium, and it is promising as a very safe and high quality gene transporter.

We claim:

1. An isolated expression vector that functions in an anaerobic bacterium, wherein said expression vector does not contain a plasmid replication unit that functions in E. coli, and wherein the expression vector comprises (1) a plasmid replication unit that functions in the anaerobic bacterium, and (2) a protein expression unit comprising a DNA coding for a protein having a therapeutic activity for a disease that is in an anaerobic environment and a DNA fragment comprising a promoter and a terminator that function in the anaerobic bacterium, wherein said protein is selected from the group consisting of cytosine deaminase, nitroreductase, and β-glucuronidase.

2. The expression vector according to claim 1, wherein the anaerobic bacterium is an enterobacterium other than E. coli.

3. The expression vector according to claim 2, wherein the enterobacterium other than E. coli is selected from the group consisting of Bifidobacterium, Lactobacillus, Enterococcus, Streptococcus, and Clostridium.

4. The expression vector according to claim 1, wherein the plasmid replication unit that functions in the anaerobic bacterium is a plasmid replication unit that functions in an anaerobic bacterium selected from the group consisting of Bifidobacterium, Lactobacillus, Enterococcus, Streptococcus, and Clostridium.

5. The expression vector according to claim 4, wherein the plasmid replication unit that functions in the anaerobic bacterium is a plasmid replication unit that functions in Bifidobacterium.

6. The expression vector according to claim 5, wherein the plasmid replication unit that functions in *Bifidobacterium* is a pTB6 replication unit comprising an OriV region and a RepB gene.

7. The expression vector according to claim 6, wherein the pTB6 replication unit comprises the $1796^{th}$ to the $3391^{st}$ nucleotides of SEQ ID NO:4 or a single-nucleotide polymorphism thereof.

8. The expression vector according to claim 1, wherein said protein is cytosine deaminase.

9. The expression vector according to claim 8, comprising SEQ ID NO:4 (pBifiCD).

10. An isolated gene transporter comprising the anaerobic bacterium transformed with the expression vector according to claim 1.

11. The gene transporter according to claim 10, wherein the anaerobic bacterium is an enterobacterium other than *E. coll*.

12. The gene transporter according to claim 11, wherein the enterobacterium is selected from the group consisting of *Bifidobacterium Lactobacillus, Enterococcus, Streptococcus*, and *Clostridium*.

13. The gene transporter according to claim 12, wherein the enterobacterium is *Bifidobacterium*.

14. The gene transporter according to claim 13, wherein the *Bifidobacterium* is selected from the group consisting of *Bifidobacterium adolescentis, Bifidobacterium animalis, Bifidobacterium infantis, Bifidobacterium thermophilum, Bifidobacterium pseudolongum, Bifidobacterium bifidum, Bifidobacterium breve*, and *Bifidobacterium longum*.

15. The gene transporter according to claim 14, wherein the bifidobacterium s *Bifidobacterium longum*.

16. The gene transporter according to claim 10, wherein said gene transporter is capable of growing in a tumor tissue that is in an anaerobic environment, and is capable of expressing said protein, wherein said protein is selected from the group consisting of cytosine deaminase, nitroreductase, and β-glucuronidase.

17. The gene transporter according to claim 16, wherein said protein is cytosine deaminase.

18. The gene transporter according to claim 17, wherein the gene transporter is *Bifidobacterium longum* 105-A/pBifiCD (National Institute of Technology and Evaluation Patent Microorganisms Depositary (NPMD) Accession No. NITE BP-491).

19. A pharmaceutical composition comprising the gene transporter according to claim 17, and 5- fluorocytosine.

20. A pharmaceutical composition comprising the gene transporter according to claim 10.

21. A process for constructing an expression vector that functions in an anaerobic bacterium, comprising (i) producing a shuttle plasmid comprising (1) a plasmid replication unit that functions in the anaerobic bacterium, (2) a protein expression unit comprising a DNA coding for a protein having target activity and a DNA fragment comprising a promoter and a terminator that function in the anaerobic bacterium, and (3) a selection marker, the shuttle plasmid being capable of replication in both *E. coli* and a host bacterium other than *E. coli*, and (ii) removing from the shuttle plasmid a plasmid replication unit that functions in *E. coli*.

* * * * *